United States Patent
Stagljar et al.

(10) Patent No.: US 11,123,330 B2
(45) Date of Patent: Sep. 21, 2021

(54) METHODS AND COMPOSITIONS FOR INHIBITING MUTANT EGFR SIGNALING

(71) Applicant: The Governing Council of the University of Toronto, Toronto (CA)

(72) Inventors: Igor Stagljar, Toronto (CA); Jamie Snider, Etobicoke (CA); Punit Saraon, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 1 day.

(21) Appl. No.: 16/146,611

(22) Filed: Sep. 28, 2018

(65) Prior Publication Data

US 2019/0091205 A1    Mar. 28, 2019

Related U.S. Application Data

(60) Provisional application No. 62/564,599, filed on Sep. 28, 2017.

(51) Int. Cl.

| | |
|---|---|
| *A61K 31/423* | (2006.01) |
| *A61K 31/497* | (2006.01) |
| *A61P 35/00* | (2006.01) |
| *A61K 31/553* | (2006.01) |
| *A61K 31/4535* | (2006.01) |
| *A61K 39/395* | (2006.01) |

(52) U.S. Cl.
CPC ........ *A61K 31/423* (2013.01); *A61K 31/4535* (2013.01); *A61K 31/497* (2013.01); *A61K 31/553* (2013.01); *A61K 39/3955* (2013.01); *A61P 35/00* (2018.01)

(58) Field of Classification Search
CPC .............................. A61K 31/423; A61P 35/00
USPC ...................................................... 424/180.1
See application file for complete search history.

(56) References Cited

U.S. PATENT DOCUMENTS

| | | |
|---|---|---|
| 6,217,866 B1 | 4/2001 | Schlessinger et al. |
| 6,235,883 B1 | 5/2001 | Jakobovits et al. |
| 9,730,926 B2 | 8/2017 | Lin et al. |

OTHER PUBLICATIONS

Ercan Dalie et al. EGFR mutations and resistance to Irreversible pyrimidine based EGFR inhibitors. Clin Cancer Res. Sep. 1, 2015; 21(17): 3913-3923.

Cabanero M., et al. Management of EGFR-mutated non-small-cell lung cancer: practical implications from a clinical anld pathology perspective. Current Oncology, vol. 24, No. 2, Apr. 2017, pp. 111-119.

Lee, Ho-Jun. et al. Non-Covalent Wild-Type-Sparing Inhibitors of EGFR T790M. Cancer Discov. Feb. 2013,; 3(2)168-181.

Costa, Daniel B. and Kobayashi, Susumu S. Whacking a mole-cule: clinical activity and mechanisms of resistance to third generation EGFR inhibitors in EGFR mutated lung cancers with EGFR-TM790. Transl Lung Cancer Res. 2015; 4(6):809-815.

Uchibori, Ken et al. Brigatinib combined with anti-EGFR antibody overcomes osimertinib resistance in EGFR-mutated non-small-cell lung cancer. Nature Communications, Mar. 2017, 8:14768.

Kim, Su-Nam et al. 7-Diethylamino-3(2'-benzoxazolyl)-coumarin is a novel microtubule inhibitor with antimitotic activity in multidrug resistant cancer cells. Biochemical Pharmacology. vol. 77, Issue 12, Jun. 2009, pp. 1773-1779.

Stone, R.M. et al. Midostaurin plus Chemotherapy for Acute Myeloid Leukemia with a FLT3 Mutation. The New England Journal of Medicine. 377;5, Aug. 2017, pp. 454-464.

Petschnigg, Julia et al. Systematic Identification of Oncogenic EGFR Interaction Partners. Journal of Molecular Biology. Jan. 20, 2017; 429(2): 280-294.

Yu, Helena A. et al. Analysis of Tumor Specimens at the Time of Acquired Resistance to EGFR TKI therapy in 155 patients with EGFR mutant Lung Cancers. Clin. Cancer Res. Apr. 15, 2013; 19(8):2240-2247.

Thress, Kenneth S. et al. Acquired EGFR C797S mediates resistance to AZD9291 in advanced non-small cell lung cancer harboring EGFR TM790M. Nat Med. Jun. 2015; 21(6): 560-562.

Zabludoff, Sonya D. et al. AZD7762, a novel checkpoint kinase inhibitor, drives checkpoint abrogation and potentiates DNA-targeted therapies. Mol Cancer Ther 2008;7(9), Sep. 2008.

Sausville, Edward et al. Phase I dose-escalation study of AZD7762, a checkpoint kinase inhibitor, in combination with gemcitabine in US patients with advanced solid tumors. Cancer Chemother Pharmacol. Mar. 2014: 73(3): 539-549.

Levis, Mark. Midostaurin approved for FLT3-mutated AML. Blood, Jun. 29, 2017, vol. 129, No. 26.

*Primary Examiner* — Yan Xiao
(74) *Attorney, Agent, or Firm* — Bereskin & Parr LLP; Carmela De Luca

(57) ABSTRACT

Methods of inhibiting mutant EGFR and methods of treating a subject afflicted with a lung cancer having a mutant EGFR, having for example a C797 mutation, are described. The methods comprise administering to a cell or a subject in need thereof a therapeutically effective amount of a compound selected from 3-(1,3-benzoxazol-2-yl)-7-(diethylamino)-2H-chromen-2-one and a structurally related analog thereof; midostaurin; and AZD7622 and a structurally related analog thereof; and mixtures thereof. Compositions and combinations comprising the compounds of the disclosure as well as uses are also provided.

20 Claims, 41 Drawing Sheets

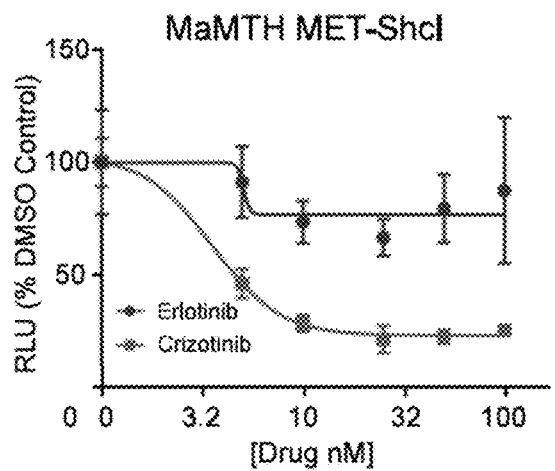
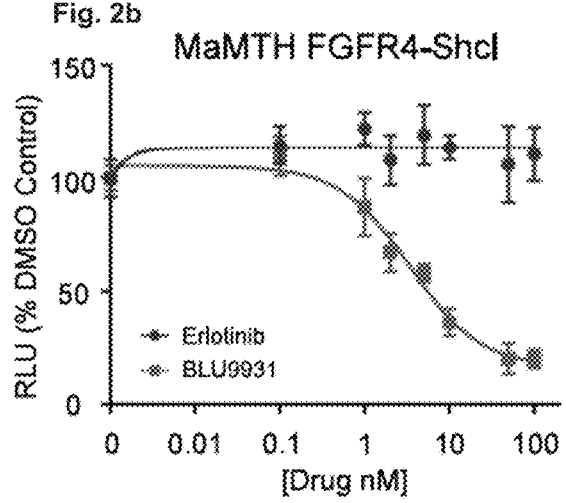
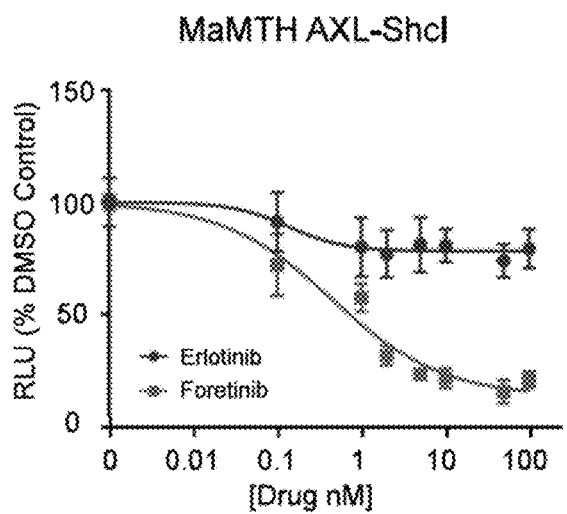
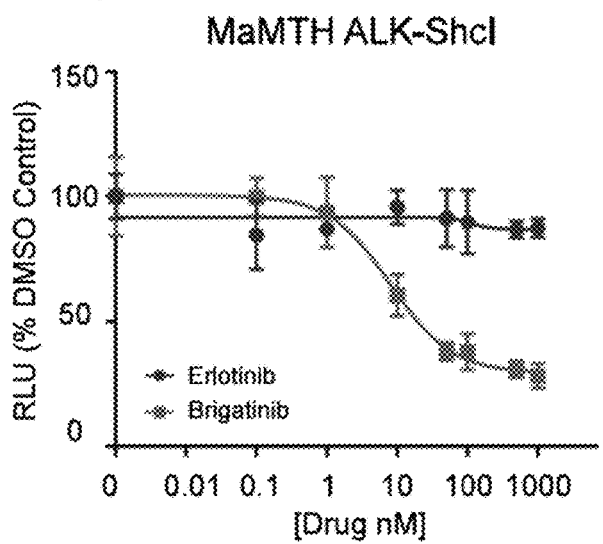
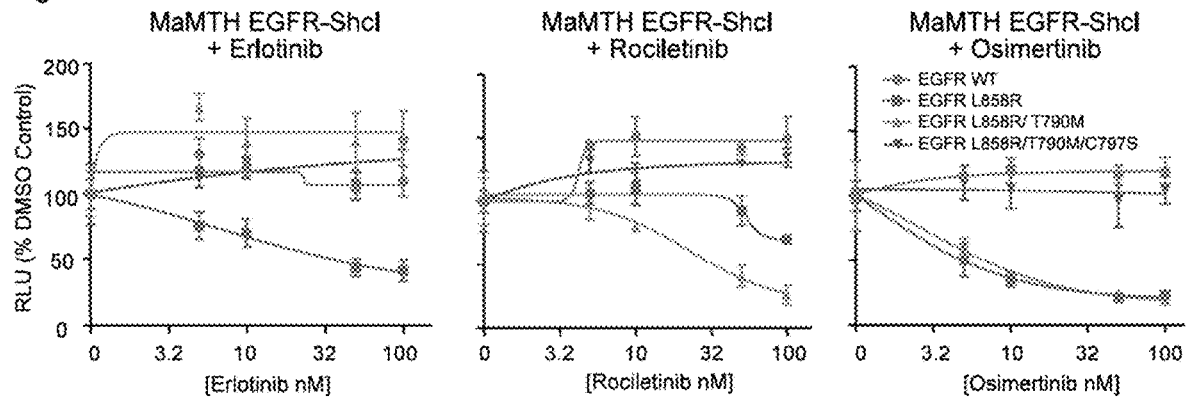

Fig. 8a
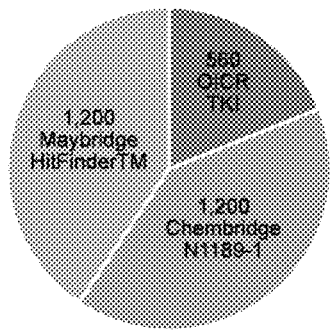
Fig. 8b
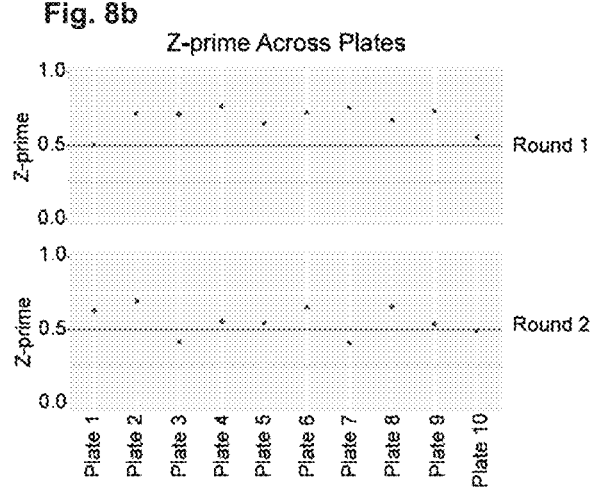
Fig. 8c
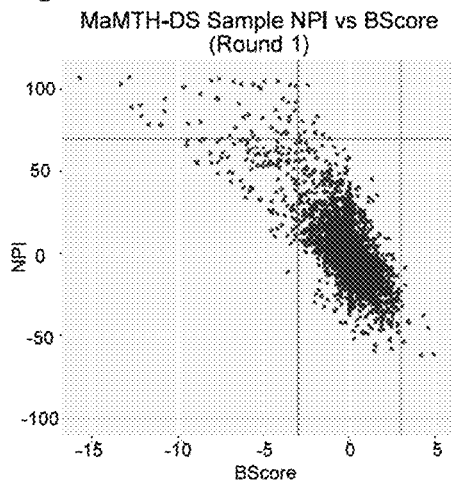
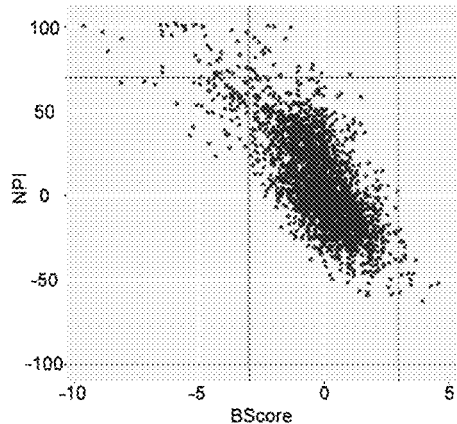
Fig. 8d
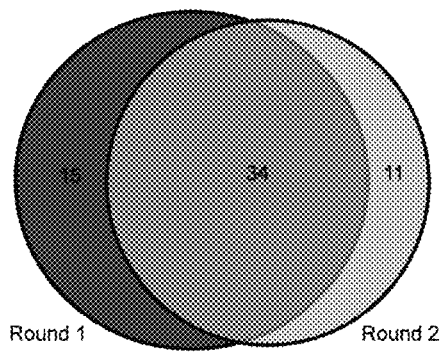
Fig. 8e
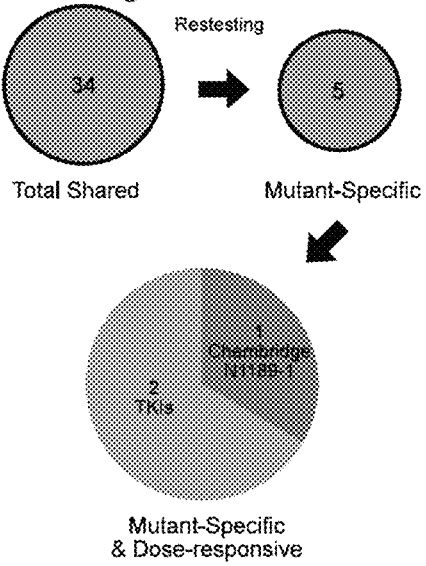

Fig. 10
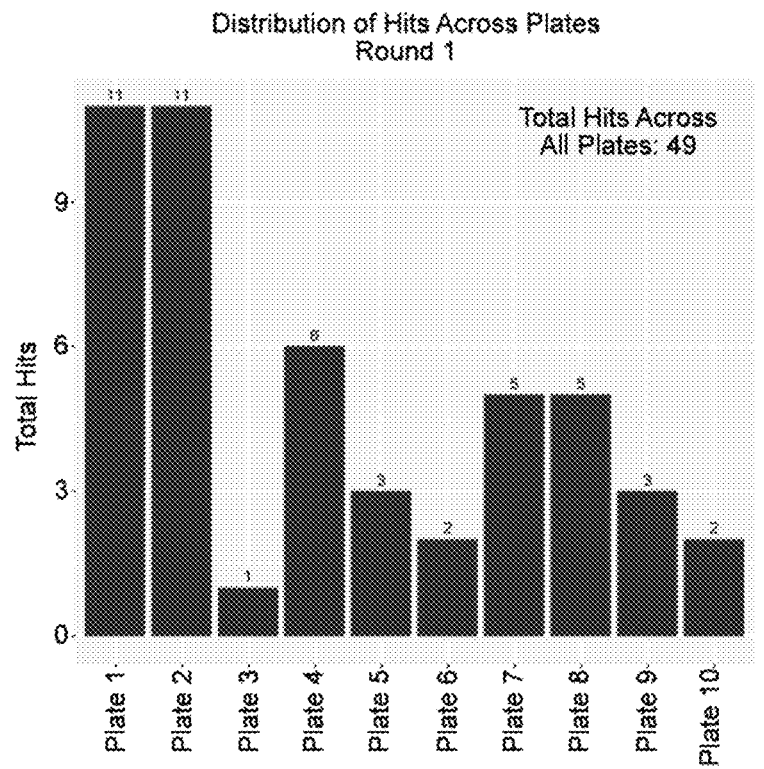
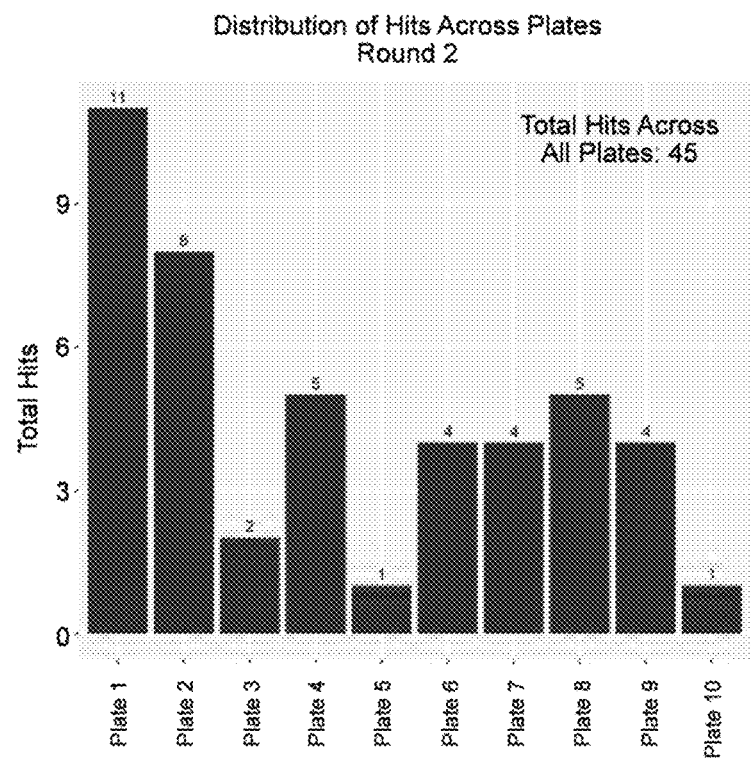

Fig. 21c
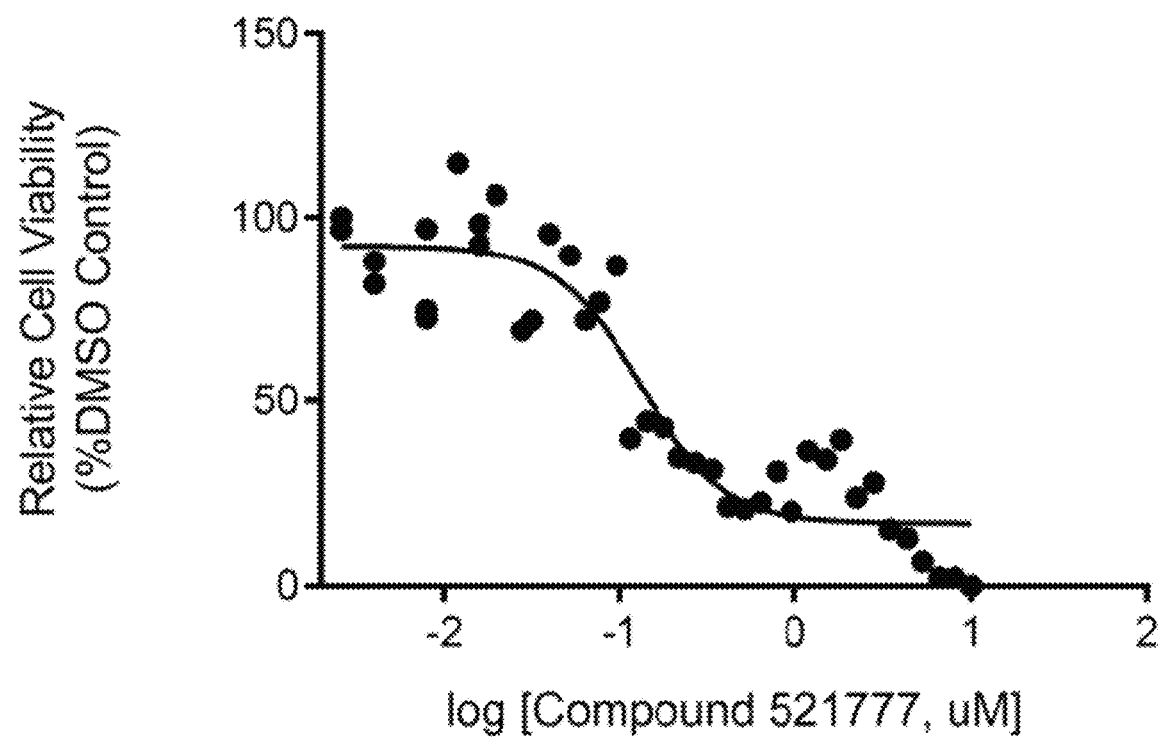
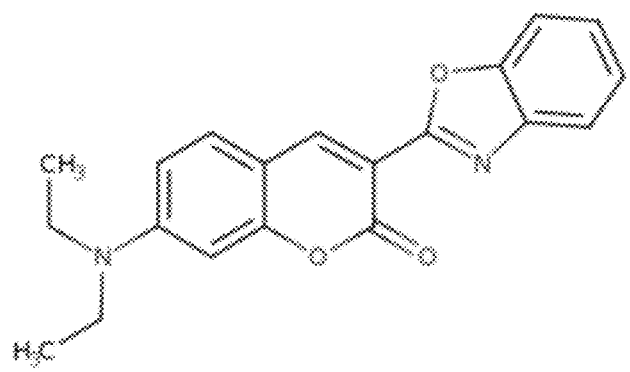

A benzoxazolyl-chromene compound

US 11,123,330 B2

METHODS AND COMPOSITIONS FOR INHIBITING MUTANT EGFR SIGNALING

This application claims the benefit of 35 USC 119 based on the priority of U.S. Provisional Application No. 62/564,599 filed Sep. 28, 2017, which is herein incorporated by reference.

FIELD

The disclosure relates to methods and compositions for inhibiting mutant EGFR signaling and in particular for inhibiting EGFR triple mutants comprising a C797 mutation.

BACKGROUND

Approximately half of EGFR-L858R and/or EGFR-ex-19del mutant non-small cell lung cancer (NSLC) patients treated with small molecule EGFR kinase inhibitors develop resistance associated with the EGF receptor EGFR-L858R-T790M or EGFR-ex19delT790M substitution. Indolocarbazole compounds have been identified as potent and reversible inhibitors of EGFR-L858R-T790M and EGFR-ex19delT790M that spare wild type EGFR [23].

EGFR mutations, including EGFR-exon 19 deletions and EGFR-L858R are the most frequent actionable genomic events in lung adenocarcinomas [24].

Tyrosinse kinase inhibitors (TKIs) such as osimertinib have been approved for and have been demonstrated to overcome EGFR-L858R-T790M and/or EGFR-ex19delT790M resistance. However C797S mutation present in EGFR triple mutants (C797S/T90M/activation mutation), induces resistance to osimertinib and other TKIs.

Currently, there are no effective therapeutic strategies to overcome the C797S/T90M/activation mutation (triple mutation)-mediated EGFR-TKI resistance. Brigatinib has been identified to be effective against triple mutation (C797S/T790M/activating-mutation) harbouring cells in preclinical models [18].

Additional treatment modalities are needed.

SUMMARY

A high throughout mammalian two hybrid screening platform, MaMTH-DS, identified compounds described herein that are, for example inhibitors of the kinase activities of Epidermal Growth Factor Receptor (EGFR) mutants. The compounds described herein may be useful as medicaments, for example for treating cancers with mutated EGFR such as drug resistant lung cancer comprising an EGFR C797 mutation, optionally a C797S mutation. Further, it is disclosed that the compounds show activity alone and in combination with therapeutic anti-EGFR antibodies.

Accordingly, an aspect of the disclosure includes a method of inhibiting activity of a mutant epidermal growth factor receptor (EGFR) in a cell comprising contacting the cell with a compound selected from 3-(1,3-benzoxazol-2-yl)-7-(diethylamino)-2H-chromen-2-one and a structurally related analog, salt or solvate thereof; midostaurin and a salt or solvate thereof; AZD7762 and a structurally related analog, salt or solvate thereof; and gilteritinib and a salt or solvate thereof; and mixtures thereof.

Another aspect includes a method of treating a subject afflicted with a lung cancer having a mutant EGFR, optionally having a C797 mutation, the method comprising administering to a subject in need thereof a therapeutically effective amount of a compound selected from 3-(1,3-benzoxazol-2-yl)-7-(diethylamino)-2H-chromen-2-one and a structurally related analog, salt or solvate thereof; midostaurin and a salt or solvate thereof; AZD7762 and a structurally related analog, salt or solvate thereof; and gilteritinib and a salt or solvate thereof; and mixtures thereof.

Yet another aspect includes, a composition comprising at least two compounds or a combination comprising at least two compounds selected from:

a compound of formula I and/or structurally related analog, salt or solvate thereof;
a compound of formula II, salt or solvate thereof;
a compound of formula III and a structurally related analog, salt or solvate thereof;
a compound of formula IV, salt or solvate thereof; and/or
an anti-EGFR therapeutic antibody.

Other features and advantages of the present application will become apparent from the following detailed description. It should be understood, however, that the detailed description and the specific examples while indicating embodiments of the application are given by way of illustration only, the scope of the claims should not be limited by the embodiments set forth in the examples, but should be given the broadest interpretation consistent with the description as a whole.

BRIEF DESCRIPTION OF THE DRAWINGS

An embodiment of the present disclosure will now be described in relation to the drawings in which:

FIG. 2a-e Effect of TKI therapeutics on the MaMTH-DS RTK signal. Panels show the effect of indicated compounds on MaMTH-DS activity in reporter cells stably expressing RTK bait in the presence of transiently transfected Shc1 prey. (a) MET receptor with Crizotinib and Erlotinib. (b) FGFR4 receptor with BLU9931 and Erlotinib. (c) AXL receptor with Foretinib and Erlotinib. (d) ALK receptor with Brigatinib and Erlotinib. (e) EGFR-WT and oncogenic mutants with Erlotinib, Rociletinib and Osimertinib.

FIG. 8a-e MaMTH-DS screening of EGFR L858R/T790M/C797S in the presence of Shc1. (a) Source and number of small molecules used in our pilot screening library. Library included compounds from the Maybridge HitFinder™, Chembridge N1189-1 and Ontario Institute for Cancer Research (OICR) TKI collections. (b) Z' values across all ten plates used in each round of screening. (c) Scatterplot of NPI vs BScore for all samples in screens. Horizontal red and green lines correspond to NPI values of 70% and −100%, respectively. Vertical red and green lines correspond to BScore values of −3 and +3, respectively. All values in the upper left quadrants were scored as hits. (d) Total hits and overlap for screening Rounds 1 and 2. (e) Total mutant-specific and dose-responsive compounds identified upon retesting of shared hits from Rounds 1 and 2 of screening.

FIG. 10 MaMTH-DS hits from screen of EGFR L858R/T790M/C797S in the presence of Shc1. Hit distributions across plates for Rounds 1 and 2 of screening are shown. The total number of hits per screen is labelled inset.

FIG. 21a-d Effect of 521377 on PC9 cells expressing EGFR C979S triple mutants. (a) 521377 inhibits cell viability of PC9 EGFR ex19del, PC9 EGFR ex19del/T790M and PC9 EGFR ex19del/T790M/C797S cells but not CFBE EGFR WT cells. (b) 521377, but not Osimertinib, activates caspase 3 and 7 activity in PC9 EGFR ex19del/T790M/C797S cells but not CBFE cells. (c) 521377 reduces the viability of PC9 EGFR ex19del/T790M/C797S organoids, (d) 521377 inhibits EGFR activation and downstream signaling in PC9 EGFR ex19del/T790M/C797S cells.

DETAILED DESCRIPTION

A. Definitions

Figure 1A:
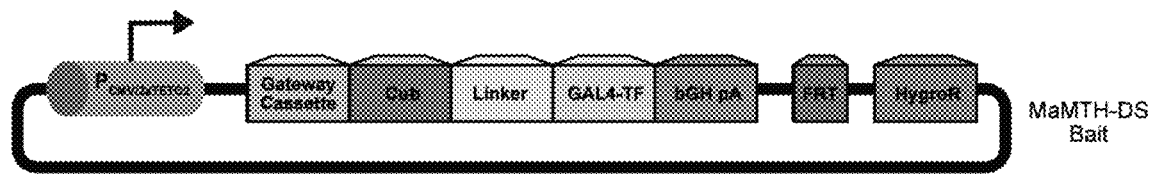
FIG. 1a-c Overview of key modifications employed in the MaMTH-DS platform. (a) Schematic diagram of FLP-In TREx compatible MaMTH-DS bait vector. (b) Methylene blue rinse test demonstrating enhanced adherence of FLP-compatible HEK293 cells carrying randomly integrated macrophage scavenger receptor 1 (MSR1, bottom panel) vs FLP-compatible HEK293 WT (top panel). (c) Comparison of Firefly vs *Gaussia princeps* luciferase activity across EGFR WT and mutants in MaMTH assays performed in a 384-well format. EGFR T790M=EGFR L858R/T790M, EGFR C797S=EGFR L858R/T790M/C797S.

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "compound(s) of the disclosure" or "compound(s) of the present disclosure" and the like as used herein means compounds of formula I and structurally related analogs, or a pharmaceutically acceptable salt or solvate thereof, compounds of formula II, or a pharmaceutically acceptable salt or solvate thereof, compounds of formula III and structurally related analogs, or a pharmaceutically acceptable salt or solvate thereof, and compounds of formula IV, or a pharmaceutically acceptable salt or solvate thereof, and includes tautomers, regioisomers, geometric isomers, and where applicable, stereoisomers, including optical isomers (racemic mixtures, enantiomers, or enantiomerically enriched mixtures) and other stereoisomers (diastereomers) thereof.

The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt or a base addition salt which is suitable for, or compatible with, the treatment of subjects.

An acid addition salt which is suitable for, or compatible with, the treatment of subjects as used herein means any non-toxic organic or inorganic salt of any basic compound. Basic compounds that form an acid addition salt include, for example, compounds comprising an amine group. Illustrative inorganic acids which form suitable salts include hydrochloric, hydrotrifluoroacetic, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono- or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art. In an embodiment, the acid addition salt is a hydrochloride or hydrotrifluoroacetic acid salt.

A base addition salt which is suitable for, or compatible with, the treatment of subjects as used herein means any non-toxic organic or inorganic base addition salt of any acidic compound. Acidic compounds that form a base addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

The term "dosage form" as used herein refers to the physical form of a dose for example comprising a desired compound of the disclosure, and includes without limitation injectable dosage forms, including, for example, sterile solutions and sterile powders for reconstitution, and the like, that are suitably formulated for injection, liquid and solid dosage forms including, for example tablets, including enteric coated tablets, caplets, gelcaps, capsules, ingestible tablets, buccal tablets, troches, elixirs, suspensions, syrups, wafers, resuspendable powders, liquids and solutions.

The term "diluent" as used herein refers to a pharmaceutically acceptable carrier which does not inhibit a physiological activity or property of an active compound to be administered and does not irritate the subject and does not abrogate the biological activity and properties of the administered compound. Diluents include any and all solvents, dispersion media, coatings, surfactants, antioxidants, preservative salts, preservatives, binders, excipients, disintegration agents, lubricants, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with drug resistant lung cancer can be treated to prevent progression, or alternatively a subject in remission can be treated with a compound or composition described herein to prevent recurrence. Treatment methods comprise administering to a subject a therapeutically effective amount of one or more of the compounds of the disclosure and optionally, consists of a single administration, or alternatively comprises a series of administrations. For example, the compounds are administered to the subject in an amount and for a duration sufficient to treat the patient.

The term "drug resistant lung cancer" means a lung cancer that has at least one drug resistance mutation, optionally two drug resistance mutations, such as EGFR triple mutants comprising C797S/T790M mutations and/or a lung cancer that has progressed in a subject on at least 1 EGFR inhibitor.

As used herein, the term "effective amount" or "therapeutically effective amount" means an amount effective, at dosages and for periods of time necessary to achieve the desired result. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

The term "mixture" as used herein refers to a composition comprising two or more compounds, salts or solvates. The term combination includes two or more compounds or two or more compositions each comprising one or more compounds, salts or solvates thereof including mixtures of any of the foregoing.

The term "triple mutant EGFR" as used herein means EGFR comprising an activating mutation such as ex19del or L858R and the resistance mutations at T790 (e.g. T790M) and C797 (e.g. C797S) and in particular to one of EGFR-ex19del/T790M/C797S and EGFR-L858R/T790M/C797S mutants.

The term "administered" as used herein means administration of a therapeutically effective dose of a compound or composition of the application to a cell either in cell culture or in a patient (i.e. subject) by any means of administration suitable.

The term "in combination" or "combination therapy" as used herein means that at least two compounds or compositions are administered to the patient as part of a treatment regimen, administered for example contemporaneously, sequentially and/or in alternating fashion, optionally such that effective amounts or concentrations of each of the two or more compounds may be found in the patient at a given point in time. Although compounds according to the present disclosure may be co-administered to a patient at the same time, the term embraces both administration of two or more compounds of the disclosure at the same time or at different times and encompasses where the effective concentrations of all coadministered compounds or compositions are found in the subject at a given time.

The term "non-small cell lung cancer" as used herein includes adenocarcinomas, squamous cell carcinomas, large cell carcinomas, adenosquamous carcinoma and sarcomatoid carcinoma.

The term "mutant epidermal growth factor receptor (EGFR)" as used herein means an EGFR having at least one activating mutation associated with disease. The mutant EGFR can also comprise additional mutations, including drug resistance mutations such as T790M and/or C797S.

The term "3-(1,3-benzoxazol-2-yl)-7-(diethylamino)-2H-chromen-2-one and structurally related analogs thereof" as used herein refers to a the compound of formula (I):

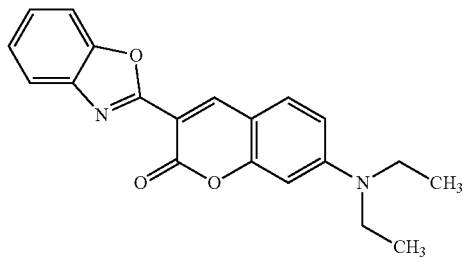

and structurally related analogs thereof including benzoxazolyl and/or chromenone containing compounds, substituted versions thereof or a salt or solvate of any of the foregoing as well as mixtures thereof, hereinafter: "Compound of formula I and structurally related analogs thereof". Reference to a compound of formula I and/or a structurally related analog thereof thereby refers to one of a compound of formula I, a structurally related analog thereof, a salt of any of the foregoing and/or a mixture of any of the foregoing. The structurally related analogs contemplated include or are molecules sharing the same backbone and which can inhibit mutant EGFR, preferably triple mutant EGFR comprising mutation of C797, interaction with Shc1. This compound is alternatively referred to by as 3-(1,3-benzoxazol-2-yl)-7-(diethylamino)-2H-chromen-2-one, Chembridge 5213777, Compound 5213777, and 5213777. Also structure analogs include halogen derivatives on the benzoxazolyl moiety of compound 3-(1,3-benzoxazol-2-yl)-7-(diethylamino)-2H-chromen-2-one, for example chlorinated derivatives thereof such as 3-(5-chloro-1,3-benzoxazol-2-yl)-7-(diethylamino)-2H-chromen-2-one, also referred as to CAS #35773-43-4, MolPort-002-557-047, or Disperse Yellow 232, which is available from a number of vendors including AK Scientific Inc.

Derivatives of chromen-2-one are described in US 20060122387 and are incorporated herein by reference, including the ones mentioned below.

| 1 | 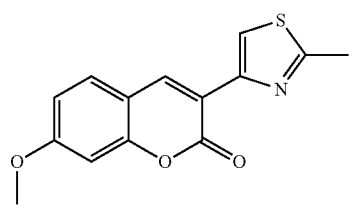 [SMILES: COc1ccc2cc(-c3csc(C)n3)c(=O)oc2c1] | 7-Methoxy-3-(2-methyl-thiazol-4-yl)-chro-men-2-one |
| 2 | 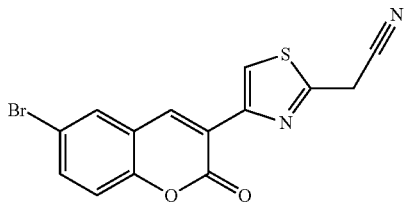 [SMILES: N#CCc1nc(-c2cc3cc(Br)ccc3oc2=O)cs1] | [4-(6-Bromo-2-oxo-2H-chromen-3-yl)-thia-zol-2-yl]-acetonitrile |
| 3 | 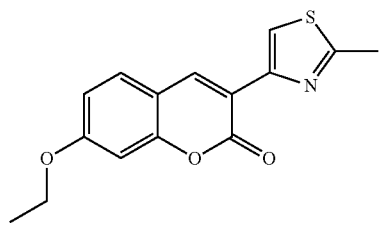 [SMILES: CCOc1ccc2cc(-c3csc(C)n3)c(=O)oc2c1] | 7-Ethoxy-3-(2-methyl-thiazol-4-yl)-chro-men-2-one |
| 4 | 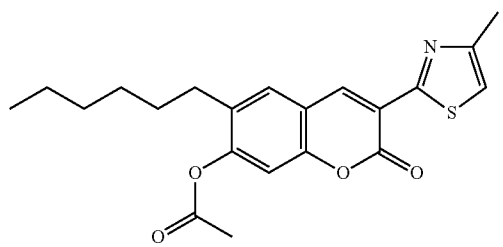 [SMILES: CCCCCCc1cc2cc(-c3nc(C)cs3)c(=O)oc2cc1OC(C)=O] | Acetic acid 6-hexyl-3-(4-methyl-thia-zol-2-yl)-2-oxo-2H-chromen-7-yl ester |

| | | |
|---|---|---|
| 5 | 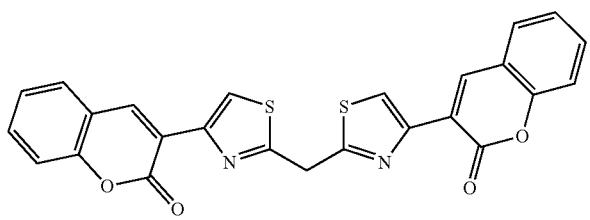 [SMILES: O=c1oc2ccccc2cc1-c1csc(Cc2nc(-c3cc4ccccc4oc3=O)cs2)n1] | 3-(2-[4-(Chromen-2-one-3-yl)tiazol-2-yl]thia-zol-4-yl)-chromen-2-one |
| 6 | 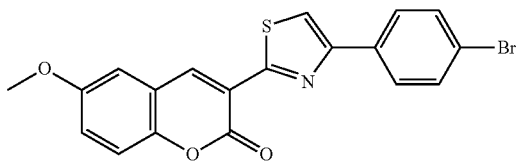 [SMILES: COc1ccc2oc(=O)c(-c3nc(-c4ccc(Br)cc4)cs3)cc2c1] | 7-Methoxy-3-(2-methyl-thiazol-4-yl)-chro-men-2-one |
| 7 | 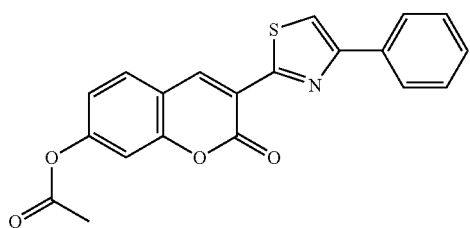 [SMILES: CC(=O)Oc1ccc2cc(-c3nc(-c4ccccc4)cs3)c(=O)oc2c1] | Acetic acid 2-oxo-3-(4-phenyl-thia-zol-2-yl)-2H-chromen-7-yl ester |
| 8 |  | 7-Hydroxy-3-(2-phenyl-thiazol-4-yl)-chro-men-2-one |
| 9 | 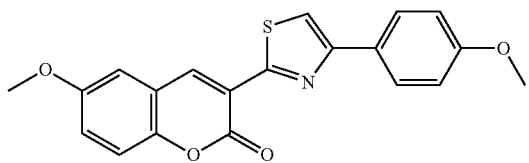 | 6-Methoxy-3-[4-(4-methoxy-phenyl)-thia-zol-2-yl]-chromen-2-one |
| 10 | 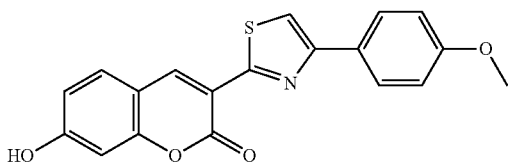 [SMILES: COc1ccc(-c2csc(-c3cc4ccc(O)cc4oc3=O)n2)cc1] | 7-Hydroxy-3-[4-(4-methoxy-phenyl)-thia-zol-2-yl]-chromen-2-one |
| 11 | 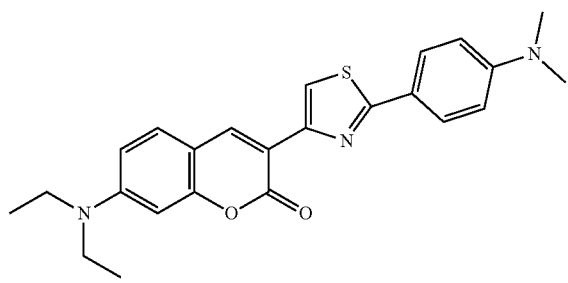 [SMILES: CCN(CC)c1ccc2cc(-c3csc(-c4ccc(N(C)C)cc4)n3)c(=O)oc2c1] | 7-Diethylamino-3-[2-(4-dimethylamino-phenyl)-thiazol-4-yl]-chromen-2-one |

-continued

| | | |
|---|---|---|
| 12 | 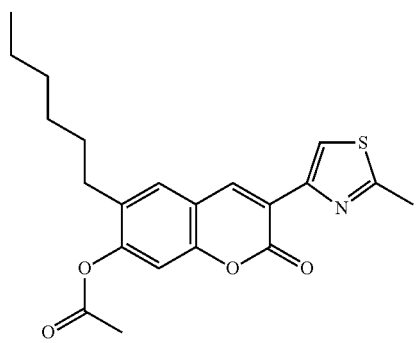 [SMILES: CCCCCCc1cc2cc(-c3csc(C)n3)c(=O)oc2cc1OC(C)=O] | Acetic acid 6-hexyl-3-(2-methyl-thiazol-4-yl)-2-oxo-2H-chromen-7-yl ester |
| 13 | 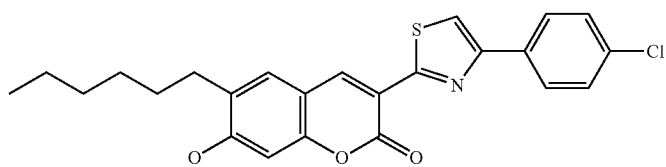 [SMILES: CCCCCCc1cc2cc(-c3nc(-c4ccc(Cl)cc4)cs3)c(=O)oc2cc1O] | 3-[4-(4-Chloro-phenyl)-thiazol-2-yl]-6-hex-yl-7-hydroxy-chromen-2-one |
| 14 | 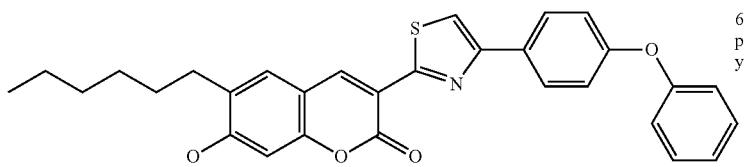 | 6-Hexyl-7-hydroxy-3-[4-(4-phenoxy-phe-nyl)-thiazol-2-yl]-chromen-2-one |
| 15 | 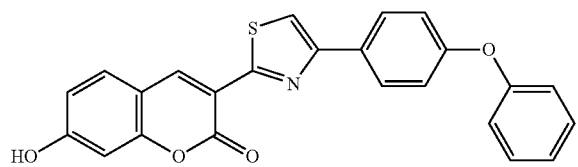 [SMILES: O=c1oc2cc(O)ccc2cc1-c1nc(-c2ccc(Oc3ccccc3)cc2)cs1] | 7-Hydroxy-3-[4-(4-phenoxy-phenyl)-thia-zol-2-yl]-chromen-2-one |
| 16 | 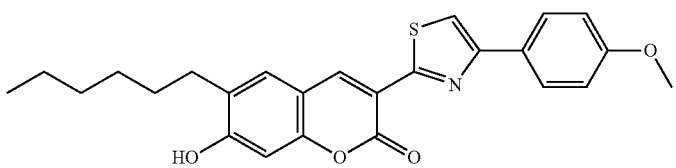 [SMILES: CCCCCCc1cc2cc(-c3nc(-c4ccc(OC)cc4)cs3)c(=O)oc2cc1O] | 6-Hexyl-7-hydroxy-3-[4-(4-methoxy-phe-nyl)-thiazol-2-yl]-chromen-2-one |
| 17 | 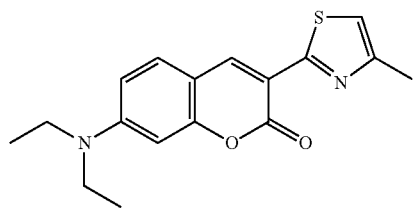 [SMILES: CCN(CC)c1ccc2cc(-c3nc(C)cs3)c(=O)oc2c1] | 7-Diethylamino-3-(4-methyl-thiazol-2-yl)-chro-men-2-one |
| 18 | 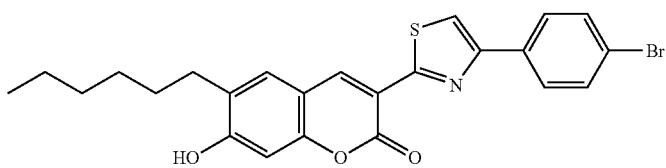 [SMILES: CCCCCCc1cc2cc(-c3nc(-c4ccc(Br)cc4)cs3)c(=O)oc2cc1O] | 3-[4-(4-Bromo-phenyl)-thiazol-2-yl]-6-hex-yl-7-hydroxy-chromen-2-one |

-continued

| | | |
|---|---|---|
| 19 | 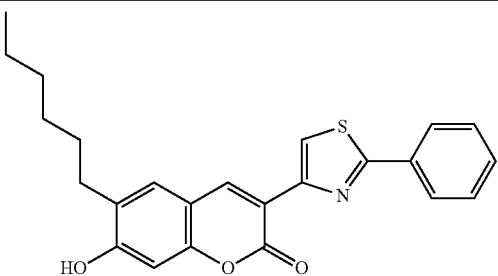 | 6-Hexyl-7-hydroxy-3-(2-phenyl-thia-zol-4-yl)-chromen-2-one |
| 20 | 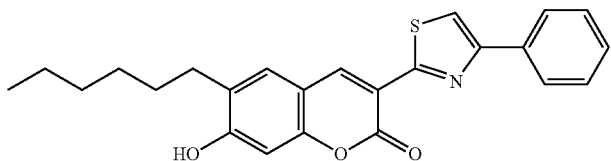 [SMILES: CCCCCCc1cc2cc(-c3nc(-c4ccccc4)cs3)c(=O)oc2cc1O] | 6-Hexyl-7-hydroxy-3-(4-phenyl-thiazol-2-yl)-chromen-2-one |
| 21 | 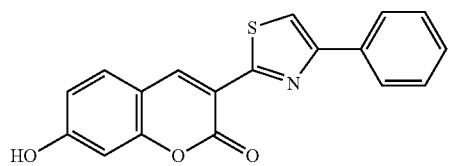 [SMILES: O=c1oc2cc(O)ccc2cc1-c1nc(-c2ccccc2)cs1] | 7-Hydroxy-3-(4-phenyl-thiazol-2-yl)-chro-men-2-one |
| 22 | 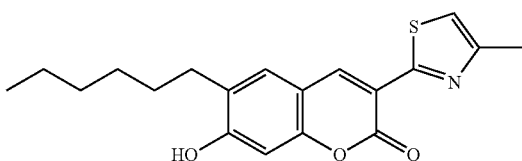 [SMILES: CCCCCCc1cc2cc(-c3nc(C)cs3)c(=O)oc2cc1O] | 6-Hexyl-7-hydroxy-3-(4-methyl-thiazol-2-yl)-chromen-2-one |
| 23 | 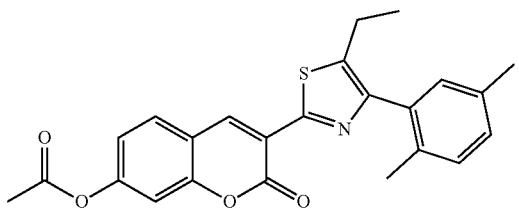 [SMILES: CCc1sc(-c2cc3ccc(OC(C)=O)cc3oc2=O)nc1-c1cc(C)ccc1C] | Acetic acid 3-[4-(2,5-dimethyl-phe-nyl)-5-ethyl-thiazol-2-yl]-2-oxo-2H-chro-men-7-yl ester |
| 24 | 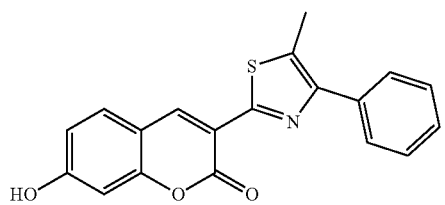 [SMILES: Cc1sc(-c2cc3ccc(O)cc3oc2=O)nc1-c1ccccc1] | 7-Hydroxy-3-(5-methyl-4-phenyl-thiazol-2-yl)-chromen-2-one |
| 25 | 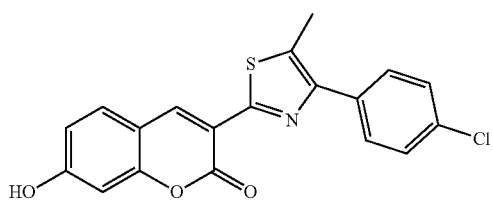 [SMILES: Cc1sc(-c2cc3ccc(O)cc3oc2=O)nc1-c1ccc(Cl)cc1] | 3-[4-(4-Chloro-4-phenyl)-5-methyl-thiazol-2-yl]-7-hydroxy-chromen-2-one |
| 26 | 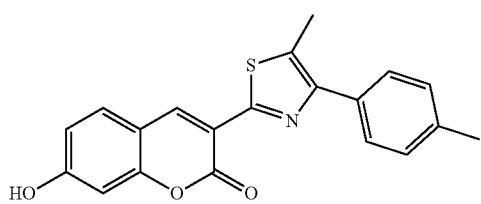 [SMILES: Cc1ccc(-c2nc(-c3cc4ccc(O)cc4oc3=O)sc2C)cc1] | 7-Hydroxy-3-(5-methyl-4-p-tolyl-thiazol-2-yl)-chromen-2-one |

| | | |
|---|---|---|
| 27 | 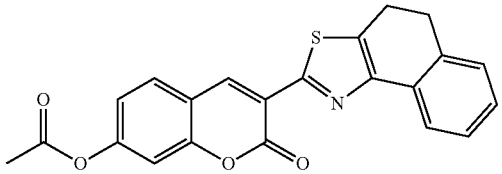 [SMILES: CC(=O)Oc1ccc2cc(-c3nc4c(s3)CCc3ccccc3-4)c(=O)oc2c1] | Acetic acid 3-(4,5-dihydro-naphtho[1,2-d]thia-zol-2-yl)-2-oxo-2H-chromen-7-yl ester |
| 28 |  | Acetic acid 2-oxo-3-[4-(5,6,7,8-tetra-hydro-naphthalen-2-yl)-thiazol-2-yl]-2H-chro-men-7-yl ester |
| 29 | 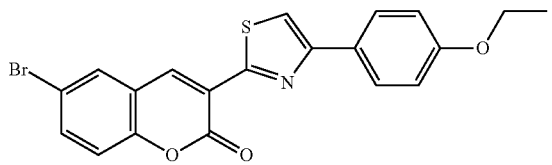 [SMILES: CCOc1ccc(-c2csc(-c3cc4cc(Br)ccc4oc3=O)n2)cc1] | 6-Bromo-3-[4-(4-ethoxy-phenyl)-thia-zol-2-yl]-chromen-2-one |
| 30 | 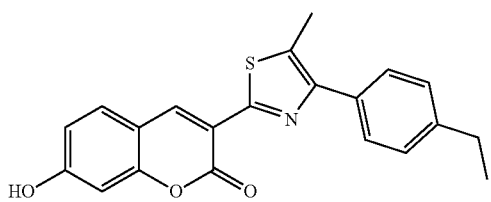 [SMILES: CCc1ccc(-c2nc(-c3cc4ccc(O)cc4oc3=O)sc2C)cc1] | 3-[4-(4-Ethyl-phenyl)-5-methyl-thiazol-2-yl]-7-hydroxy-chromen-2-one |
| 31 | 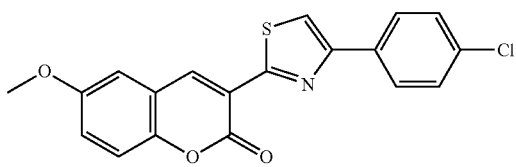 [SMILES: COc1ccc2oc(=O)c(-c3nc(-c4ccc(Cl)cc4)cs3)cc2c1] | 3-[4-(4-Chloro-phenyl)-thiazol-2-yl]-6-meth-oxy-chromen-2-one |
| 32 | 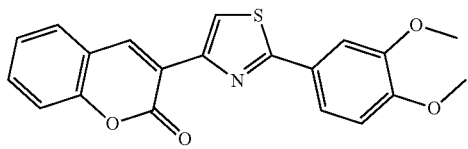 [SMILES: COc1ccc(-c2nc(-c3cc4ccccc4oc3=O)cs2)cc1OC] | 3-[2-(3,4-Dimethoxy-phenyl)-thiazol-4-yl]-chro-men-2-one |
| 33 | 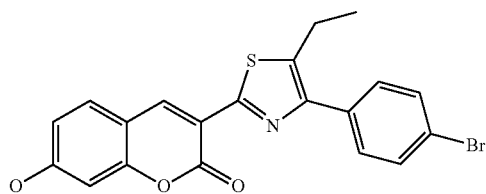 [SMILES: CCc1sc(-c2cc3ccc(O)cc3oc2=O)nc1-c1ccc(Br)cc1] | 3-[4-(4-Bromo-phenyl)-5-ethyl-thiazol-2-yl]-7-hydroxy-chromen-2-one |
| 34 | 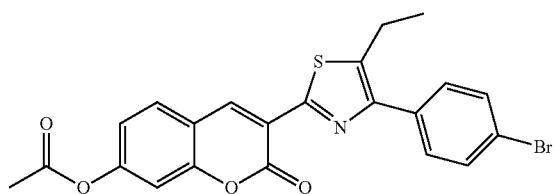 [SMILES: CCc1sc(-c2cc3ccc(OC(C)=O)cc3oc2=O)nc1-c1ccc(Br)cc1] | Acetic acid 3-[4-(4-bromo-phenyl)-5-eth-yl-thiazol-2-yl]-2-oxo-2H-chro-men-7-yl ester |

| | | |
|---|---|---|
| 35 | 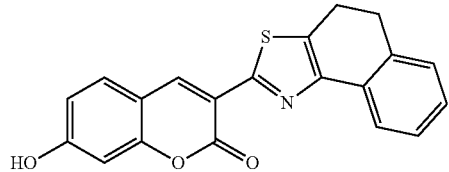 [SMILES: O=c1oc2cc(O)ccc2cc1-c1nc2c(s1)CCc1ccccc1-2] | 3-(4,5-Dihydro-naphtho[1,2-d]thiazol-2-yl)-7-hy-droxy-chromen-2-one |
| 36 | 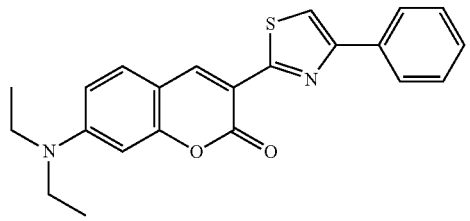 [SMILES: CCN(CC)c1ccc2cc(-c3nc(-c4ccccc4)cs3)c(=O)oc2c1] | 7-Diethylamino-3-(4-phenyl-thiazol-2-yl)-chro-men-2-one |
| 37 | 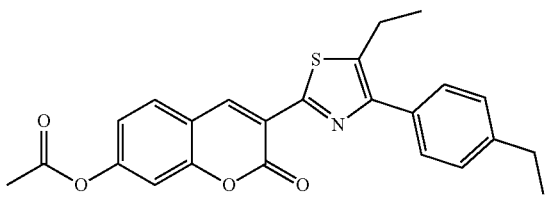 [SMILES: CCc1ccc(-c2nc(-c3cc4ccc(OC(C)=O)cc4oc3=O)sc2CC)cc1] | Acetic acid 3-[5-ethyl-4-(4-ethyl-phe-nyl)-thiazol-2-yl]-2-oxo-2H-chro-men-7-yl ester |
| 38 | 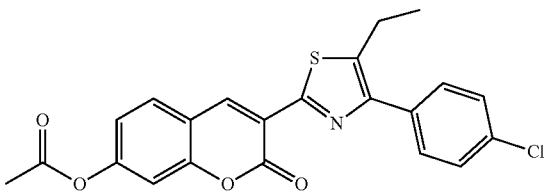 [SMILES: CCc1sc(-c2cc3ccc(OC(C)=O)cc3oc2=O)nc1-c1ccc(Cl)cc1] | Acetic acid 3-[4-(4-chloro-phenyl)-5-eth-yl-thiazol-2-yl]-2-oxo-2H-chro-men-7-yl ester |
| 39 | 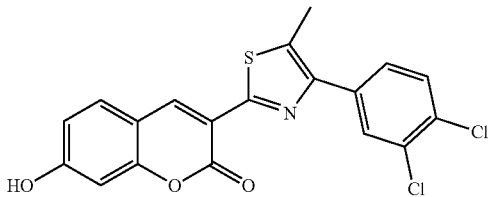 [SMILES: Cc1sc(-c2cc3ccc(O)cc3oc2=O)nc1-c1ccc(Cl)c(Cl)c1] | 3-[4-(3,4-Dichloro-phenyl)-5-methyl-thiazol-2-yl]-7-hydroxy-chromen-2-one |
| 40 | 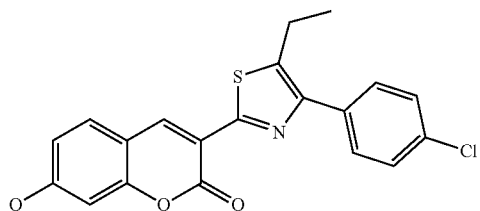 [SMILES: CCc1sc(-c2cc3ccc(O)cc3oc2=O)nc1-c1ccc(Cl)cc1] | 3-[4-(4-Chloro-phenyl)-5-ethyl-thia-zol-2-yl]-7-hydroxy-chromen-2-one |
| 41 | 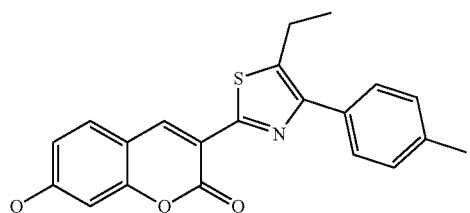 [SMILES: CCc1sc(-c2cc3ccc(O)cc3oc2=O)nc1-c1ccc(C)cc1] | 3-(5-Ethyl-4-p-tolyl-thiazol-2-yl)-7-hy-droxy-chromen-2-one |

-continued
| | | |
|---|---|---|
| 42 | 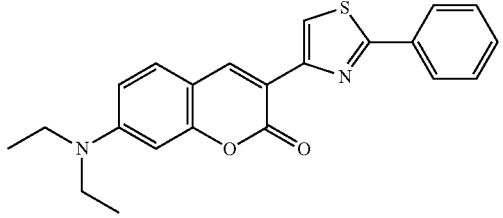 [SMILES: CCN(CC)c1ccc2cc(-c3csc(-c4ccccc4)n3)c(=O)oc2c1] | 7-Diethylamino-3-(2-phenyl-thiazol-4-yl)-chro-men-2-one |
| 43 | 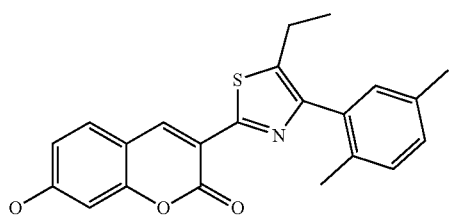 [SMILES: CCc1sc(-c2cc3ccc(O)cc3oc2=O)nc1-c1cc(C)ccc1C] | 3-[4-(2,5-Dimethyl-phenyl)-5-ethyl-thiazol-2-yl]-7-hydroxy-chromen-2-one |
| 44 | 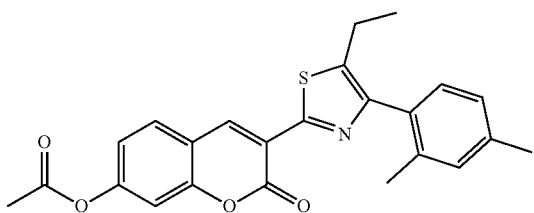 [SMILES: CCc1sc(-c2cc3ccc(OC(C)=O)cc3oc2=O)nc1-c1ccc(C)cc1C] | Acetic acid 3-[4-(2,4-dimethyl-phenyl)-5-ethyl-thiazol-2-yl]-2-oxo-2H-chro-men-7-yl ester |
| 45 | 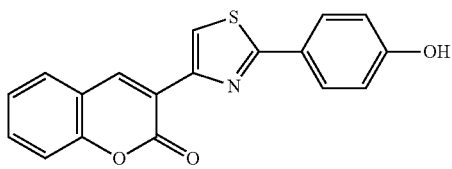 [SMILES: O=c1oc2ccccc2cc1-c1csc(-c2ccc(O)cc2)n1] | 3-[2-(4-Hydroxy-phenyl)-thiazol-4-yl]-chro-men-2-one |
| 46 | 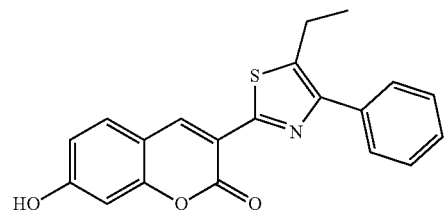 [SMILES: CCc1sc(-c2cc3ccc(O)cc3oc2=O)nc1-c1ccccc1] | 3-(5-Ethyl-4-phenyl-thiazol-2-yl)-7-hy-droxy-chromen-2-one |
| 47 | 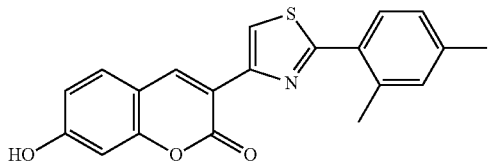 [SMILES: Cc1ccc(-c2nc(-c3cc4ccc(O)cc4oc3=O)cs2)c(C)c1] | 3-[2-(2,4-Dimethyl-phenyl)-thiazol-4-yl]-7-hy-droxy-chromen-2-one |
| 48 | 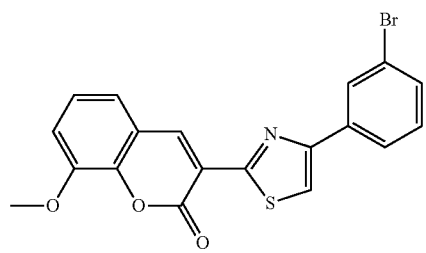 [SMILES: COc1cccc2cc(-c3nc(-c4cccc(Br)c4)cs3)c(=O)oc12] | 3-[4-(3-Bromo-phenyl)-thiazol-2-yl]-8-meth-oxy-chromen-2-one |

-continued
| | | |
|---|---|---|
| 49 | 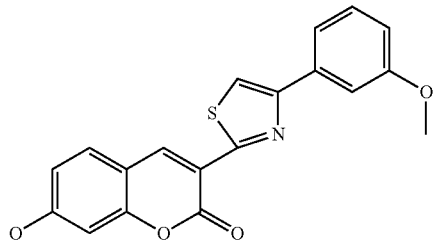 [SMILES: COc1cccc(-c2csc(-c3cc4ccc(O)cc4oc3=O)n2)c1] | 7-Hydroxy-3-[4-(3-methoxy-phenyl)-thia-zol-2-yl]-chromen-2-one |
| 50 | 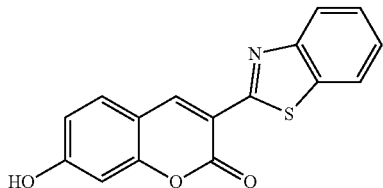 [SMILES: O=c1oc2cc(O)ccc2cc1-c1nc2ccccc2s1] | 3-Benzothiazol-2-yl-7-hydroxy-chro-men-2-one |
| 51 | 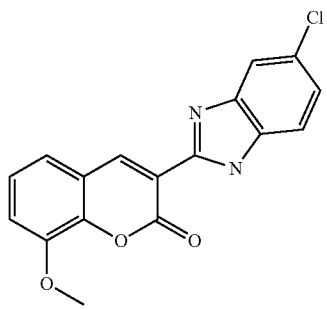 [SMILES: COc1cccc2cc(-c3nc4cc(Cl)ccc4[nH]3)c(=O)oc12] | 3-(5-Chloro-1H-benzoimidazol-2-yl)-8-meth-oxy-chromen-2-one |
| 52 | 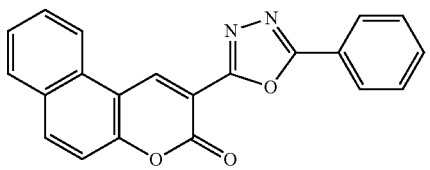 [SMILES: O=c1oc2ccc3ccccc3c2cc1-c1nnc(-c2ccccc2)o1] | 2-(5-Phenyl-[1,3,4]oxadiazol-2-yl)-ben-zo+f+chromen-3-one |
| 53 | 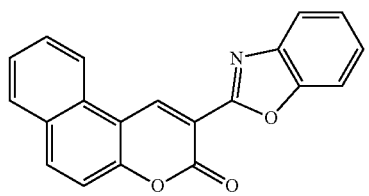 [SMILES: O=c1oc2ccc3ccccc3c2cc1-c1nc2ccccc2o1] | 2-Benzooxazol-2-yl-benzo[f]chromen-3-one |
| 54 | 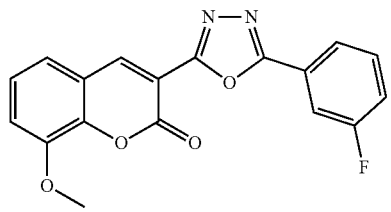 [SMILES: COc1cccc2cc(-c3nnc(-c4cccc(F)c4)o3)c(=O)oc12] | 3-[5-(3-Fluoro-phenyl)-[1,3,4]oxa-diazol-2-yl]-8-methoxy-chromen-2-one |
| 55 | 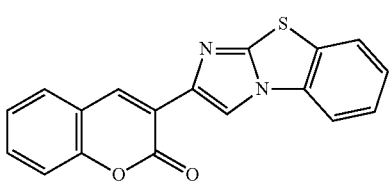 [SMILES: O=c1oc2ccccc2cc1-c1cn2c(n1)sc1ccccc12] | 3-Benzo[d]imidazo[2,1-b]thiazol-2-yl]-chro-men-2-one |

| | | |
|---|---|---|
| 56 | 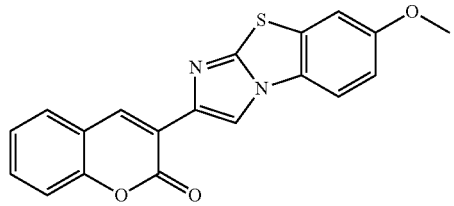 [SMILES: COc1ccc2c(c1)sc1nc(-c3cc4ccccc4oc3=O)cn12] | 3-(7-Methoxy-benzo[d]imidazo[2,1-b]thia-zol-2-yl)-chromen-2-one |
| 57 | 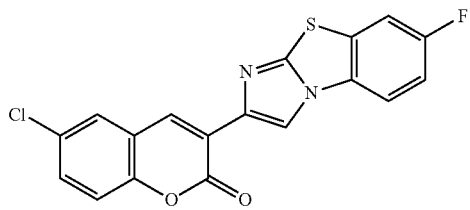 [SMILES: O=c1oc2ccc(Cl)cc2cc1-c1cn2c(n1)sc1cc(F)ccc12] | 6-Chloro-3-(7-fluoro-benzo[d]imi-dazo[2,1-b]thiazol-2-yl)-chromen-2- |
| 58 | 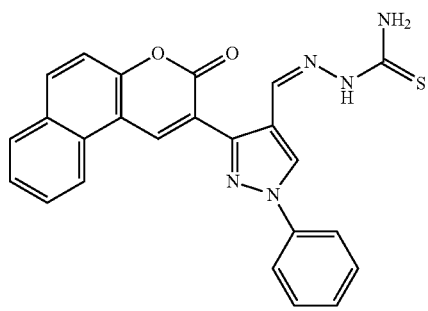 [SMILES: NC(=S)N/N=C\c1cn(-c2ccccc2)nc1-c1cc2c(ccc3ccccc32)oc1=O] | 2-(4-Thiosemicarbazidomethyl-1-phe-nyl-1H-pyrazol-3-yl)-benzo[f]chromen-3-one |
| 59 | 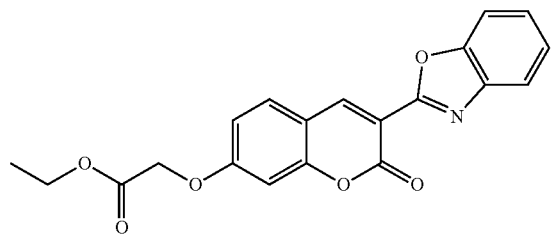 [SMILES: CCOC(=O)COc1ccc2cc(-c3nc4ccccc4o3)c(=O)oc2c1] | (3-Benzooxazol-2-yl-2-oxo-2H-chro-men-7-yloxy)-acetic acid ethyl ester |
| 60 | 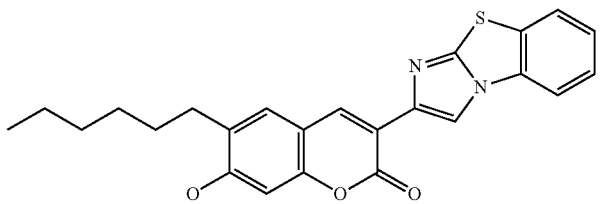 [SMILES: CCCCCCc1cc2cc(-c3cn4c(n3)sc3ccccc34)c(=O)oc2cc1O] | 3-Benzo[d]imidazo[2,1-b]thiazol-2-yl-6-hex-yl-7-hydroxy-chromen-2-one |
| 61 | 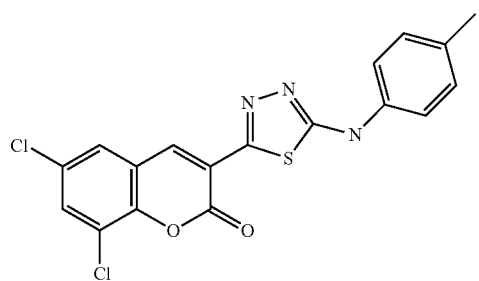 [SMILES: Cc1ccc(Nc2nnc(-c3cc4cc(Cl)cc(Cl)c4oc3=O)s2)cc1] | 6,8-Dichloro-3-(5-p-tolylamino-[1,3,4]thia-diazol-2-yl)-chromen-2-one |

-continued
| | | |
|---|---|---|
| 62 | 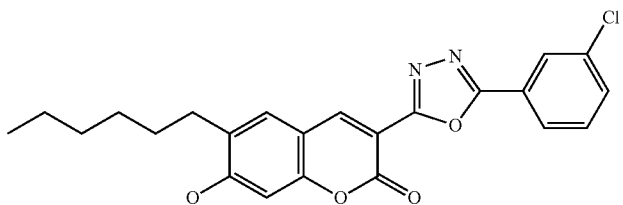 [SMILES: CCCCCCc1cc2cc(-c3nnc(-c4cccc(Cl)c4)o3)c(=O)oc2cc1O] | 3-[5-(3-Chloro-phenyl)-[1,3,4]oxa-diazol-2-yl]-6-hexyl-7-hydroxy-chro-men-2-one |
| 63 | 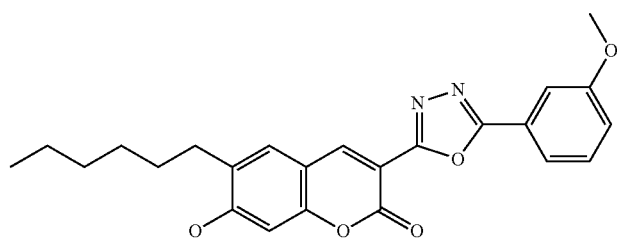 [SMILES: CCCCCCc1cc2cc(-c3nnc(-c4cccc(OC)c4)o3)c(=O)oc2cc1O] | 6-Hexyl-7-hydroxy-3-[5-(3-methoxy-phe-nyl)-[1,3,4]oxadiazol-2-yl]-chro-men-2-one |
| 64 | 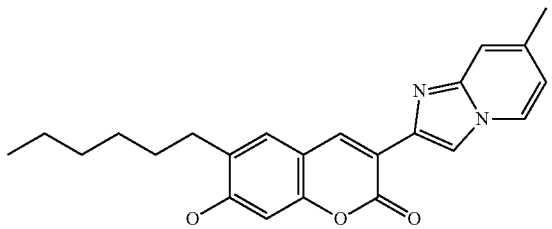 [SMILES: CCCCCCc1cc2cc(-c3cn4ccc(C)cc4n3)c(=O)oc2cc1O] | 6-Hexyl-7-hydroxy-3-(7-methyl-imidazo[1,2-a]pyridin-2-yl)-chromen-2-one |
| 65 | 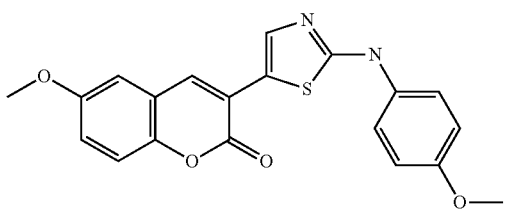 | 6-Methoxy-3-[2-(4-methoxy-phenyl-amino)-thiazol-5-yl]-chromen-2-one |
| 66 | 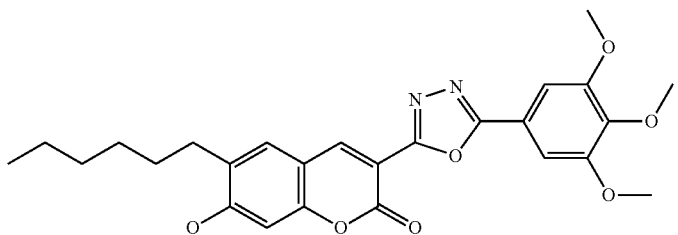 [SMILES: CCCCCCc1cc2cc(-c3nnc(-c4cc(OC)c(OC)c(OC)c4)o3)c(=O)oc2cc1O] | 6-Hexyl-7-hydroxy-3-[5-(3,4,5-trimeth-oxy-phenyl)-[1,3,4]oxadiazol-2-yl]-chro-men-2-one |

3-(1,3-benzoxazol-2-yl)-7-(diethylamino)-2H-chromen-2-one is compound 5213777 of the Chembridge Diverset library (e.g. N1189-1) of compounds and can be purchased from ChemBridge Online Chemical Store: https://www.hit2lead.com/.

"Midostaurin" as used herein refers to N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide of the formula (II):

(II)

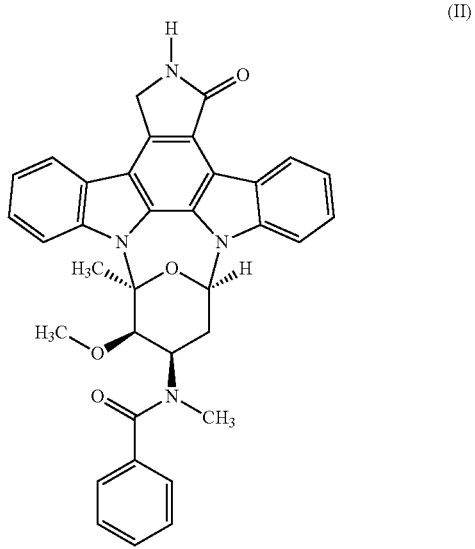 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4]

or a salt or solvate thereof, hereinafter: "Compound of formula II or midostaurin".

Midostaurin is also known as 4-N-benzoyl staurosporine, Benzoylstaurosporine, CGP 41251, N-benzoyl-staurosporine, PKC412, PKC412A, and Rydapt™ and is a derivative of the naturally occurring alkaloid staurosporine. It has been specifically described in the European patent No. 0 296 110 published on Dec. 21, 1988, as well as in U.S. Pat. No. 5,093,330 published on Mar. 3, 1992, and Japanese Patent No. 2 708 047. Midostaurin described in these documents are incorporated into the present application by reference. Midostaurin is a compound in the OICR TKI library with identifier OICR0000317A01. Midostaurin is available from a number of vendors including Sigma-Aldrich. Midostaurin and its manufacturing process have been described.

The term "AZD7762" as used herein refers 3-(carbamoylamino)-5-(3-fluorophenyl)-N-[(3S)-piperidin-3-yl]thiophene-2-carboxamide of the formula (III):

(III)

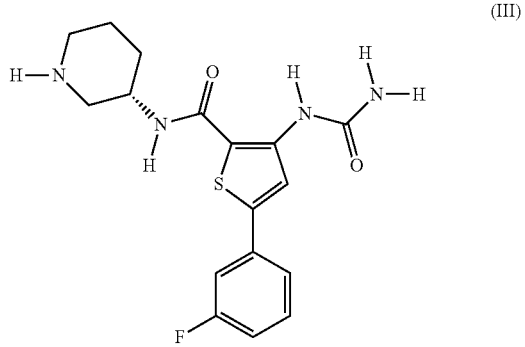 [SMILES: NC(=O)Nc1cc(-c2cccc(F)c2)sc1C(=O)N[C@H]1CCCNC1]

or a salt or solvate thereof, hereinafter as well as structurally related compounds that inhibit triple mutant EGFRs: hereinafter compound of formula III and structurally related analogs. The structurally related analogs contemplated include or are other pyrazolidinedione derivatives, for example as described in WO2005002574 herein incorporated by reference, sharing the same backbone as AZD7762 and which can inhibit mutant EGFR, preferably triple mutant EGFR comprising mutation of C797, interaction with Shc1. In an embodiment the salt is the hydrochloride. "Compound of formula III or AZD7762".

AZD7762 is a compound in the OICR TKI library with identifier OICR0001145601, Pubchem CID 11152667 and a formula $C_{17}H_{19}FN_4O_2S$. AZD7762 is available for purchase from a number of vendors including Sigma-Aldrich.

"Gilteritinib" as used herein refers to 6-ethyl-3-[3-methoxy-4-[4-(4-methylpiperazin-1-yl)piperidin-1-yl]anilino]-5-(oxan-4-ylamino)pyrazine-2-carboxamide of the formula (IV):

(IV)

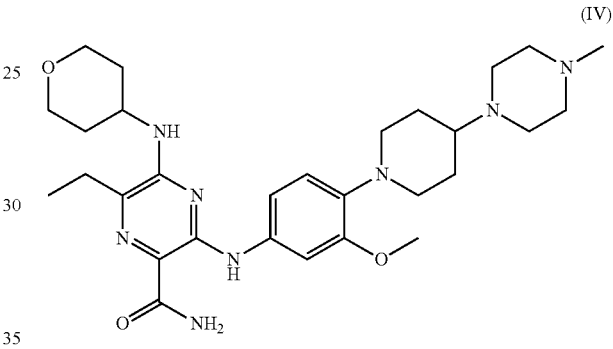

or a salt or solvate thereof, hereinafter: "Compound of formula IV or gilteritinib".

Gilteritinib, also known as ASP2215, is a receptor tyrosine kinase inhibitor of FLT3 and AXL with inhibitory activity against FLT3 internal tandem duplication (ITD) as well as tyrosine kinase domain (TKD), two common types of FLT3 mutations that are seen in up to one third of patients with acute myeloid leukemia (AML). Gilteritinib, as well as structurally related analog compounds, have been described in PCT/JP2010/057751 published on Nov. 11, 2010, as well as in U.S. Pat. Nos. 8,969,336, and 9,487,491, which are incorporated into the present application by reference. In a particular embodiment, the preferred salt is fumarate. Gilteritinib is available from a number of vendors including AK Scientific.

Cetuximab, also known as Erbitux™, is an anti-EGFR therapeutic antibody capable of inhibiting the growth of human tumor cells expressing human EGFR. Cetuximab is described in U.S. Pat. No. 6,217,866, which is incorporated into the present application by reference. Cetuximab is available from a number of vendors including BioRad.

Panitumumab, also known as Vectibix™, is a fully human monoclonal antibody against human EGFR. Panitumumab is described in U.S. Pat. No. 6,235,883, which is incorporated into the present application by reference. Panitumumab is available from a number of vendors including BioRad.

Unless defined otherwise, all technical and scientific terms used herein have the same meanings as commonly understood by one of ordinary skill in the art.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

B. Methods

Described herein are compounds, compositions and methods for inhibiting EGFR mutant complex formation and signalling that may be useful for the treatment for treating EGFR-mutant lung cancers.

Accordingly, an aspect of the disclosure provides a method of inhibiting activity of a mutant epidermal growth factor receptor (EGFR) in a cell comprising contacting the cell with a compound selected from 3-(1,3-benzoxazol-2-yl)-7-(diethylamino)-2H-chromen-2-one and a structurally related analog thereof; midostaurin or a salt or solvate thereof; AZD7762 and a structurally related analog thereof; gilteritinib or a salt or solvate thereof; and mixtures thereof.

As demonstrated in the Examples mutant EGFR comprising a C797 mutation, such as the C797S mutation that arises in lung cancers that have become resistant to TKIs such as osimertinib that are effective for inhibiting activity of and for treating cancers comprising EGFR double mutants such as L858R-T790M and ex19Del-T790M, is shown to be sensitive to compounds ("compounds of the disclosure") and combination therapies described herein.

It is demonstrated for example that the compounds of the disclosure inhibit mutant EGFR endosomal trafficking, mutant EGFR phosphorylation, mutant EGFR expression, mutant EGFR signaling, mutant EGFR proliferation and/or Shc1 complex formation.

Accordingly in one embodiment, the activity comprises inhibiting interaction of the mutant EGFR with Shc1 thereby inhibiting complex formation. In other embodiments, the activity is selected from mutant EGFR endosomal trafficking, mutant EGFR phosphorylation, mutant EGFR expression, mutant EGFR kinase activity, mutant EGFR signaling and/or mutant EGFR proliferation.

The cell can be any cell comprising mutant EGFR such as an activating mutation and/or a drug resistance mutation, optionally combined, for example combined with a drug resistance mutation C797 mutation. In an embodiment the cell is a lung cancer cell optionally non-small cell lung cancer cell. The cell can be in vitro or in vivo.

EGFR is often mutated in lung cancer and drugs have been developed to target mutant EGFR (e.g. mutations in the TK domain). Lung cancers can develop resistance and drug resistant lung cancers where C797 is mutated have been identified. It is demonstrated that compounds of the disclosure as identified in the Examples, reproducibly inhibit in a dose dependent manner cells expressing C797 mutated EGFR.

Accordingly also provided is a method of treating a subject afflicted with a lung cancer, optionally having a mutant EGFR comprising a C797 mutation, the method comprising administering to a subject in need thereof a therapeutically effective amount of a compound selected from 3-(1,3-benzoxazol-2-yl)-7-(diethylamino)-2H-chromen-2-one and a structurally related analog thereof; midostaurin or a salt or solvate thereof; AZD7762 and a structurally related analog thereof; gilteritinib or a salt or solvate thereof; and mixtures thereof.

Several TKIs such as osimertinib have been approved and demonstrated to overcome EGFR-T790M resistance. However, drug resistant triple mutant lung cancers have developed. In particular, C797S mutation present in EGFR triple mutants (C797S/T790M/activation mutation), induces resistance to osimertinib and other TKIs.

In an embodiment, the lung cancer is a drug-resistant lung cancer, optionally a drug-resistant cancer associated with EGFR C797 mutation, optionally wherein the C797 mutation is C797S.

In an embodiment, the drug resistant lung cancer comprises EGFR mutations L858R-T790M-C797S or ex19Del-T790M-0797S.

The ex19del refers to small, in frame deletions occurring in exon19 of EGFR (which encodes part of the kinase domain). They primarily occur between codons 746 to 759. This is one of the most prominent EGFR mutations in lung cancer, occurring in about 40% of all EGFR-positive NSCLC patients.

In an embodiment, the lung cancer is a NSCLC. The NSCLC can be an adenocarcinoma, squamous cell carcinoma, large cell carcinoma, adenosquamous carcinoma or a sarcomatoid carcinoma.

In one embodiment, the lung cancer is a locally advanced or metastatic non-small cell lung cancer that has failed at least one prior chemotherapy regimen.

In an embodiment, the subject is administered a mixture of the compounds. For example the mixture can be 3-(1,3-benzoxazol-2-yl)-7-(diethylamino)-2H-chromen-2-one and midostaurin, midostaurin and AZD7762, 3-(1,3-benzoxazol-2-yl)-7-(diethylamino)-2H-chromen-2-one and AZD7762, gilteritinib and 3-(1,3-benzoxazol-2-yl)-7-(diethylamino)-2H-chromen-2-one, gilteritinib and midostaurin, gilteritinib and AZD7762 or structurally related analogs of any of the foregoing combined with 3-(1,3-benzoxazol-2-yl)-7-(diethylamino)-2H-chromen-2-one, midostaurin, gilteritinib or AZD7762 or any combination thereof.

The compounds or compositions can also be administered in combination, for example where the compounds are administered in separate compositions, optionally contemporaneously, sequentially as part of a treatment regimen, such as a chemotherapy treatment regimen.

It is also demonstrated that increased (e.g. synergistic) activity is seen when the compound of the disclosure is administered with an anti-EGF antibody. As demonstrated in the examples, the toxicity of 3-(1,3-benzoxazol-2-yl-7-(diethylamino)-2H-chromen-2-one, midostaurin, or AZD7762 towards EGFR triple mutant expressing cells is increased when administered with an anti-EGFR therapeutic antibody, for example cetuximab or panitumumab.

Figure 23A:
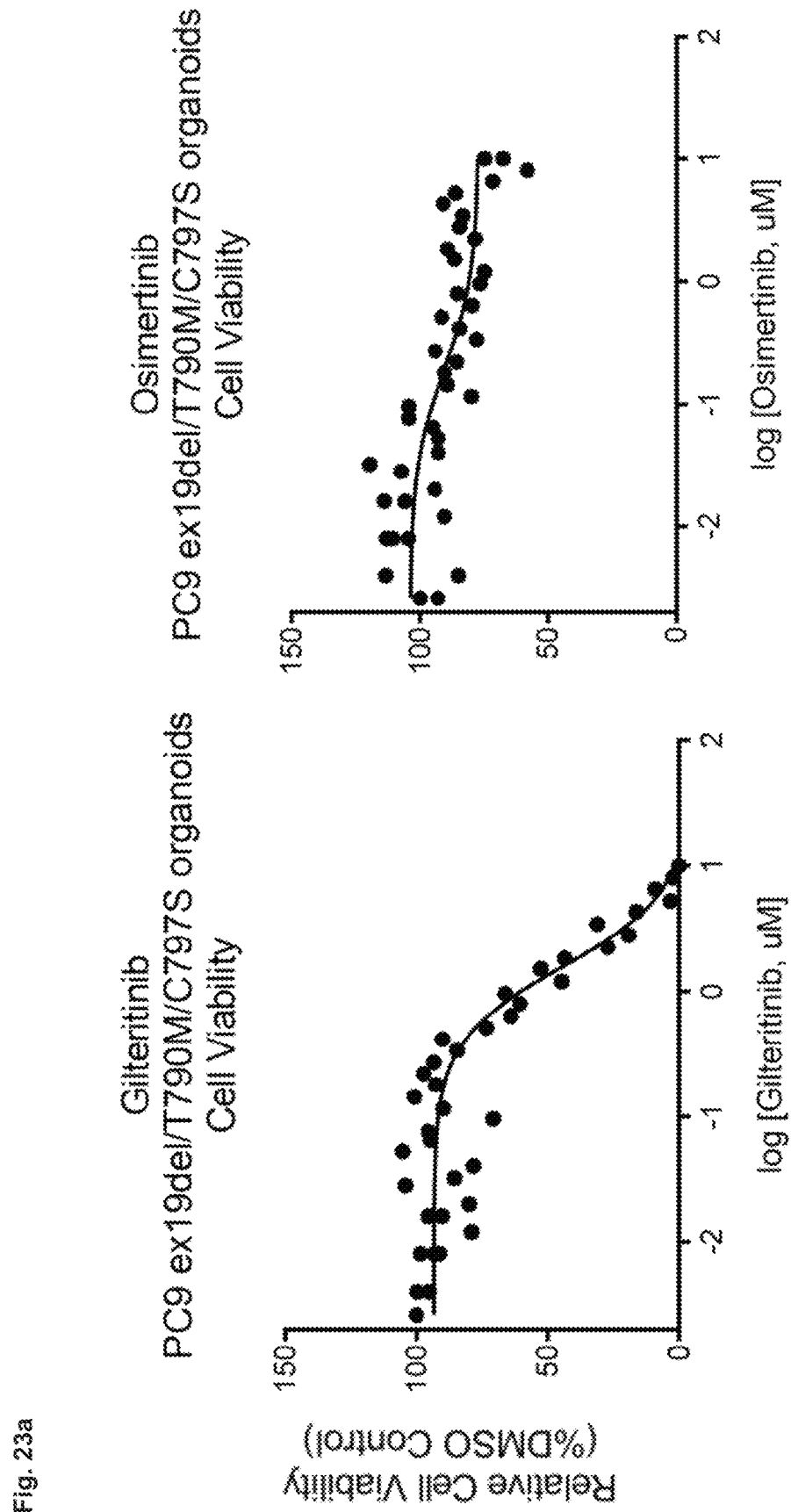
FIG. 23a-b Functional analysis of Gilteritinib against EGFR C797S triple mutants. (a) Gilteritinib but not Osimertinib reduces the viability of PC9 EGFR ex19del/T790M/C797S organoids. (b) Enhanced effects of Gilteritinib (left panel) or Midostaurin (right panel) in combination with 10 microgram/ml Panitumumab on PC9 EGFR ex19del/T790M/C797S cell viability.
Figure 23B:
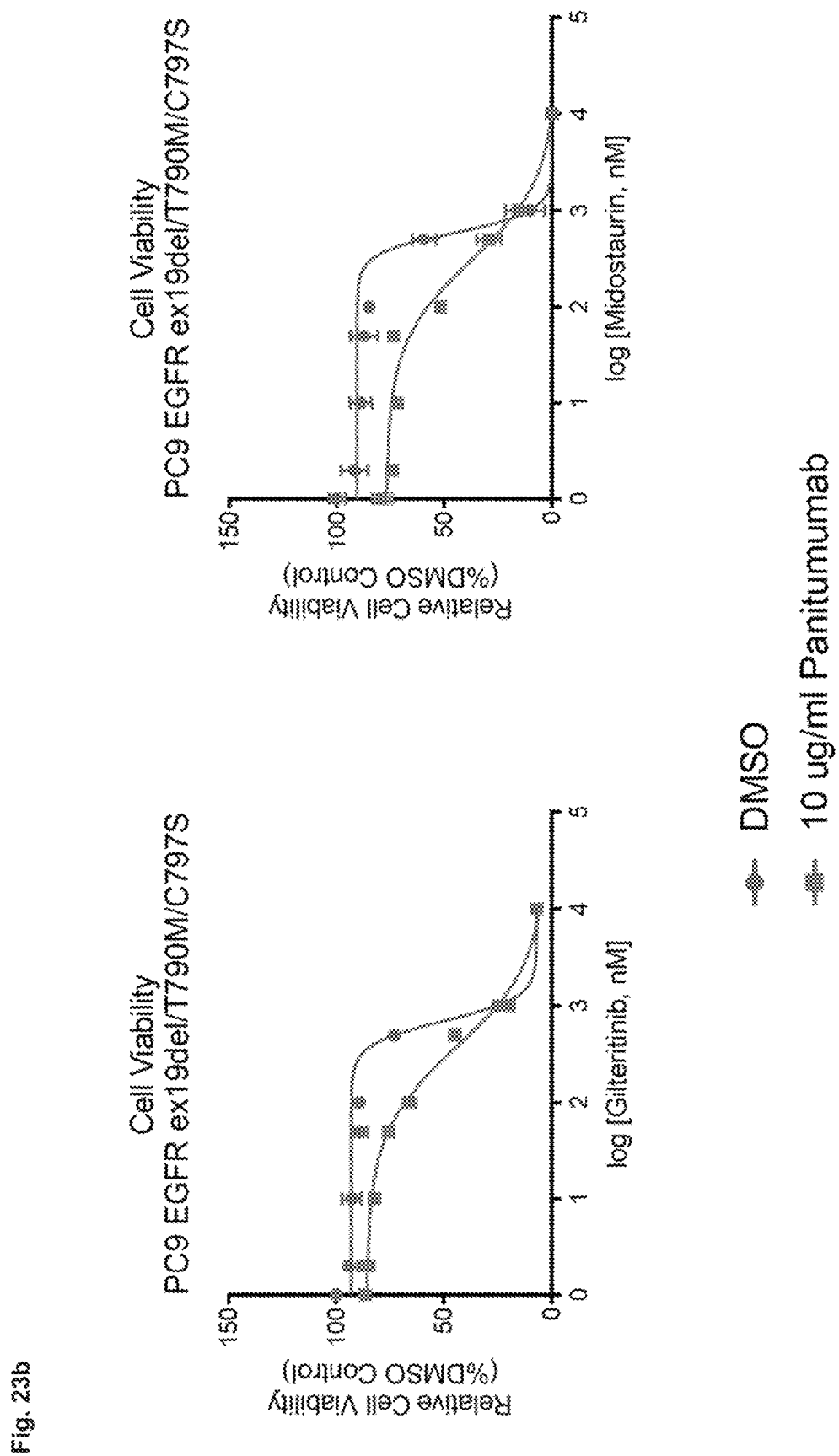

A demonstrated in the examples, gilteritinib administered with an anti-EGFR therapeutic antibody, Panitumumab, produces an increased toxicity to triple mutant expressing cells (see FIG. 23b). It is expected that combining Gilteritinb with Cetuximab would also have an increased toxicity.

Accordingly, in some embodiments, the compound or mixture is administered as a combination therapy in combination with an anti-EGF therapeutic antibody.

In particular embodiments, wherein the subject is administered a compound of formula I, formula II formula III, or formula IV, or structural analogs of formula I or III or a mixture thereof, the subject is also administered an anti-EGFR therapeutic antibody (e.g. a neutralizing anti-EGFR monoclonal antibody).

In an embodiment, the anti-EGFR therapeutic antibody is selected from Cetuximab or an antigen binding fragment thereof and Panitumumab or an antigen binding fragment thereof. Mimetics targeting the same region or epitope of EGFR as Cetuximab or Panitumumab can also be used.

The treatments can also be combined with one or more other treatments for lung cancer.

The treatment for lung cancer can for example be surgery, chemotherapy, adjuvant therapy, radiation therapy, other targeted therapy or a combination thereof.

For example, the compounds, compositions and combinations of the disclosure can be combined with a chemotherapy selected from carboplatin, cisplatin, docetaxel, gemcitabine, Nab-paclitaxel, premetresed and vinorelbine.

In some embodiments, the subject is confirmed to have one or more EGFR mutations. For example a sample (e.g. a tissue sample, a lung cancer biopsy or a liquid biopsy such as a blood sample or plasma sample for detecting tumour derived DNA and/or circulating tumour cells or circulating exosomes) from the subject is tested for the presence of the mutation. Suitable methods for obtaining tissue samples include tissue biopsy, endobronchial biopsy, transbronchial biopsy, brushing cytology, washing cytology, fine needle aspiration cytology, fluid cytology, or bone biopsy. Testing for EGFR mutations can be done by any suitable analytic technique, including quantitative real-time polymerase chain reaction (PCR), allele-specific PCR, or nucleic acid sequencing. Suitable tests include Therascreen® EGFR RGQ PCR kit (Qiagen), Cobas® EGFR Mutation Test v2 (Roche), FoundationOne CDx™ (Foundation Medicine), Oncomine™ Dx Target Test (Thermo Fisher Scientific), Guardant360™ (Guardant Health), GeneStrat (Biodesix), OncoBEAM™ (Sysmex Inostics), ExoDx® Lung (T790M) (Exosome Diagnostics), and Biocept liquid biopsy. If the mutation is present, the subject is administered a treatment as described herein.

Uses of the compounds for treating lung cancer, preferably drug resistant mutant EGFR lung cancers, are also provided.

C. Compositions and Combinations

A further aspect includes a composition or combination comprising at least two compounds selected from:
3-(1,3-benzoxazol-2-yl)-7-(diethylamino)-2H-chromen-2-one and/or structurally related analog thereof;
midostaurin or a salt or solvate thereof;
AZD7762, and/or structurally related analog thereof;
gilteritinib or a salt or solvate thereof; and
an anti-EGFR therapeutic antibody.

For example, the composition can comprise or the combination can be 3-(1,3-benzoxazol-2-yl)-7-(diethylamino)-2H-chromen-2-one and midostaurin; benzoxazol-2-yl)-7-(diethylamino)-2H-chromen-2-one and AZD7762; 3-(1,3-benzoxazol-2-yl)-7-(diethylamino)-2H-chromen-2-one and gilteritinib; midostaurin and gilteritinib; AZD7762 and gilteritinib; or midostaurin and AZD7762. In other embodiments, the composition or combination comprises a structural analog of a compound of formula I or III. In other embodiments, the combination is a compound of formula I or a structurally related analog and an anti-EGFR therapeutic antibody; a compound of formula II and an anti-EGFR therapeutic antibody; a compound of formula III or a structurally related analog thereof and an anti EGFR therapeutic antibody; or a compound of formula IV and an anti-EGFR therapeutic antibody.

The combination can be used for combination treatments. The components can be packaged separately or together, for use in conjunction or sequentially.

The composition can comprise in addition one or more pharmaceutically acceptable carriers or diluents.

In an embodiment the composition is a pharmaceutical composition.

The pharmaceutical composition can comprise two or more compounds as described above and a pharmaceutically acceptable carrier.

In an embodiment, the pharmaceutical composition is in a dosage form selected from a solid dosage form and a liquid dosage form.

In an embodiment, the pharmaceutical composition is administered by parenteral, intravenous, subcutaneous, intracardial, intramuscular, or oral administration.

In an embodiment, the pharmaceutical composition is an injectable dosage form.

In an embodiment, the injectable liquid is an injectable liquid depot suitable, for example suitable for subcutaneous administration.

The formulations can be administered orally, topically, parenterally, by inhalation or spray, or rectally in dosage unit formulations containing conventional non-toxic pharmaceutically acceptable carriers, adjuvants and vehicles. The term "parenteral" as used herein includes percutaneous, subcutaneous, intravascular (e.g., intravenous), intramuscular, or intrathecal injection or infusion techniques and the like. One or more compounds of the disclosure can be present in association with one or more non-toxic pharmaceutically acceptable carriers and/or diluents and/or adjuvants, and if desired other active ingredients. The pharmaceutical compositions of the disclosure can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the compounds of the disclosure in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

For example, a suitable dose of compound of formula (I) is in the range of about 0.1 to about 250 mg per kilogram body weight of the subject per day. For example, a suitable dose of compound of formula (II) is in the range of about 1 to 1000 mg, preferably of about 5 to about 500 mg, more preferably from 10 to 100 mg per kilogram body weight of the subject per day. Even more preferably, a suitable dose of compound of formula (II) is 50 mg orally twice daily with food, or 100 orally twice daily with food. For example, a suitable dose of compound of formula (IV), for oral administration, is in the range of about 0.001 to 100 mg/kg, preferably 0.005 to 30 mg/kg, and more preferably 0.01 to 10 mg/kg body weight, and even more preferably in a dose from 20 to 450 mg, given as a single dose or in 2 to 4 divided doses. For intravenous administration, a suitable dose of compound of formula (IV) is in the range of about 0.0001 to 10 mg/kg body weight, given in one or several doses per day. For transmucosal formulations, a suitable dose of compound of formula (IV) is in the range of about 0.001 to 100 mg/kg body weight, given in one or several doses per day. Selection of the lower range of concentration or dose for a given compound and/or analogue or combination thereof can be determined for example based upon, e.g., the $EC_{50}$ or $ED_{50}$ of the composition in established biological assays.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, ethanol, polyethylene glycol, propylene glycol, glycerin, castor oil, corn oil, gelatins, liposomes, natural polymers, synthetic polymers, polymeric blends, titanium dioxide, vitamins, coloring or pigment agents, hydroxypropyl methylcellulose, and the like.

In an embodiment, wherein the combination comprises a compound of formula I, formula II, formula III, and/or formula IV, the combination further comprises an anti-EGFR therapeutic antibody.

In an embodiment, the anti-EGFR therapeutic antibody is selected from Cetuximab and an antigen binding fragment thereof, and Panitumumab and an antigen binding fragment thereof.

Each compound in the kit or combination can be packaged separately in a separate housing such as a sterile vial or together in a single housing such as a single sterile vial.

The composition can be a pharmaceutical composition, optionally comprising one of more pharmaceutically acceptable excipients or diluents.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Figure 1B:
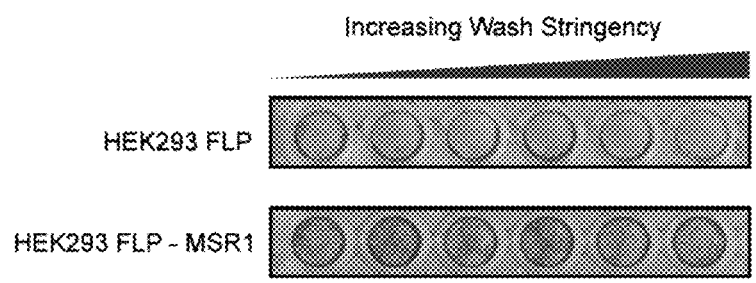
Figure 1C:
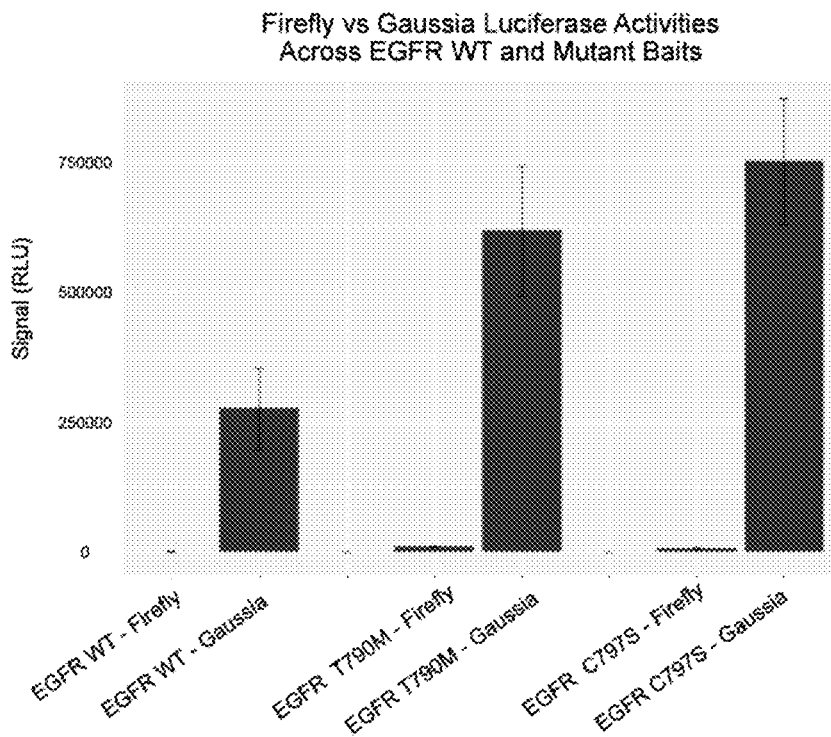

To develop this new platform, which we have called MaMTH-DS (for MaMTH 'Drug Screening'), we introduced a number of significant modifications to our traditional MaMTH system. The first modification was a transition from transiently transfected to stably expressed integral membrane bait proteins, a necessary step to minimize variability/noise and allow for sensitive detection of small-molecule activity in a large-scale multi-well format. To improve ease of stable generation, we developed reporter cell lines and a MaMTH-DS bait vector construct using the Flp-IN TREx system (Thermo Fisher), a Flp recombinase-based method which allows for rapid generation of isogenic stables in as little as two to three weeks. MaMTH-DS bait vector was made fully compatible with Gateway cloning technology (Thermo Fisher, FIG. 1a) to facilitate rapid construct generation. In order to reduce random cell loss and make the system compatible with automated handling/processing steps, we also greatly enhanced the adherent properties of our reporter cells to tissue culture plastic, via genomic integration and overexpression of the macrophage scavenger receptor (FIG. 1b). We also changed our reporter from Firefly luciferase to *Gaussia princeps* luciferase, which has the advantage of being secreted from cells into the growth media, eliminating the need for a cell lysis step, thus reducing handling steps and associated variability. Additionally, it produces a significantly higher signal than Firefly luciferase (FIG. 1c), allowing for more sensitive detection.

Figure 3A:
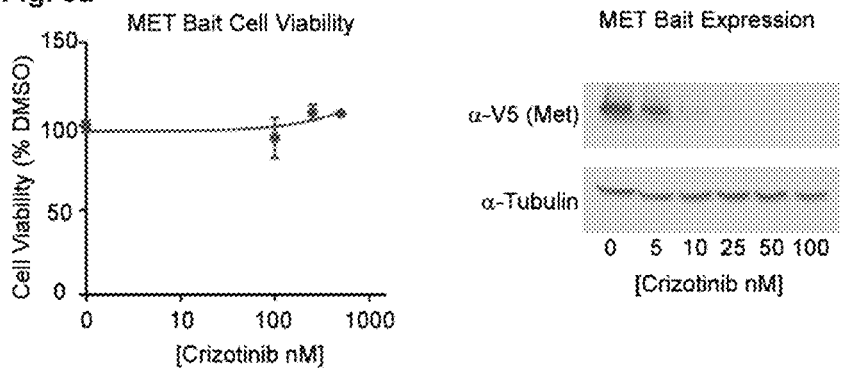
FIG. 3a-d Effect of TKI therapeutics on MaMTH RTK baits. Left panels show the effect of the indicated compounds on the viability of reporter cells expressing RTK bait. Right panels show the effect of indicated compounds on the expression of RTK bait in reporter cells. (a) MET receptor with Crizotinib. (b) FGFR4 receptor with BLU9931. (c) AXL receptor with Foretinib. (d) ALK receptor with Brigatinib.
Figure 3B:
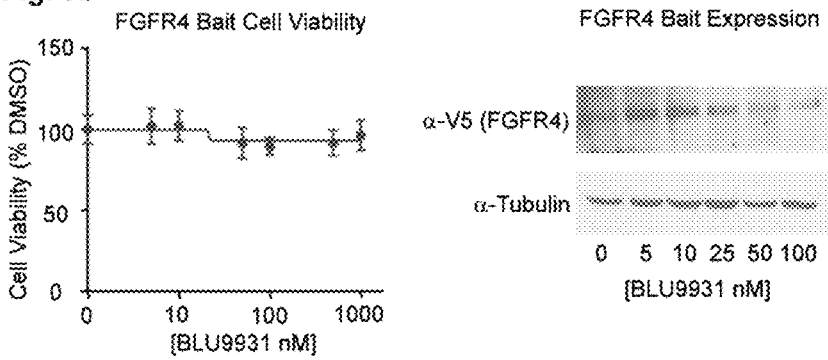
Figure 3C:
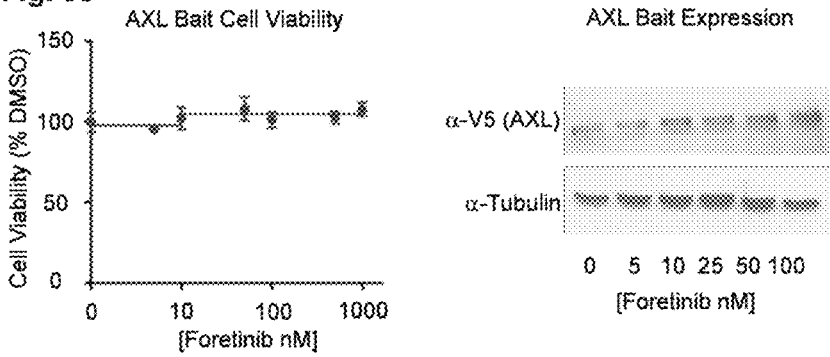
Figure 3D:
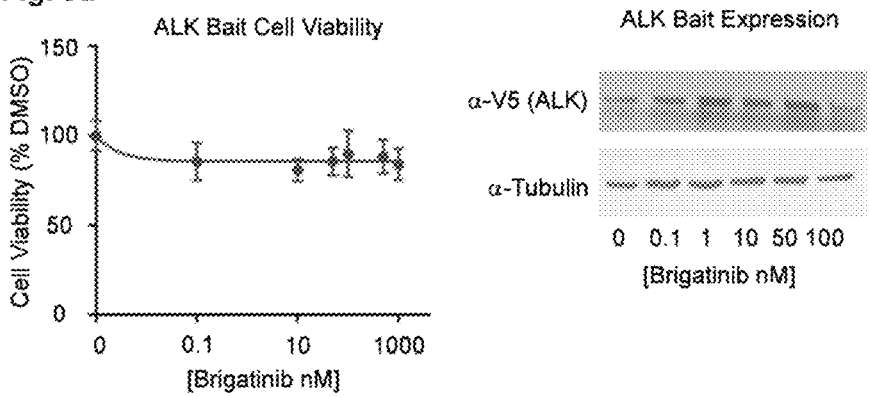

To test MaMTH-DS sensitivity and its potential suitability for use in RTK drug screening, we selected several RTKs whose dysfunction is associated with cancer, and prepared stable MaMTH-DS 'baits' in our reporter cell lines. We then performed MaMTH-DS assays in the presence of transfected Shc1 functional adapter protein 'prey' and small-molecule TKIs, including both control molecules and compounds known to specifically target the function of the corresponding RTKs. First, we examined the response of the RTK MET to the TKIs Crizotinib and Erlotinib using MaMTH-DS. As expected, the interaction was strongly reduced in a dose-dependent manner when exposed to Crizotinib, consistent with Crizotinib's reported activity against MET, but not Erlotinib, which does not target MET (FIG. 2a). Notably, the response to Crizotinib was not due to a loss in cell viability (FIG. 3a, Left Panel), though some reduction in bait expression level was observed (FIG. 3a, Right Panel), suggesting the action of the TKI reduces Met stability (and consequently interaction with Shc1). Next, we tested the response of FGFR4 bait to BLU9931, a compound reported to target this receptor. Similar to our results with MET, MaMTH-DS reporter activity was strongly reduced in the presence of BLU9931, but not in the presence of Erlotinib control (FIG. 2b). Once again BLU9931 had no effect on reporter cell viability (FIG. 3b, Left Panel). An effect of compound on FGFR bait expression was also observed (FIG. 3b, Right Panel), although this was significantly less pronounced than the effect observed with Met. We then proceeded to examine the response of two additional RTKs, AXL and ALK, to the compounds Foretinib and Brigatinib, previously shown to target these receptors, respectively. Once again, both AXL and ALK reporter activity was strongly reduced, in a dose-dependent manner, in the presence of targeting compound, but not Erlotinib control (FIGS. 2c and d), while cell viability was unaffected (FIGS. 3c and d, Left Panel). Unlike with MET and FGFR4, however, AXL and ALK expression level was not altered by compound (FIGS. 3c and d, Right Panel), suggesting that the effect of these TKIs on bait interaction with Shc1 is not due to a global reduction in receptor protein amount/stability.

Example 2

A live-cell, small-molecule screening platform based on the Mammalian Membrane Two-Hybrid (MaMTH) was used to screen a collection of 2,960 small molecules against an oncogenic Epidermal Growth Factor Receptor (EGFR) mutant resistant to the latest generation of tyrosine kinase inhibitor therapeutics.

The Mammalian Membrane Two-Hybrid (MaMTH) assay is a technology specifically designed for the large-scale identification of the protein-protein interactions (PPIs) of full-length integral membrane proteins directly in their natural membrane context in live mammalian cells[1]. MaMTH is able to detect subtle, dynamic changes in PPIs in response to mutation state and environmental changes[1-3].

Figure 4A:
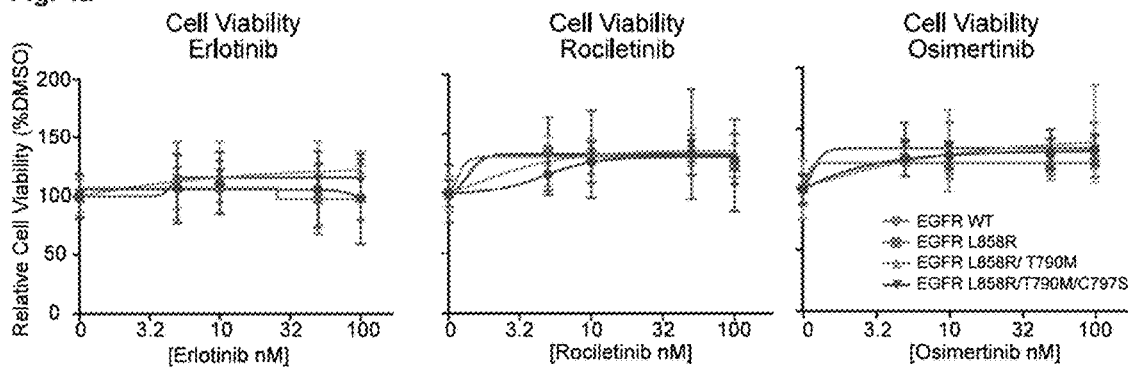
FIG. 4a-c Effect of TKI therapeutics on MaMTH reporter cells stably expressing EGFR WT and mutant baits. (a) Effect of reported TKI therapeutics on MaMTH EGFR bait reporter cell viability. (b) Effect of reported TKI therapeutics on EGFR bait expression. (c) Effect of reported TKI therapeutics on background MaMTH signal produced by EGFR baits in the absence of prey.
Figure 4B:
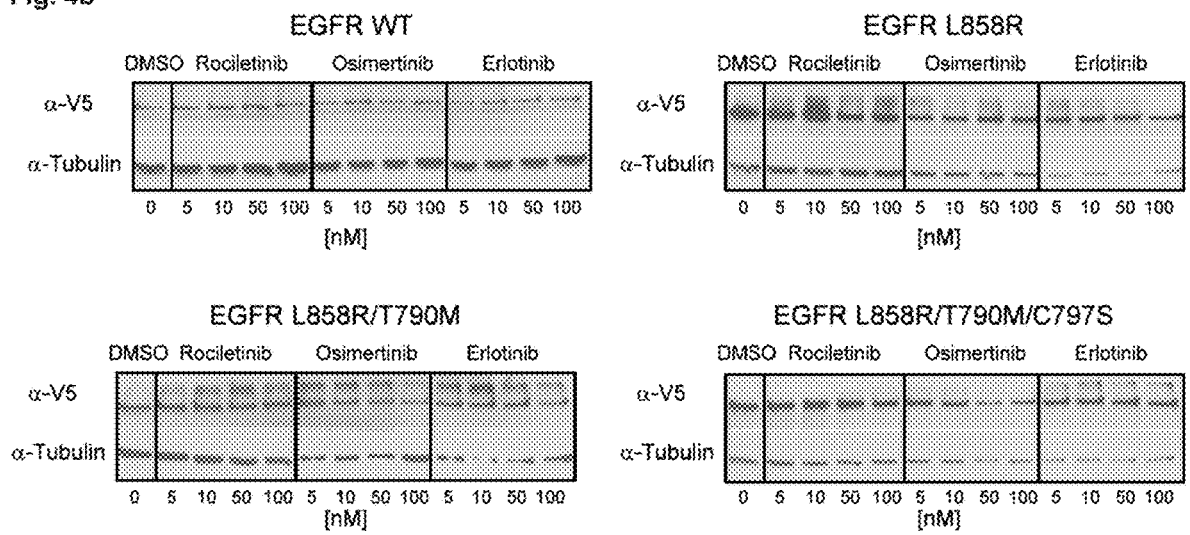
Figure 4C:
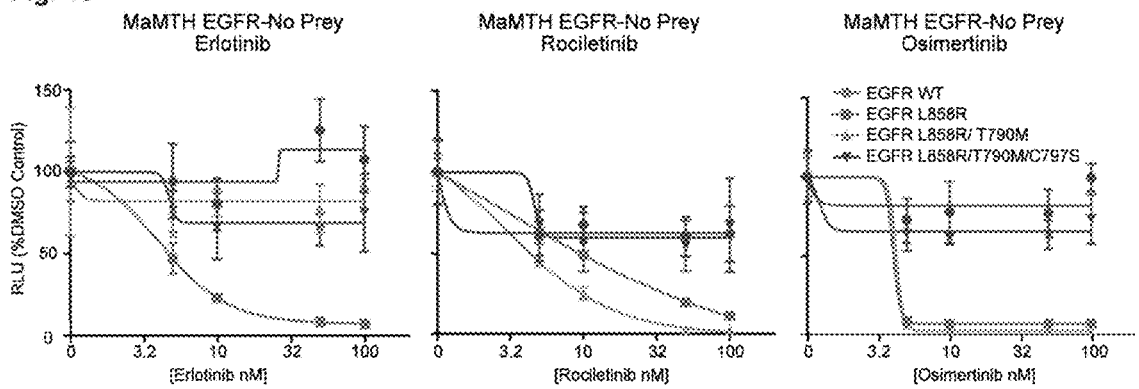
Figure 5:
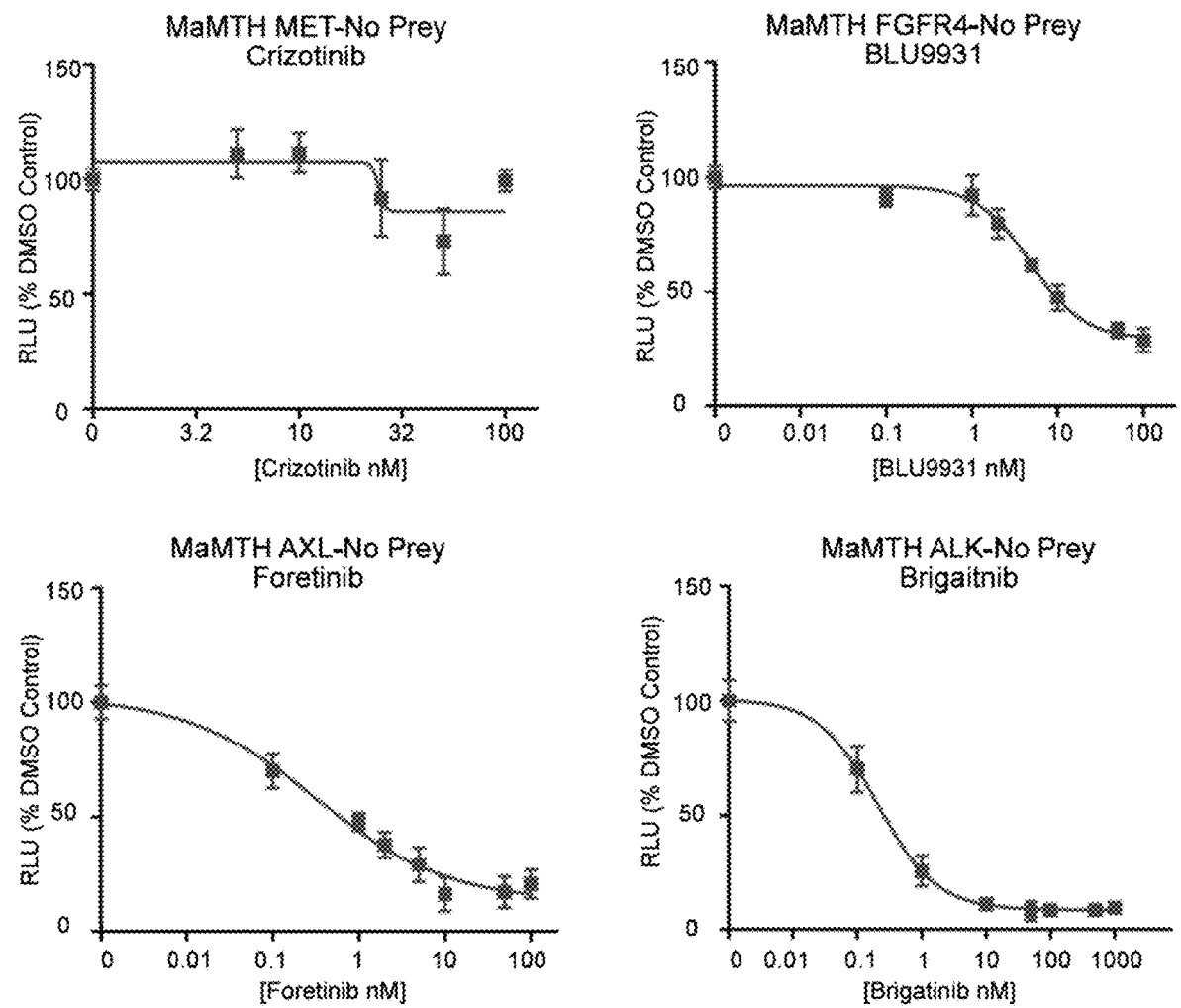
FIG. 5 Effect of TKI molecules on MaMTH-DS signal in reporter cells stably expressing MET, FGFR4, AXL or ALK receptor in the absence of prey.
Figure 6:
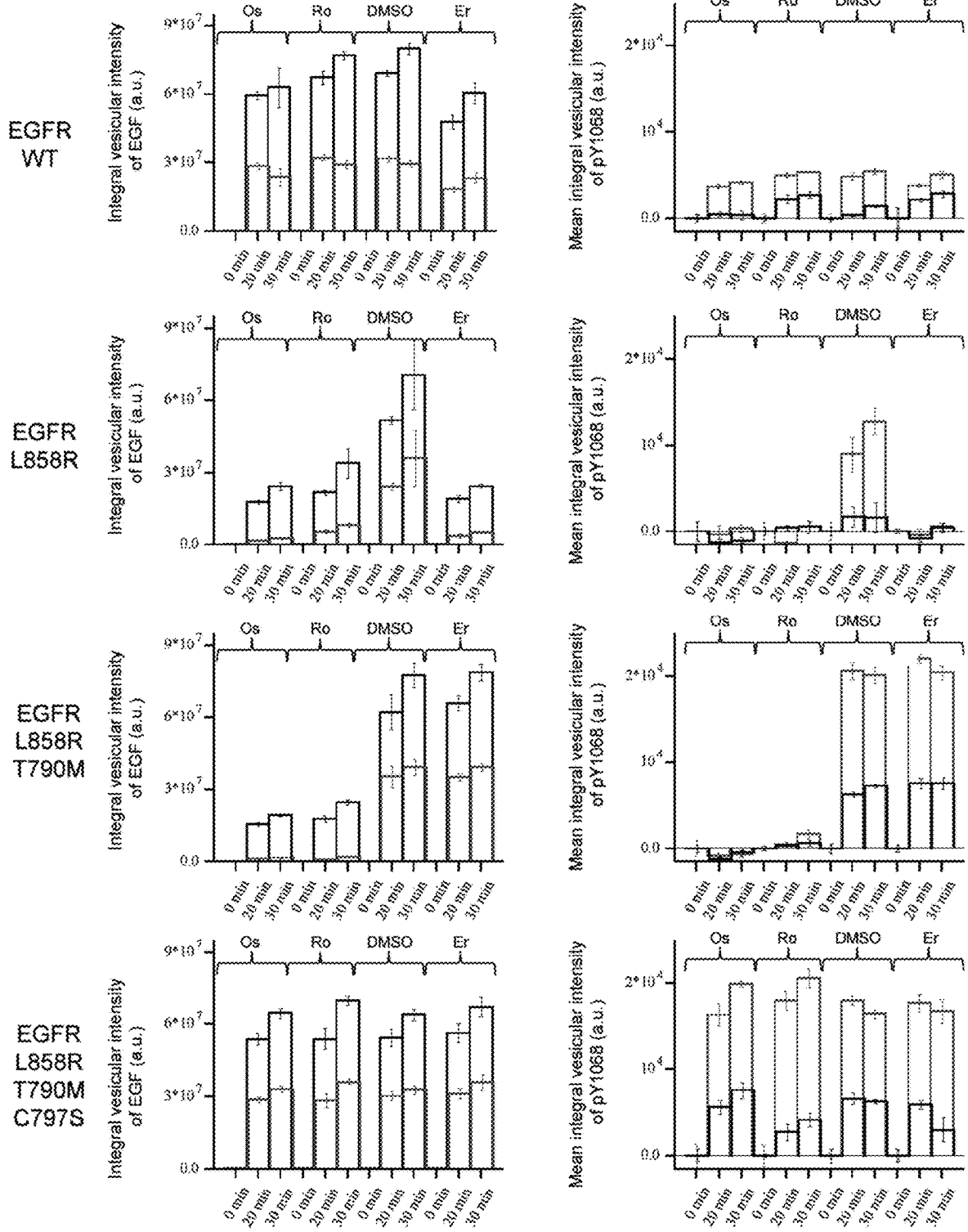
FIG. 6 Effect of therapeutic TKIs on endosomal trafficking of EGFR WT and mutants in MaMTH reporter lines. Left panels present total integral vesicular intensity of EGF (black) and EGF co-localized with EEA1 (red). Right panels show mean integral intensity of Y1068 phosphorylated EGFR endosomes (black) and mean over EEA1-positive endosomes (red) upon EGF stimulation and TKI treatment. Intensity distribution of pY1068 in un-stimulated (0 min) cells was subtracted from intensity distributions at 20 and 30 min to correct for background signal. Os=Osimertinib. Ro=Rociletinib. Er=Erlotinib.

Mutants of the Epidermal Growth Factor Receptor (EGFR) are associated with cancers such as non-small cell lung cancer (NSCLC) specifically the single mutant EGFR L858R, as well as the EGFR/L858R/T790M double and EGFR/L858R/T790M/C797S triple mutants which are associated with acquired resistance to NSCLC tyrosine kinase inhibitor (TKI) therapeutics[5-7]. The differential effects of three therapeutic TKIs (Erlotinib, Rociletinib and Osimertinib) on EGFR mutants were assessed by MaMTH using the Shc1 interaction partner as prey. In agreement with clinical results, the first generation TKI Erlotinib affected the interaction of Shc1 with the L858R mutant bait, but not with WT or either drug-resistant mutant, while the third generation TKIs Rociletinib and Osimertinib affected both L858R and T790M-carrying mutant baits, but not WT or the C797S triple mutant baits (FIG. 2). The observed differences were not due to a reduction in cell viability (FIG. 4a), and no significant effect on bait expression was evident in response to any of the TKIs (FIG. 4b). An effect of the TKIs on background MaMTH reporter signal was observed in the absence of prey for EGFR baits (FIG. 4c) an effect which was also observed with FGFR4, AXL and ALK, but not MET (FIG. 5). Further investigation suggested this was a consequence of a reduction in normal EGFR endosomal trafficking, associated with receptor activation and function[8], in TKI-inhibited mutants (FIG. 6). This could result in lower background reporter activation due to reduced endosomal-mediated EGFR degradation (and potential non-specific TF release) or EGFR nuclear localization[9]. Additionally, this suggests that interaction of EGFR with Shc1 is affected, at least in part, by TKI-mediated inhibition of mutant EGFR endosomal trafficking, which highlights the ability of MaMTH to sensitively detect loss of functional interactions in response to different effects of drug action.

Figure 7:
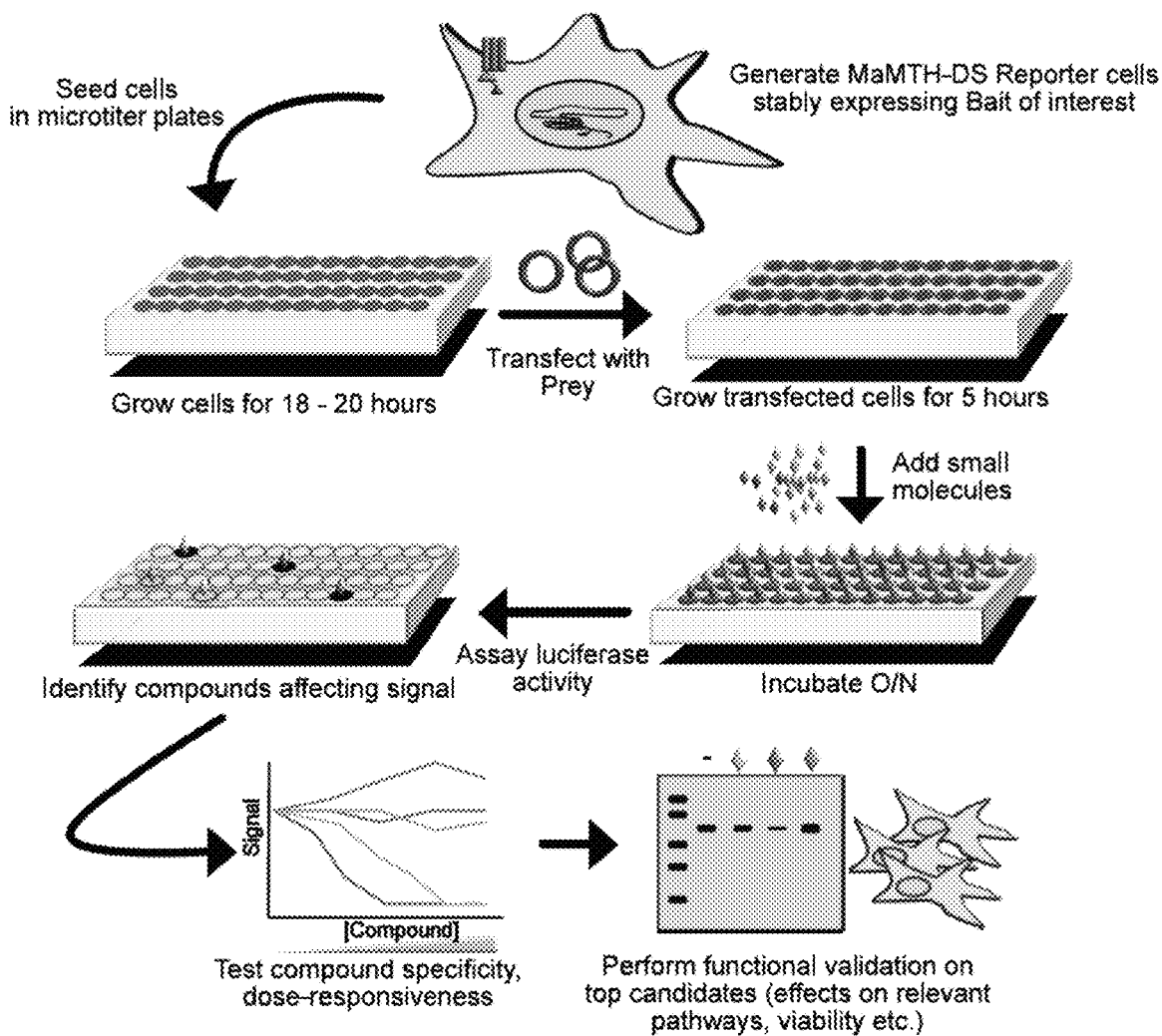
FIG. 7 Schematic representation of the MaMTH-DS platform workflow.

The MaMTH system was modified into a high-throughput, small molecule screening platform, (MaMTH-DS). MaMTH-DS stably expressed baits, reporter cell lines and MaMTH bait vector construct using the Flp-IN TREx system (Thermo Fisher), a Flp recombinase-based method which allows for rapid generation of isogenic stables. The system uses a *Gaussia princeps* luciferase reporter. The system was constructed for use in a 384-well format (FIG. 7).

Figure 9A:
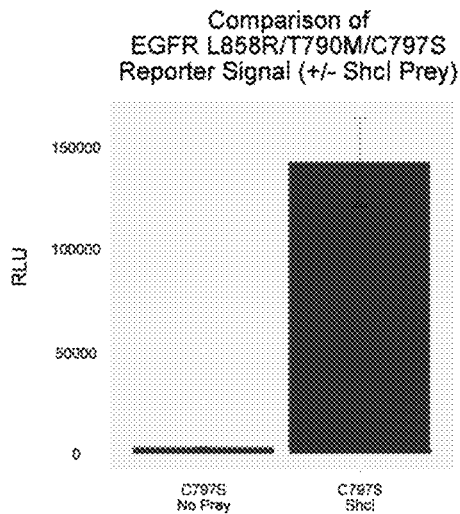
FIG. 9a-c MaMTH-DS screen of EGFR L858R/T790M/C797S in the presence of Shc1. (a) Comparison of raw reporter signal of EGFR L858R/T790M/C797S MaMTH bait cell line with and without transfected Shc1 prey. (b) Sample distributions of untransformed and Box-Cox power transformed data (using a value of Lambda=0.71 and 0.87 for screening rounds 1 and 2, respectively). P-Values from Shapiro-Wilk's normality test of data are shown in inset. (c) Box and whisker plots showing distribution of sample values across plates for non-normalized, NPI-normalized and BScore-normalized data. Medians are indicated by thick black lines. Filled blue boxes encompass the 25th to 75th percentiles. Whiskers extend to the largest and smallest values not greater than 1.5 times the IQR. Outlying points beyond the whiskers are shown individually in red.
Figure 9B:
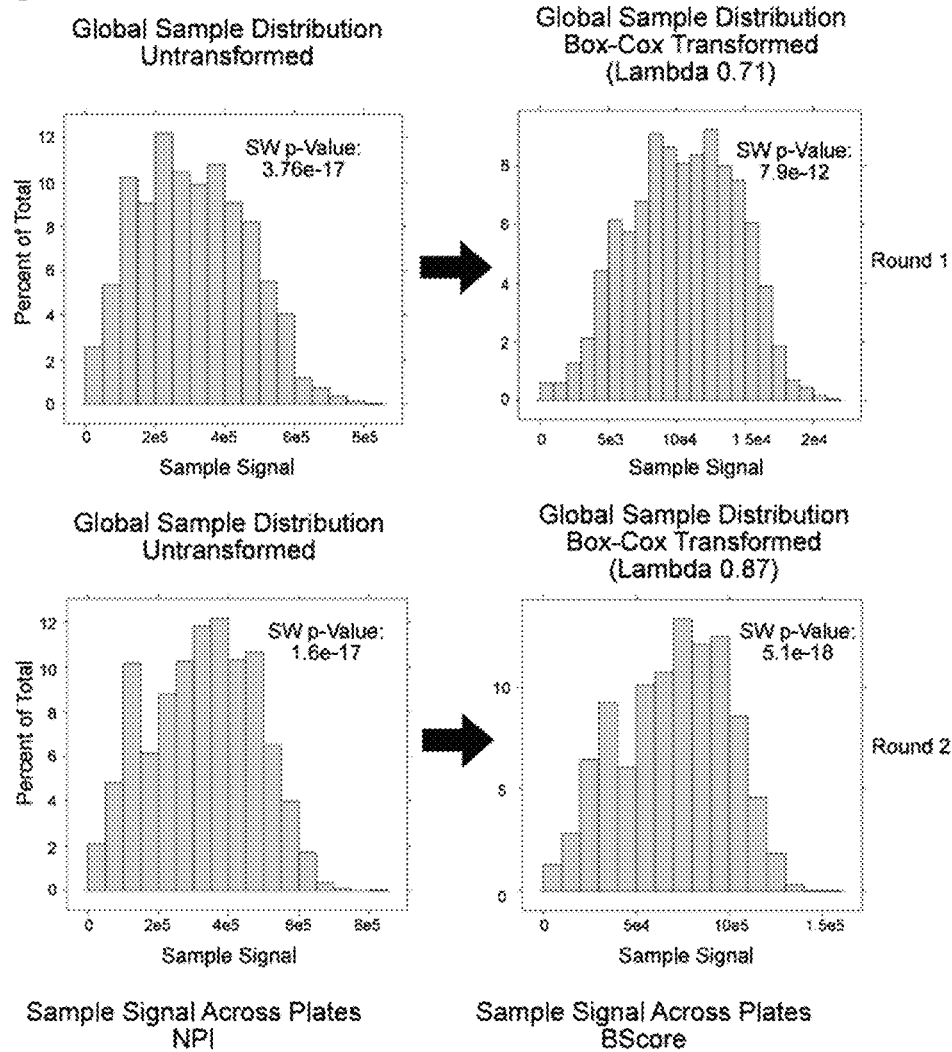

Screening of the EGFR/L858R/T790M/C797S triple mutant was conducted using MaMTH-DS, which is of great clinical relevance because of its resistance to the latest generation of clinically approved anti-EGFR TKI therapeutics[7], against a library of 2960 diverse small-molecules (FIG. 8a). Although drug response with TKIs was observed for sensitive mutants in the absence of prey (FIG. 4c), screening was performed in the presence of Shc1, due to the significant enhancement in signal in the presence of interacting prey (FIG. 9a), and to allow for the ability to detect compounds which might inhibit the interaction of EGFR with Shc1 in a manner not involving an alteration in endosomal trafficking of the receptor. MaMTH-DS screening was carried out twice (in two independent experiments) to test for reproducibility, and was performed in a semi-automated manner, using robotics for cell seeding, sample transfection and small molecule addition. All screen data was subject to Box-Cox power transformation[11] to improve sample data distribution symmetry and normality prior to further analysis (FIG. 9b). Z-prime values across all ten screened plates exceeded 0.5 in the first round of screening (average 0.68 overall), while all ten plates exceeded 0.4 (with seven plates exceeding 0.5) in the second round (average 0.56 overall), supporting excellent assay quality in both cases[12] (FIG. 8b).

Figure 9C:
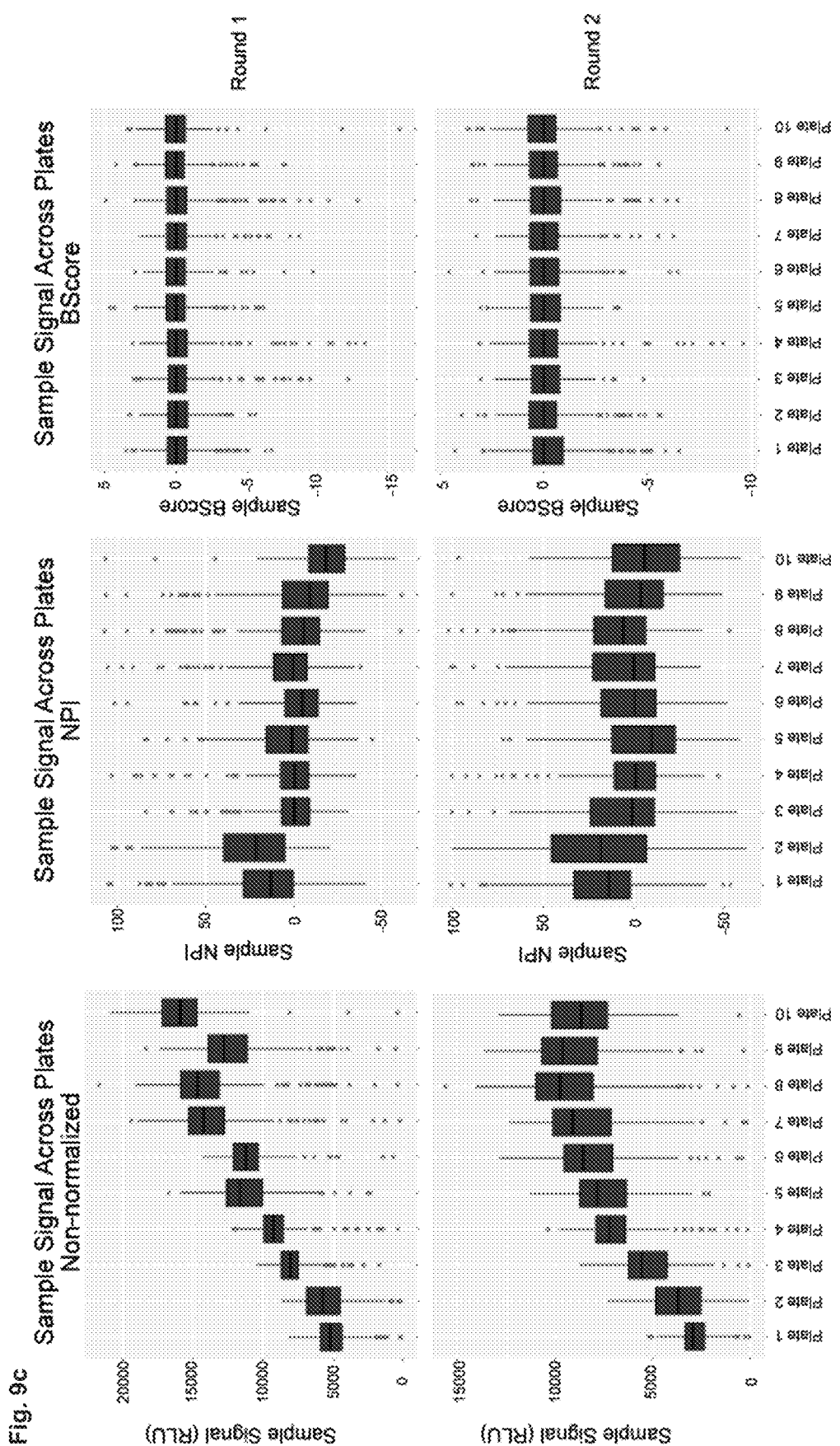

Data normalization was performed on a per plate basis, using both controls-based (Normalized Percent Inhibition, NPI) and sample-based (BScore[13]) approaches, to correct for plate variation and positional effects (FIG. 9c). NPI and BScore correlated well, and inhibitory hits were scored based on a combined cut-off of greater than 70% NPI and a BScore of −3 or less (FIG. 8c), detecting a total of 49 candidates from Round 1 and 45 candidates from Round 2 (FIG. 10). Overlap between both rounds was excellent, with 34 hits shared between both rounds (FIG. 8d).

To eliminate compounds displaying significant activity against EGFR-WT and/or general toxicity, all 34 shared hits were retested, using MaMTH, in triplicate against both EGFR-L858R-T790M-C797S and EGFR-WT (Table 1).

TABLE 1

Specificity and reproducibility testing of MaMTH-DS hits, identified in both rounds of screening, against EGFR-WT and EGFR-L858R-T790M-C797S baits in the presence of Shc1.

| Comp. Source | Comp. ID | Average Percent | Std. Dev. Percent | % CV Percent | Average Percent | Std. Dev. Percent | % CV Percent | WT > 50% Inhibition | C797S > 50% Inhibition | p-Value | Fold. WT. C797S | |
|---|---|---|---|---|---|---|---|---|---|---|---|---|
| OICR TKI | OICR0000317A01 | 129.3 | 28.5 | 22.1 | 10.5 | 2.6 | 24.9 | NO | YES | 0.017991867 | 12.3 | Meet criteria |
| Chembridge | 5213777 | 105.3 | 30.6 | 29.1 | 27.8 | 11 | 39.7 | NO | YES | 0.036213511 | 3.8 | for establishing |
| OICR TKI | OICR0000805A01 | 80.2 | 8.1 | 10.1 | 18.3 | 1.2 | 6.6 | NO | YES | 0.004903998 | 4.4 | reproducibility |
| OICR TKI | OICR0000327B01 | 57.5 | 0.9 | 1.6 | 16.3 | 0.5 | 2.9 | NO | YES | 7.30E−06 | 3.5 | and mutant |
| OICR TKI | OICR0001145B01 | 56.4 | 8.1 | 14.3 | 15.8 | 1.4 | 8.6 | NO | YES | 0.011228412 | 3.6 | specificity. |
| Maybridge | BR00086SC | 24.9 | 0.5 | 1.9 | 6.2 | 0.4 | 6.9 | YES | YES | 9.30E−07 | 4 | Do not meet |
| Maybridge | SPB01851SC | 24.5 | 5.9 | 23.8 | 5.8 | 1.6 | 28.1 | YES | YES | 0.024156361 | 4.3 | criteria for |
| Maybridge | SEW06379SC | 23.3 | 2.1 | 8.9 | 17.1 | 2.6 | 15.5 | YES | YES | 0.035165788 | 1.4 | establishing |
| Chembridge | 5304079 | 21.5 | 3 | 13.9 | 11.7 | 3.7 | 31.8 | YES | YES | 0.025512837 | 1.8 | reproducibility |
| OICR TKI | OICR0008718A01 | 19.9 | 6.3 | 31.7 | 4.5 | 2.3 | 52.6 | YES | YES | 0.038481202 | 4.5 | and mutant |
| Maybridge | BTB08928SC | 17.3 | 1.8 | 10.4 | 5.3 | 0.5 | 9.9 | YES | YES | 0.004433972 | 3.2 | specificity. |
| Chembridge | 5106405 | 15.8 | 3 | 18.8 | 2.7 | 1.1 | 41.6 | YES | YES | 0.009345886 | 5.8 | |
| Maybridge | S14919SC | 13.7 | 2.7 | 19.4 | 2.9 | 1.3 | 44.9 | YES | YES | 0.008764106 | 4.8 | |
| OICR TKI | OICR0007886A01 | 11.5 | 2.7 | 23.3 | 4.6 | 0.5 | 9.8 | YES | YES | 0.043699193 | 2.5 | |
| OICR TKI | OICR0011111A01 | 7.6 | 1.9 | 24.4 | 0.9 | 0.2 | 25.2 | YES | YES | 0.023346445 | 8.1 | |
| Chembridge | 5357830 | 6.2 | 2 | 33.1 | 0.9 | 0.2 | 22 | YES | YES | 0.046079898 | 6.6 | |
| Chembridge | 5274945 | 4.4 | 0.5 | 12 | 0.4 | 0.1 | 33.5 | YES | YES | 0.004005023 | 12 | |
| Maybridge | KM08160SC | 4.1 | 1.3 | 32 | 0.6 | 0.3 | 54 | YES | YES | 0.037344862 | 6.6 | |
| OICR TKI | OICR0000321A01 | 2.3 | 0.4 | 19.6 | 0.5 | 0.3 | 71.5 | YES | YES | 0.006113406 | 5 | |
| Chembridge | 5238658 | 0.9 | 0.2 | 26.7 | 0.2 | 0.1 | 56.1 | YES | YES | 0.022392801 | 4.4 | |
| OICR TKI | OICR0011130B01 | 6.5 | 2.7 | 40.9 | 0.5 | 0.4 | 74.7 | YES | YES | 0.057112926 | 12.4 | |
| OICR TKI | OICR0000296B01 | 5.5 | 2.5 | 45.2 | 0.3 | 0.2 | 65.6 | YES | YES | 0.068205877 | 16.3 | |
| OICR TKI | OICR0000536B01 | 7.3 | 4.1 | 56.7 | 0.3 | 0.1 | 25.9 | YES | YES | 0.098676818 | 26.6 | |
| Maybridge | CD03862SC | 5.2 | 2 | 38.5 | 2.4 | 0.8 | 35.3 | YES | YES | 0.120873261 | 2.2 | |
| Chembridge | 5109882 | 14.8 | 2.2 | 14.6 | 11.9 | 1 | 8.5 | YES | YES | 0.1303195 | 1.2 | |
| Maybridge | JA00113SC | 3.4 | 2.3 | 66.5 | 0.4 | 0.1 | 32.1 | YES | YES | 0.146340884 | 8.9 | |
| OICR TKI | OICR0001118A01 | 4.4 | 3.4 | 77.9 | 0.3 | 0.2 | 55.4 | YES | YES | 0.175813511 | 13.1 | |
| OICR TKI | OICR0008768A01 | 6.5 | 5.7 | 88.4 | 0.3 | 0 | 7.5 | YES | YES | 0.203901998 | 20 | |
| Chembridge | 5792598 | 84.2 | 10.2 | 12.2 | 114.8 | 29.8 | 25.9 | NO | NO | 0.209695268 | 0.7 | |
| Chembridge | 5333931 | 45.6 | 1.8 | 3.9 | 42 | 3.7 | 8.7 | YES | YES | 0.221411804 | 1.1 | |
| OICR TKI | OICR0000531B01 | 11.5 | 0.5 | 4.6 | 14.5 | 3.2 | 22.3 | YES | YES | 0.239198175 | 0.8 | |
| OICR TKI | OICR0011123A01 | 33.43 | 8.46 | 25.3 | 38.24 | 1.06 | 2.77 | YES | YES | 0.429149913 | 0.9 | |
| Maybridge | SEW02515SC | 6.7 | 1.8 | 26.5 | 6.4 | 1.1 | 17.4 | YES | YES | 0.830386676 | 1 | |
| Chembridge | 5270140 | 8.3 | 5.2 | 62.7 | 8.6 | 4 | 46.5 | YES | YES | 0.931181228 | 1 | |

*C797S refers to the triple mutant

Figures 11A, 11B:
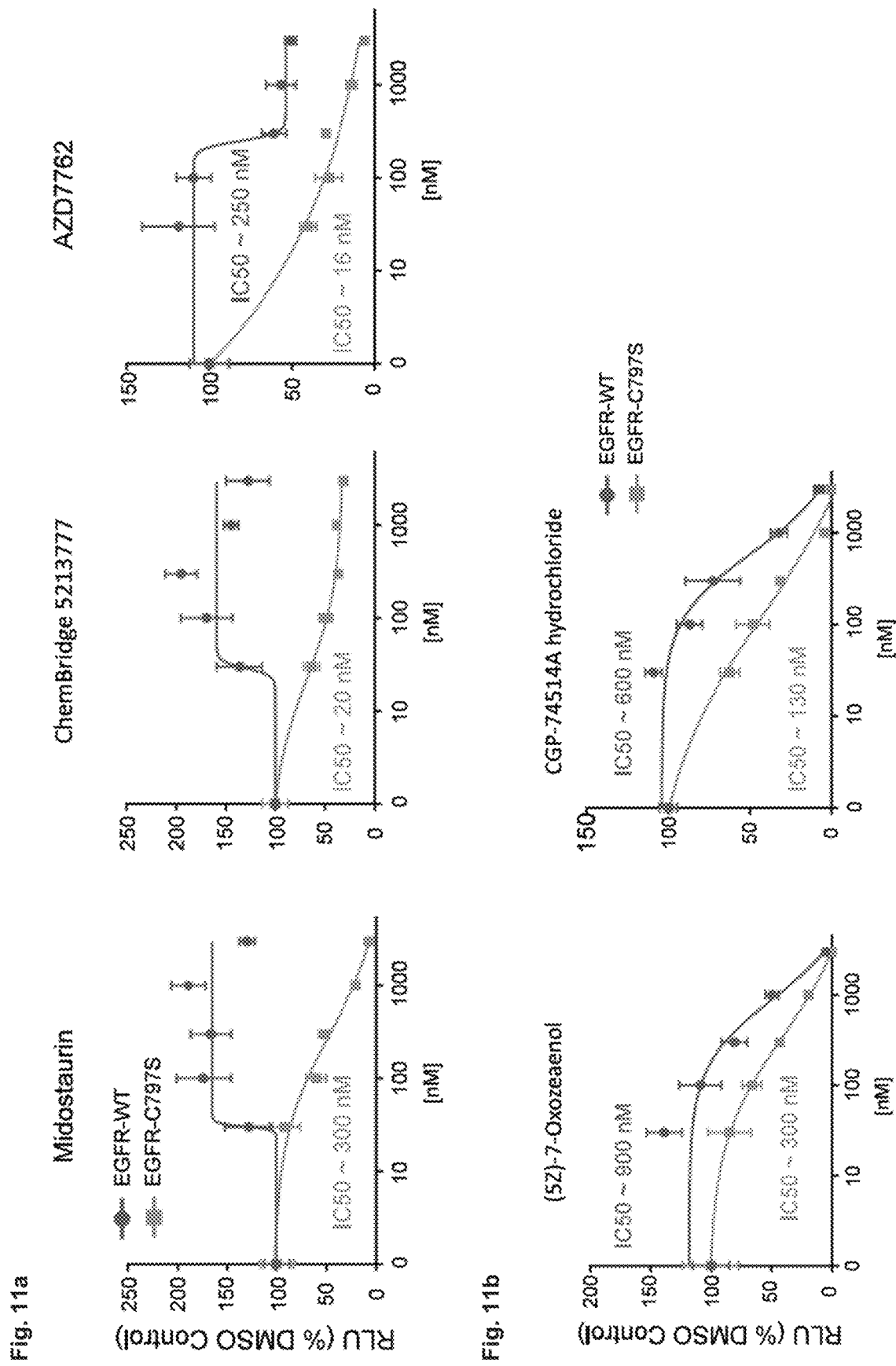
FIG. 11a-b MaMTH dose response analysis of top hits from MaMTH-DS screens of EGFR L858R/T790M/C797S in the presence of Shc1. (a) Curves for the three candidates showing robust, dose-responsive and mutant specific inhibition, selected for further analysis. (b) Curves for two candidates not selected for further analysis.

From these results, compounds were selected for further consideration only if they inhibited EGFR/L858R/T790M/C797S (but not EGFR-WT) greater than 50% and if the difference in their inhibition of mutant vs WT was both statistically significant and at least 2-fold (FIG. 8e and Table 1). The 5 compounds satisfying these criteria were then subjected to dose-response testing (FIGS. 11a and b), of which 3 were found to display robust, dose-dependent inhibition of EGFR-L858R-T790M-C797S, meeting the above criteria for at least two different doses (FIG. 8e and FIG. 11a).

Figure 12:
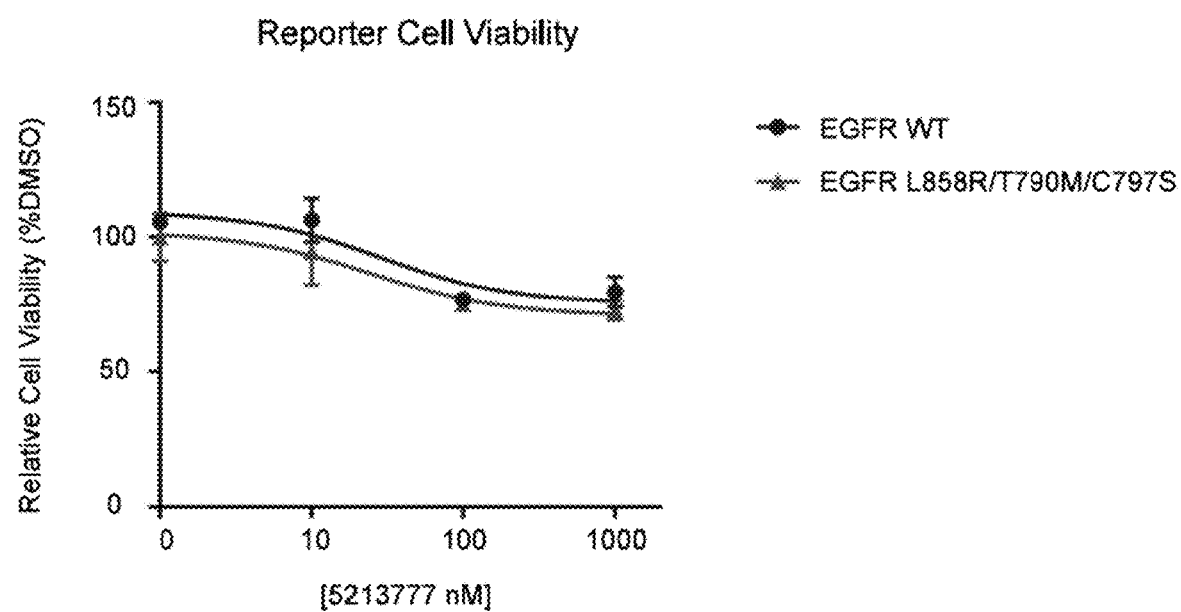
FIG. 12 Effect of Chembridge 5213777 on viability of MaMTH-DS reporter cells expressing EGFR WT or EGFR L858R/T790M/C797S.
Figure 13A:
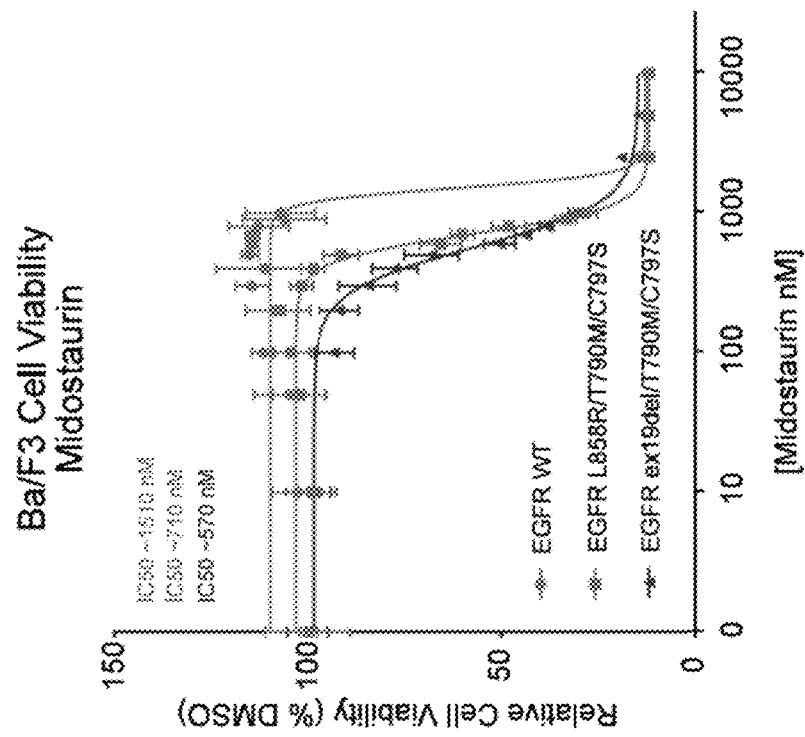
FIG. 13a-d Functional analysis of Midostaurin against EGFR-C797S triple mutants. (a) Effect of Midostaurin on EGFR and downstream signalling molecule expression and phosphorylation in Ba/F3 cells expressing EGFR L858R/T790M/C797S, EGFR ex19del/T790M/C797S or EGFR WT. (b) Effect of Midostaurin on viability of Ba/F3 cells expressing EGFR L858R/T790M/C797S, EGFR ex19del/T790M/C797S or EGFR WT. (c,d) Enhanced effect of Midostaurin in combination with 68 nM Cetuximab (CTX) or 140 nM Panitumumab on Ba/F3 EGFR L858R/T790M/C797S and EGFR ex19del/T790M/C797S cell viability. Brigatinib is included for comparison. Statistical significance of differences in cell viability were determined using the Student's t-test. ** indicates a p-Value less than 0.01.
Figure 13B:
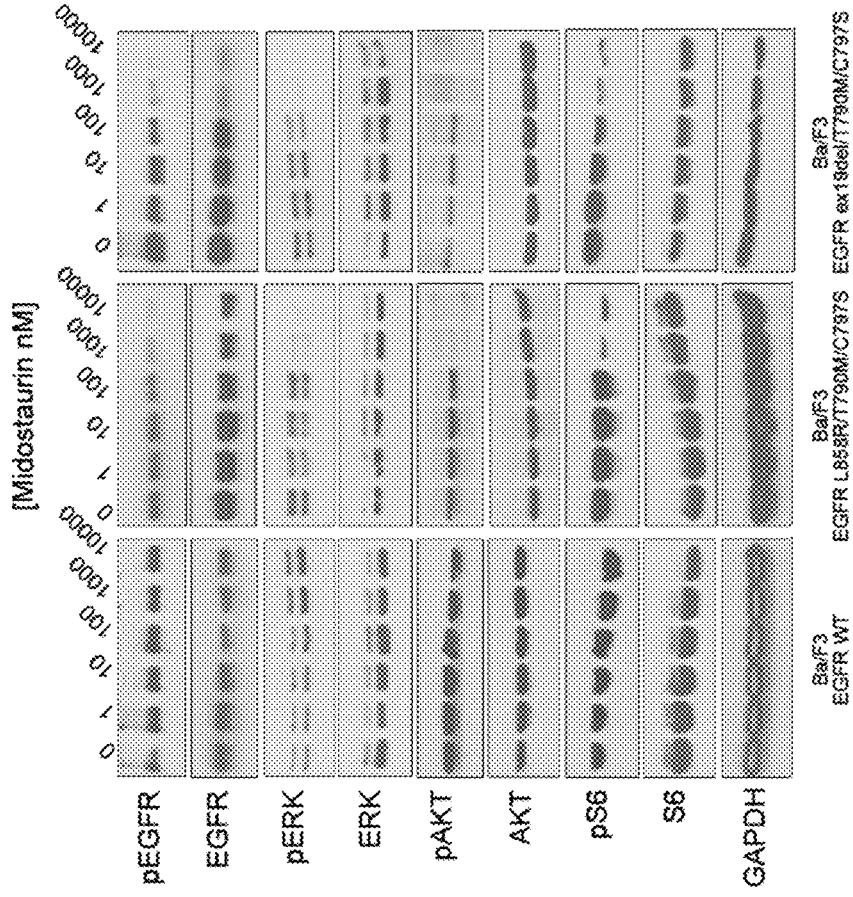
Figure 13C:
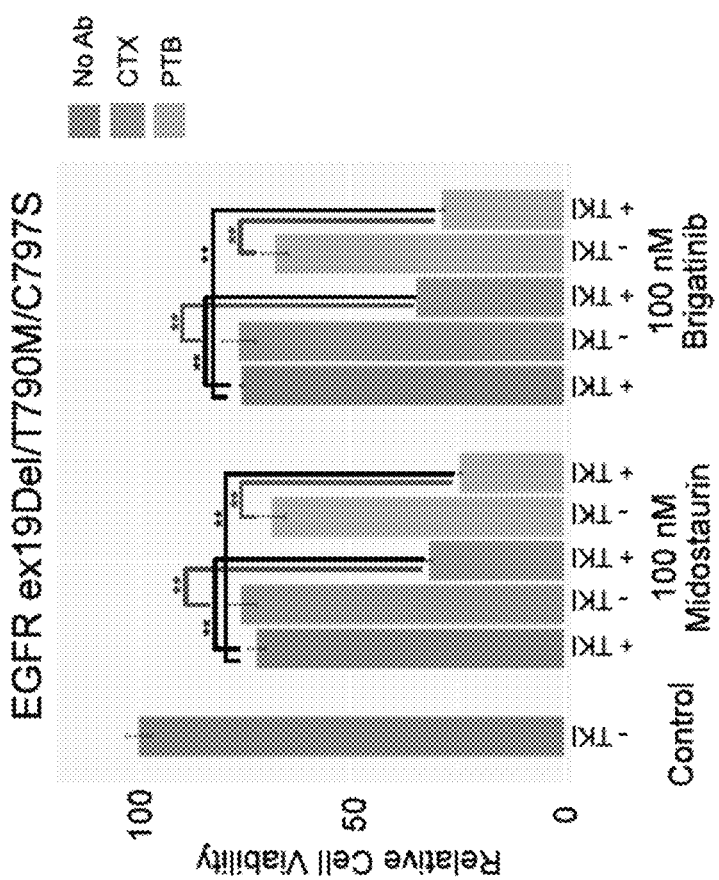
Figure 13D:
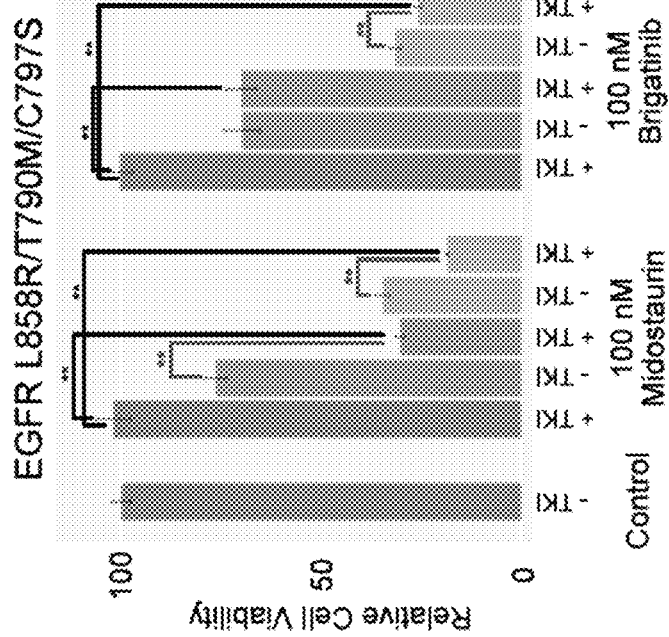
Figure 14B:
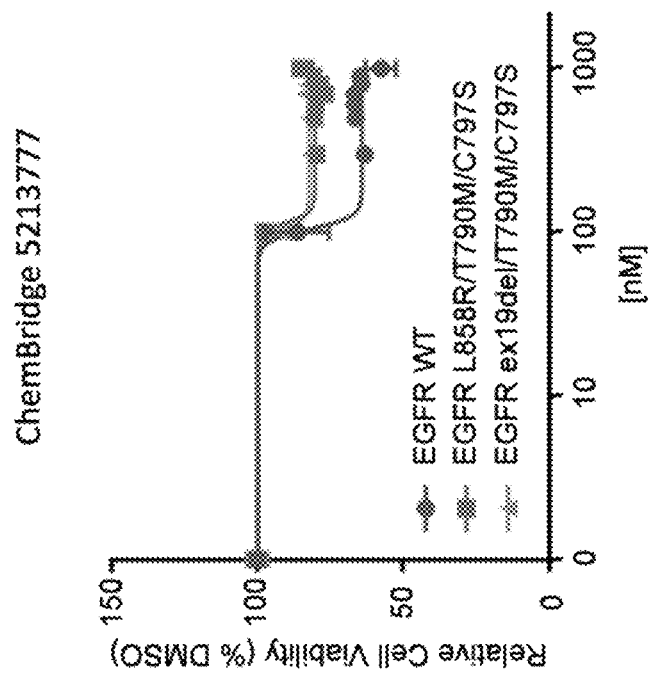
FIG. 14a-d Functional analysis of 5213777 against EGFR C797S triple mutants. (a) Effects of 5213777 on EGFR and downstream signalling molecule expression and phosphorylation in Ba/F3 cells expressing EGFR L858R/T790M/C797S, EGFR ex19del/T790M/C797S or EGFRWT. (b) Effects of 5213777 on viability of Ba/F3 cells expressing EGFR L858R/T790M/C797S, EGFR ex19del/T790M/C797S or EGFR WT. (c,d) Enhanced effect of 5213777 in combination with 68 nM Cetuximab (CTX) or 140 nM Panitumumab on Ba/F3 EGFR L858R/T790M/C797S and EGFR ex19del/T790M/C797S cell viability. Statistical significance of differences in cell viability were determined using the Student's t-test. ** indicates a p-Value less than 0.01.
Figure 14A:
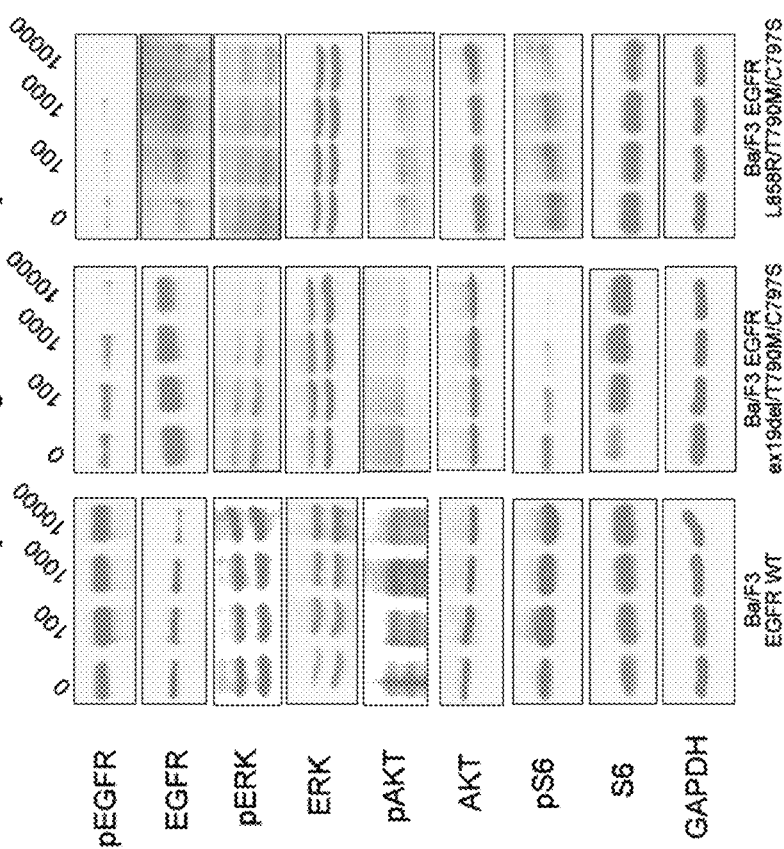
Figure 14C:
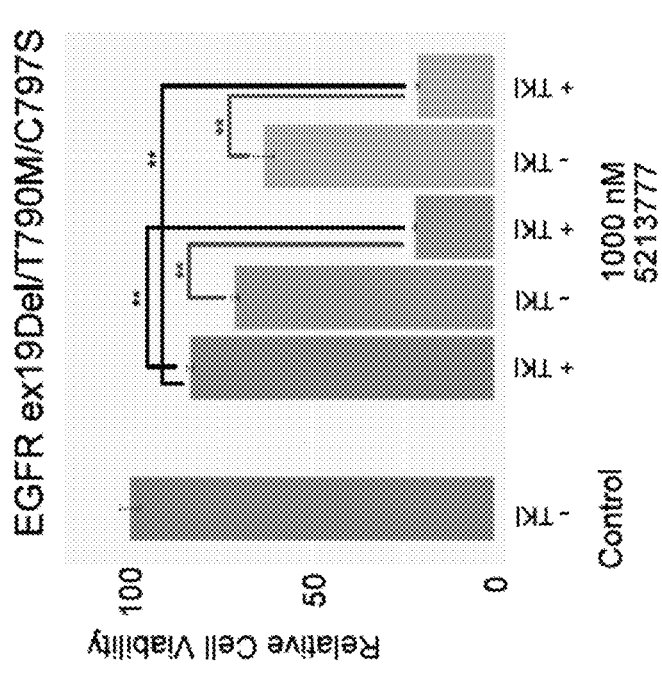
Figure 14D:
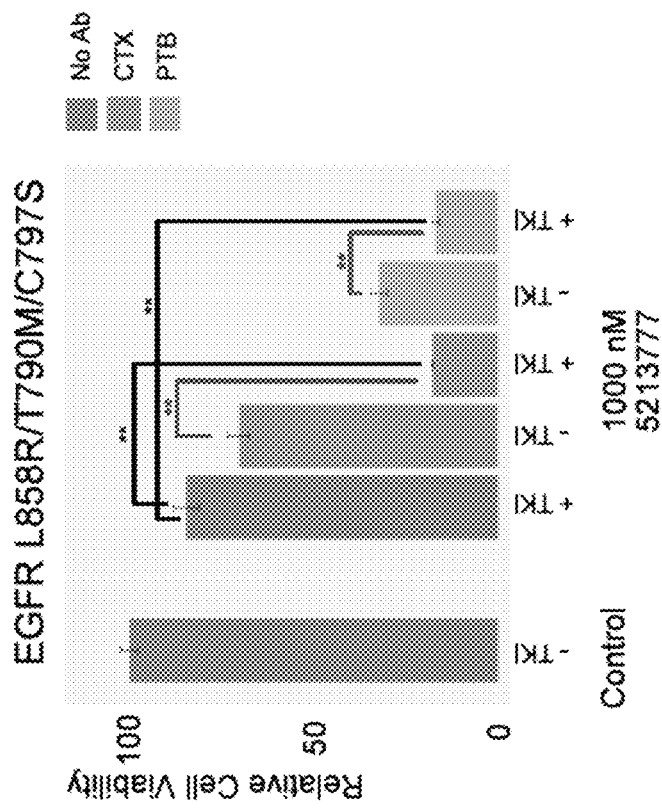
Figure 15B:
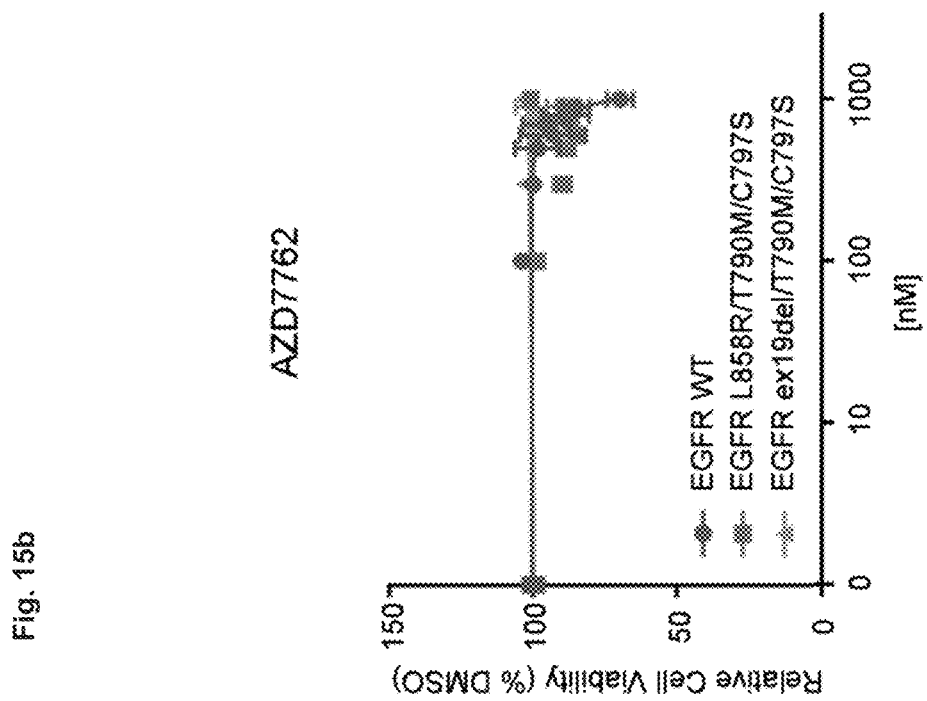
FIG. 15a-d Functional analysis of AZD7762 against EGFR C797S triple mutants. (a) Effects of AZD7762 on EGFR and downstream signalling molecule expression and phosphorylation in Ba/F3 cells expressing EGFR L858R/T790M/C797S, EGFRex19del/T790M/C797S or EGFRWT. (b) Effects of AZD7762 on viability of Ba/F3 cells expressing EGFR L858R/T790M/C797S, EGFR ex19del/T790M/C797S or EGFR WT. (c,d) Enhanced effect of AZD7762 in combination with 68 nM Cetuximab (CTX) or 140 nM Panitumumab on Ba/F3 EGFR L858R/T790M/C797S and EGFR ex19del/T790M/C797S cell viability. Statistical significance of differences in cell viability were determined using the Student's t-test. * and ** indicate a p-Value less than 0.05 and 0.01 respectively.
Figure 15A:
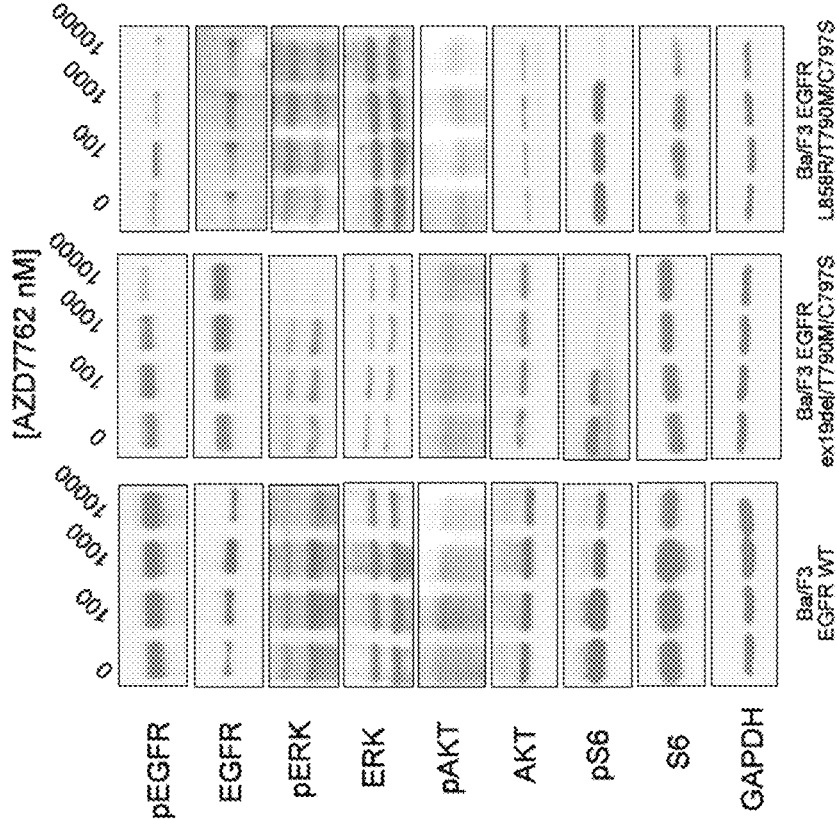
Figure 15D:
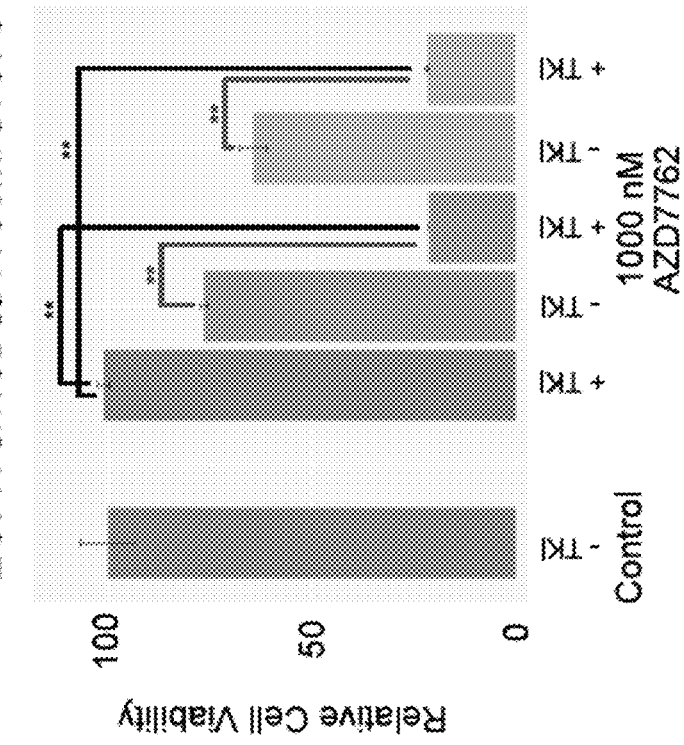
Figure 15C:
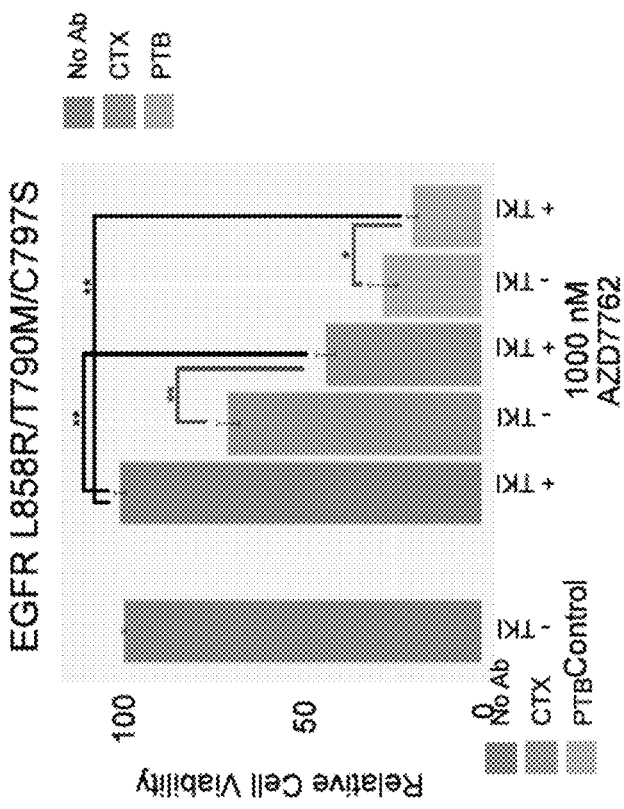

These 3 final candidates included the Chembridge Diverset compound 5213777 (3-(1,3-benzoxazol-2-yl)-7-(diethylamino)-2H-chromen-2-one), and the TKIs AZD7762 (OICR0001145B01) and Midostaurin (OICR0000317A01). There is little published information available for 3-(1,3-benzoxazol-2-yl)-7-(diethylamino)-2H-chromen-2-one and it is an example of a coumarin derivative. 7-Diethylamino-3(2'-benzoxazolyl)-coumarin has been reported as a microtubule inhibitor with antimitotic activity in multidrug resistant cancer cell lines[25]. Its specificity in the assay does not appear to be a consequence of any general activity against the viability of the reporter cell constructs used in the screen, however, as it has no substantial effect on the viability of either EGFR WT or EGFR L858R/T790M/C797S expressing cells (FIG. 12). In contrast to 3-(1,3-benzoxazol-2-yl)-7-(diethylamino)-2H-chromen-2-one, both TKIs have been well-studied. AZD7762 is a CHK1/2 kinase inhibitor, and has not been previously reported as active against EGFR NSCLC mutants. It has been the subject of a variety of studies, including a Phase I Clinical trial for the treatment of cancerous solid tumors[14,15]. Midostaurin (OICR0000317A01), is a multi-kinase inhibitor that has been recently approved by the FDA for use in the treatment of FLT3-mutant acute myeloid leukemia (AML)[16]. It was previously investigated for use against EGFR-L858R-T790M double mutant[17], however its activity has not been shown against EGFR-L858R-T790M-C797S triple mutant.

Figure 16A:
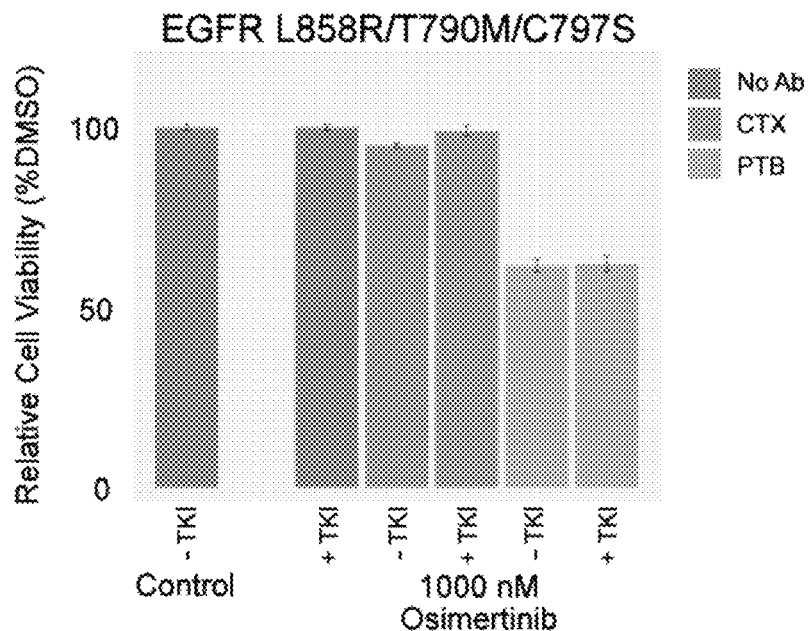
FIG. 16a-b Effect of Osimertinib on Ba/F3 cell viability in the presence of anti-EGFR therapeutic antibodies. (a,b) Osimertinib in combination with 68 nM Cetuximab (CTX) or 140 nM Panitumumab does not cause enhanced reduction of Ba/F3 EGFR L858R/T790M/C797S or EGFR ex19del/T790M/C797S cell viability, consistent with the inability of this compound to target C797S mutants.
Figure 16B:
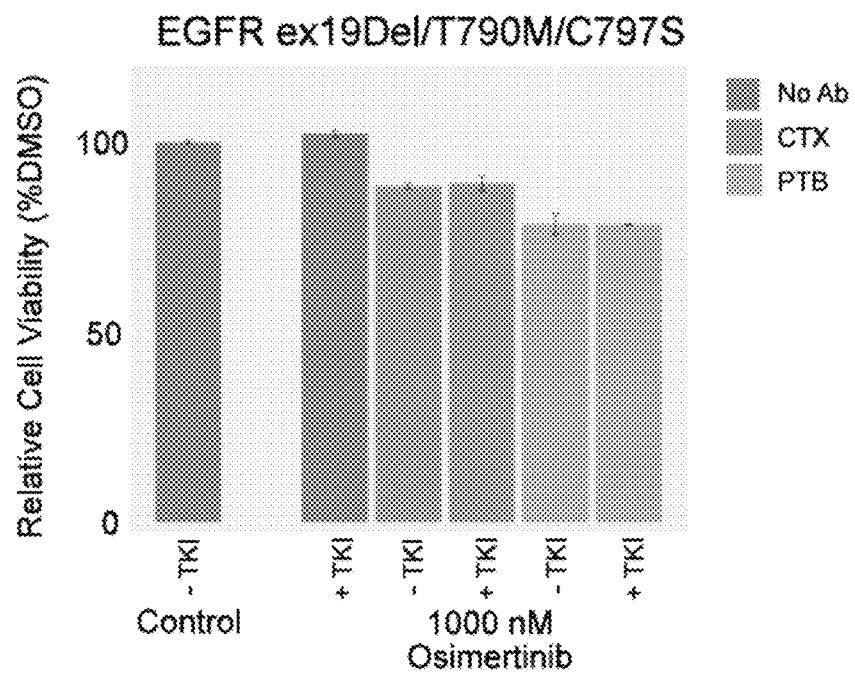

Further examination of these 3 final candidates was carried out in Ba/F3 cells expressing either EFGR-WT, EGFR-L858R-T790M-C797S or EGFR-ex19del-T790M-C797S (another common oncogenic variant of EGFR) (FIG. 13, FIGS. 14 and 15). Notably, all compounds had an effect on the phosphorylation and/or expression of EGFR and downstream signalling molecules in both mutant lines, but not in WT, with the strongest response observed for Midostaurin (FIG. 13a and FIGS. 14a and 15a). Midostaurin also caused a robust, dose-dependent reduction in the viability of Ba/F3 cells expressing mutant EGFR, much stronger than observed for WT (FIG. 13b), while 3-(1,3-benzoxazol-2-yl)-7-(diethylamino)-2H-chromen-2-one caused only a mild/modest reduction in cell viability of all three lines (with the greatest effect on EGFR-WT) (FIG. 14b), and AZD7762 had no strong effect on the viability of any of the cell lines tested (FIG. 15b). Strikingly, the potency of all three compounds against cell viability was significantly enhanced in the presence of the therapeutic anti-EGFR antibodies Cetuximab and Panitumumab in both EGFR-L858R-T790M-C797S (FIG. 13c, FIG. 14c and FIG. 15c) and EGFR-ex19del-T790M-C797S (FIG. 13d, FIG. 14d and FIG. 15d) triple mutants, similar to the behavior of Brigatinib (FIGS. 13c and d), a TKI recently shown to be effective against EGFR-C797S triple mutants alone and in combination with therapeutic antibody[18]. Interestingly, however, all three of our compounds displayed a notably enhanced potency against L858R triple mutant in the presence of Cetuximab that was not observed for Brigatinib, suggesting the compounds may have broader efficacy (compare FIG. 13c, FIG. 14c and FIG. 15c). Importantly, no such enhancement was evident using AZD9291 (Osimertinib), which does not target EGFR C797S mutants, as a control (FIG. 16).

Figure 17A:
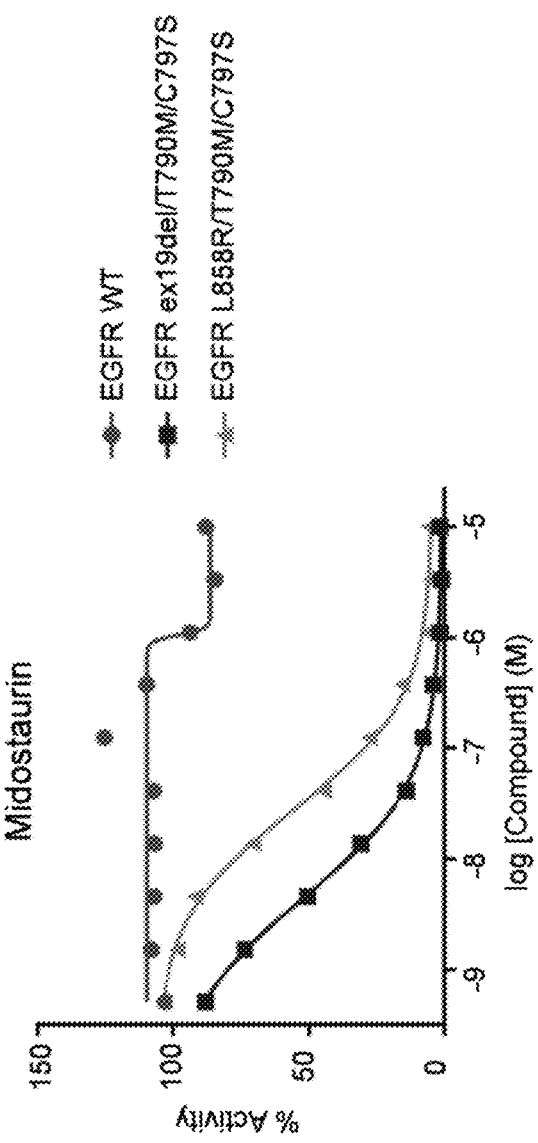
FIG. 17a-d In vitro kinase assays of identified compounds against EGFR WT and oncogenic triple mutants. (a) Midostaurin. (b) Brigatinib. (c) AZD7762. (d) Chembridge 5213777.
Figure 17B:
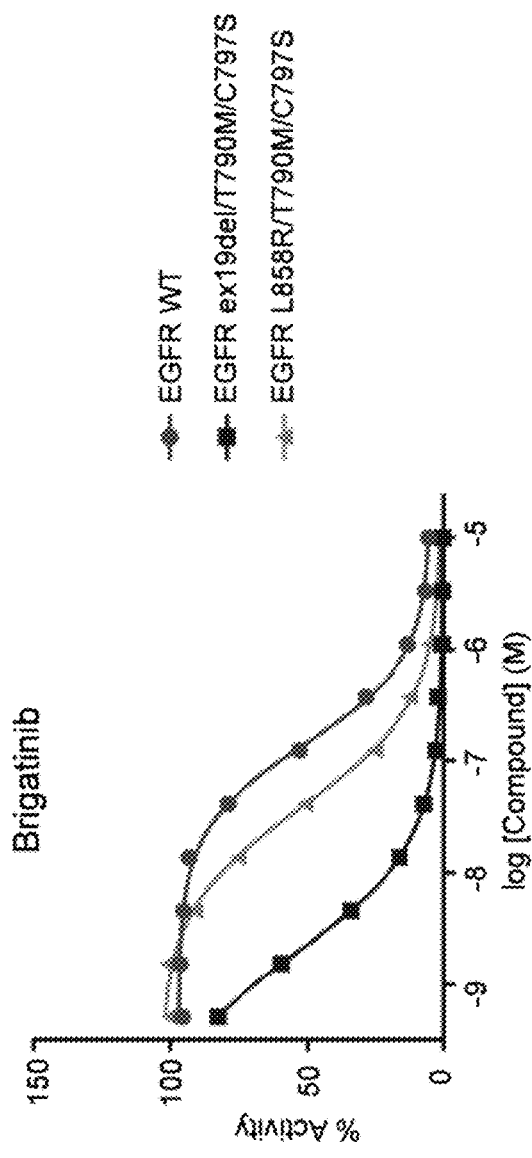
Figure 17C:
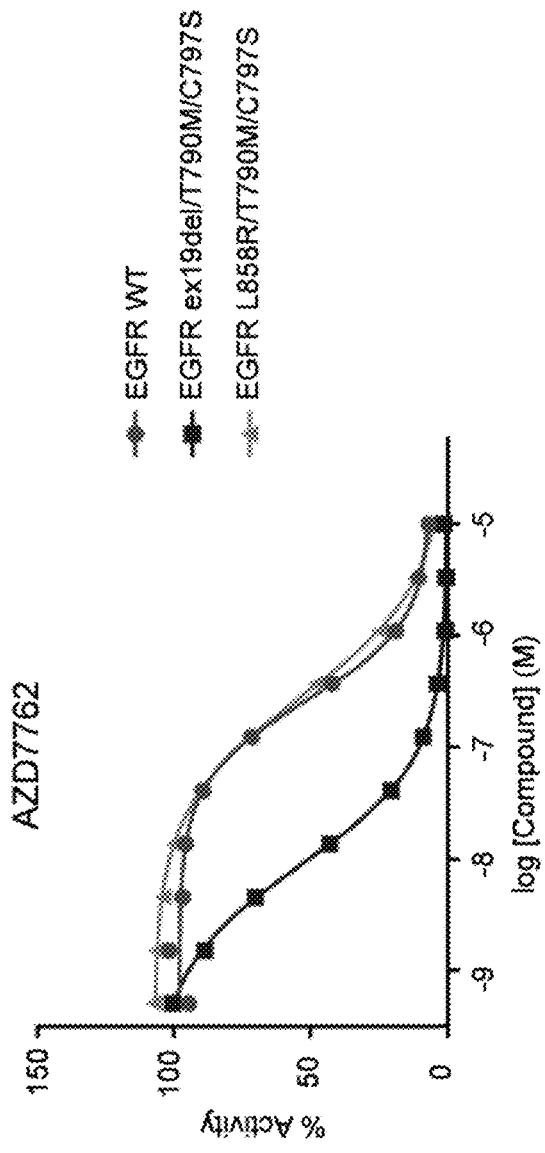
Figure 17D:
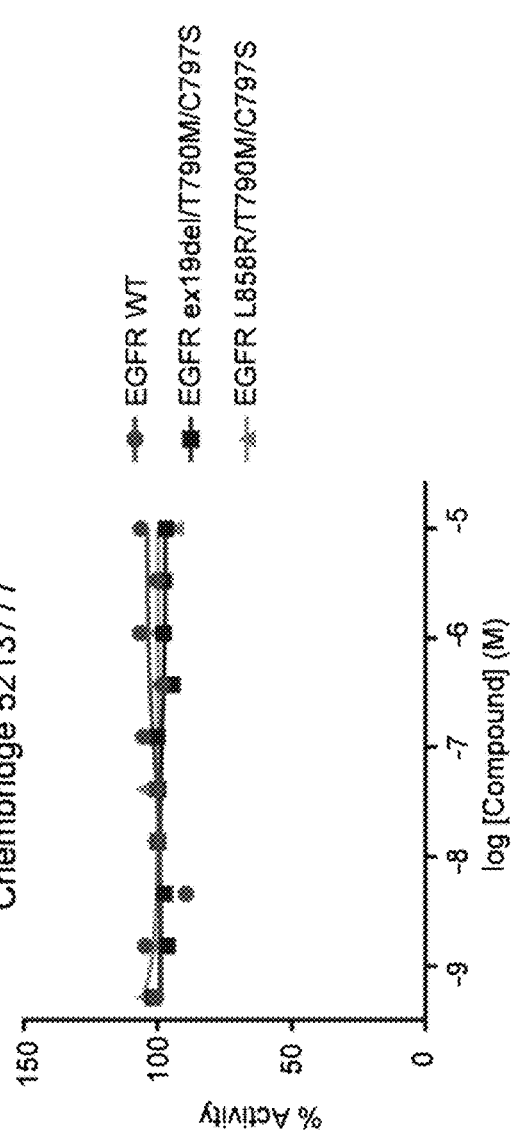

To obtain more information about the specific mechanism of action of the compounds against EGFR we next performed traditional in vitro kinase assays using recombinant kinase domain from the EGFR WT, EGFR ex19del/T790M/C797S and EGFR L858R/T790M/C797S proteins. In these assays, we observed that Midostaurin strongly inhibited the kinase activity of the EGFR triple mutants, but had no significant effect on EGFR WT activity, even at a concentration of 10 micromolar (FIG. 17a). This was in sharp contrast to Brigatinib, which although it was also a potent inhibitor of triple mutant, had a significant effect on EGFR WT activity, with an IC50 of ~141 nanomolar (FIG. 17b). AZD7762 also displayed expected kinase inhibition of EGFR triple mutants, with IC50s of ~89.3 and 282 nanomolar for the ex19del and L858R triple mutants, respectively, however, strikingly, its activity against the EGFR L858R mutant was comparable to that of WT (IC50 of ~258 nanomolar) (FIG. 17c). This is an intriguing result, suggesting that the specificity of the compound for EGFR L858R triple mutant over WT detected in our assay is a reflection of the use of the full-length protein and/or other conditions present only in a live-cell format, highlighting a potential strength of our system over traditional in vitro kinase assays, which would not have identified this specificity. Finally, 3-(1,3-benzoxazol-2-yl)-7-(diethylamino)-2H-chromen-2-one displayed no kinase inhibitory activity against EGFR WT or either of the EGFR triple mutants (FIG. 17d), consistent with the fact that it has no previously reported activity against kinases, and lacks a classic kinase inhibitor pharmacophore. While the mechanism of action of this compound is unclear, its detection in our MaMTH-DS assay using EGFR L858R/T790M/C797S as bait, its effect on the phosphorylation of EGFR and downstream signalling molecules in Ba/F3 cells expressing both EGFR ex19del/T790M/C797S and L858R/T790M/C797S triple mutants (but not WT), and its enhanced potency against triple mutant Ba/F3 cells in the presence of anti-EGFR therapeutic antibodies, clearly supports an EGFR specific involvement. Exactly how this compound targets EGFR mutant, including possible roles as an allosteric inhibitor or a direct disruptor or EGFR interactions, will be the focus of future studies.

MaMTH as demonstrated herein can sensitively detect inhibitory compounds that change the phosphorylation status of full-length EGFR proteins in the context of living cells and in the low nanomolar range, with the benefit that identified small molecule candidates have already passed cell permeability and toxicity tests.

Methods

MaMTH assays. Cells stably expressing bait of interest (EGFR, MET, FGFR4, ALK, AXL) were seeded into 96-well TC-treated plates and grown at 37° C./5% $CO_2$ overnight in DMEM/10% FBS/1% PS to ~50-60% confluency. Cells were transfected with 50 ng/well of Nub-Shc1 'prey' protein by calcium phosphate precipitation. Five hours after transfection, media was aspirated out and cells were treated with 100 uL of fresh media containing specific compound and 0.5 ug/ml of tetracyline to induce bait expression. After 24 hours, luciferase activity was measured by chemoluminescence.

Western analysis of bait and downstream signalling molecule expression and phosphorylation. Cells grown under the specified conditions were washed with ice cold PBS before addition of the cell lysis buffer (Cell Lysis Buffer 10×, Cell Signalling Technology, #9803) supplemented with protease inhibitors. Lysates were transferred to 1.5 mL microtubes, and centrifuged for 15,000 rpm for 10 min. The supernatants were mixed with Laemmli sample buffer, and boiled at 95° C. for 5 min. Protein quantification was performed using the BCA Protein Assay Reagent (Pierce) according to the manufacturer's protocol prior to addition of sample buffer. Western blot analyses were performed after separation by SDS-PAGE, and transferred to nitrocellulose membranes. The membranes were then blocked with 2% BSA in Tris-buffered saline/Tween 20 (TBS-T). Antibodies used for Western blot analysis were: phospho-EGFR antibody (Tyr1173; Santa Cruz, sc101668, 1:10,000), total EGFR (Cell signalling Technology, #4267, 1:10,000), phospho-AKT (Ser473; Cell Signalling Technology, #4060, 1:10,000), total AKT (Cell signalling Technology, #4691, 1:10,000), phospho-ERK (Thr202/Tyr204; Cell Signalling Technology, #9101, 1:10,000), total ERK1/2 (Cell Signalling Technology, #9102, 1:10,000), phospho-S6 (Ser240/244, Cell Signalling Technology, #5364, 1:10,000), total S6 (Cell Signalling Technology, #5364, 1:10,000), anti-GAPDH (Santa Cruz, 1:10,000), anti-tubulin (Santa Cruz, 1:10,000) or anti-VS (Cell Signalling Technology, 1:10,000).

Cell viability assays. MaMTH stable bait cells or Ba/F3 cells were seeded into 96 well plates at 10,000 cells per well. For MaMTH stable cells, the cells were treated the next day with each inhibitor in a dose-dependent manner in addition to 0.5 ug/mL tetracyline to induce bait expression. For BaF3 cells, the cells were treated with each compound the same day as seeding. After 72 hours of drug treatment, cell viability was measured using the CellTiter-Glo assay (Promega).

EGFR localization and trafficking analyses. The experiment was performed in 384 well CellCarrier imaging plates. Each condition (EGF stimulation time, treatment and mutation) was repeated in at least 6 wells. 11 images (276×234 µm) were collected from each well by automated confocal microscope CV7000 (Yokogawa) with a 60× water immersion objective (NA=1.2), with a total of 1063±251 (mean±SD) imaged cells per well. Images were analyzed by MotionTracking software (http://motiontracking.mpi-cbg.de) and 147±80 (mean±SD) EEA1-positive endosomes per cell were found. All statistics were calculated per image, then averaged between images in the well, and, finally, averaged between wells of equal conditions. The SEM was calculated from the last averaging step.

Generation of adherent HEK293 cells. Flp-In 293 TREx cells (Thermo Fisher) were grown at 37° C./5% $CO_2$ in DMEM/10% FBS/1% PS media in 6-well TC-treated plates to ~50-60% confluency. Cells were then transfected with pcDNA3.1 plasmid, expressing the gene for human Macrophage Scavenger Receptor 1 (MSR1) transcript variant A alongside G418 resistance cassette, using PolyJet transfection reagent (SignaGen), as per manufacturer instructions. Cells were grown overnight and then split into 10 cm plate containing 10 mL of DMEM/10% FBS/1% PS/800 ug/mL G418 and grown at 37° C./5% $CO_2$ until distinct foci appeared. Individual foci were expanded, and screened for enhanced adherence using methylene blue staining and stringent washing in a 96-well plate format as previously described[10]. The most highly adherent cell line displaying robust growth in media and appropriate Flp-In 293 TREx resistance to Zeocin and Blasticidin was selected for use in the generation of MaMTH reporter cells.

Generation of stable MaMTH reporter cells. Reporter vector was generated in a pcDNA3.1(-) backbone using ORFs expressing *Gaussia princeps* luciferase (New England Biolabs) under the control of a 5×GAL4 UAS and puromycin resistance marker under the control of a constitutive PGK promoter, via Gibson assembly[19]. Adherent FLP-compatible HEK293 cells (prepared above) were grown at 37° C./5% $CO_2$ in DMEM/10% FBS/1% PS media in 6-well TC-treated plates to ~50-60% confluency. Cells were transfected with 1000 ng reporter vector using X-tremeGENE 9 DNA transfection reagent (Roche) as per manufacturer instructions. After 5 hours, media containing transfection reagent was removed and replaced with fresh DMEM/10% FBS/1% PS. Cells were grown for 48 hours and then split 1 in 2 into new 6-well plates using DMEM/10% FBS/1% PS+0.5 ug/mL puromycin and grown until individual foci appeared. Individual foci were expanded and monoclonal populations isolated by sorting of individual cells into 96-well plates using a FACS Aria II Flow Cytometer (BD Biosciences), followed by further expansion. Expanded cell populations were screened individually and a cell line displaying strong MaMTH-responsive reporter activity and minimal background was selected for further use in MaMTH-DS.

Generation of Flp-In TREx compatible MaMTH bait vectors. Gateway-cloning cassette followed by Cub-GAL4/RelA TF sequence was PCR-amplified off of our previously reported MaMTH bait vectors using KAPA 2×HiFi DNA Polymerase (Kapa Biosystems). Amplified fragment was combined with EcoRV-digested Flp-compatible pcDNA5/FRT/TO vector (Thermo Fisher) via Gibson Assembly[19]. Generated constructs were fully sequenced verified, and construct containing all of the elements necessary for Gateway Cloning, tetracycline-induction, MaMTH bait C-tagging and use in generation of isogenic stables via the Flp-In TREx system tetracyline-inducible, was isolated. This final bait vector construct was designated A1160.

Generation of Flp-In TREx compatible MaMTH bait constructs. All bait and prey constructs were generated using the Gateway cloning technology (Thermo Fisher) and destination vectors A1160 (MaMTH bait) or A1245 (MaMTH prey). Shc1 ORF in entry clone format was obtained from the Human ORFeome Collection V8.1[20]. EGFR-WT and single L858R and double L858R/T790M mutant entry clones were generated as described previously[1]. EGFR triple mutant containing the C797S mutation was generated via site-directed mutagenesis of EGFR double mutant using primers 5'-atgcccttcggcagcctcctggact-3' and 5'-agtccaggaggctgccgaagggcat-3' (SEQ ID NO: 1 and 2). MET entry clone was obtained from OpenFreezer (V9936). All final bait and prey constructs were fully sequence verified.

Generation of stable MaMTH bait cell lines. Isogenic MaMTH reporter cell lines stably expressing baits of interest were generated using the Flp-In TREx system (Thermo Fisher). Briefly, MaMTH reporter cells were grown at 37° C./5% $CO_2$ in DMEM/10% FBS/1% PS media in 6-well TC-treated plates to ~50-60% confluency. Cells were transfected with 900 ng pOG44 and 100 ng of bait construct in A1160 using X-tremeGENE 9 DNA transfection reagent (Roche) as per manufacturer instructions. After 5 hours, media containing transfection reagent was removed and replaced with fresh DMEM/10% FBS/1% PS. Cells were grown for 48 hours and then split 1 in 2 into new 6-well plates using DMEM/10% FBS/1% PS+100 ug/mL Hygromycin and grown until individual foci appeared. Foci were expanded and proper, tetracycline-induced bait expression was verified by Western blotting.

MaMTH-DS high-throughput screening workflow. MaMTH reporter cells stably expressing EGFR/L858R/T790M/C797S bait were seeded into 384-well plates (5000 cells/well) in DMEM/10% FBS/1% PS media using a MultiDrop Combi (Thermo) fitted with a standard cassette. Plates were covered with MicroClime Environmental Lids (Labcyte; hydrated with ~10 mL ddH2O) and grown at 37° C./5% $CO_2$ overnight. The next day cells were transfected with 25 ng of MaMTH Shc1 prey DNA using X-X-tremeGENE 9 DNA transfection reagent (Roche) as per manufacturer instructions. Transfection mix (5 uL total volume/well) was added to 384-well plates containing cells using a Bravo Automated Liquid Handling Platform (Agilent) fitted with a 96ST pipette head. Plates were once again covered with MicroClime Lids and grown at 37° C./5% $CO_2$ for 5 hours. Media was then removed from plates using a BioTek 405 Select microplate washer, and a fresh 50 uL of DMEM/ 10% FBS/1% PS media containing 0.5 ug/mL Tetracycline was added to each well using a MultiDrop Combi. 50 nL of DMSO, AZD9291 (70 uM) or library compound (10 mM for Chembridge/Maybridge compounds, 1 mM for TKIs were then added to individual wells using an ECHO 550 (Labcyte) (the final concentration of for the Chembridge/ Maybridge compounds was 10 uM and 1 uM for the TKIs). Plates were covered with MicroClime lids and grown for an additional 17-18 hours at 37° C./5% $CO_2$. Cells were then subjected to luciferase assay using 20 uL of 20 uM coelenterazine per well. Luminescence was measured in an injector-equipped SynergyNeo microplate reader, using linear shaking for 2 seconds after substrate addition. All reads were performed from the top using a Gain of 100 and a 1 second integration time.

Data analysis of MaMTH-DS screening results. All data was analysis was performed in an automated fashion using in house-software developed in the R programming language[21]. Raw data from screens were subjected to Box-Cox transformation as previously described[11] in order to improve data distribution symmetry and normality. Z-prime[12] values were calculated on a per plate basis using EGFRL858R-T790M and EGFR-L858R-T790M-C797S in the presence of AZD9291 as positive and negative controls respectively (with the exception of Shc1 Round 2 Plate 10, where, due to a technical issue, EGFR-L858R-T790M-C797S in the presence of DMSO was used as a negative control instead). Prior to Z' calculations, the single most extreme value from each control dataset was excluded if it was classified as a outlier based on a cut-off of 1.5 times the IQR. Data normalization was performed using both controls-based Normalized Percent Inhibition (NPI) and sample-based (controls independent) BScore. NPI was calculated as (Negative Control Signal Sample Signal)/(Negative Control Signal Positive Control Signal)*100. B-Score was calculated using the cellHTS2 package[22]. NPI was plotted against BScore and hits were scored using a combined cut-off of 70% NPI and a BScore of −3 or less.

In vitro Kinase assays. Kinase assays were performed using recombinant proteins of the kinase domain of wild-type EGFR, EGFR-C797S/T790M/L858R, EGFR-C797S/ T790M/ex19del, and EGFR-C797S (Reaction Biology Corporation). Compounds (Midostaurin, AZD7762, Chembridge 5213777 and Brigatinib) were tested in a 10-dose IC50 duplicate mode with 3-fold serial dilution starting at 10 μM. Reactions were carried out at 10 μM ATP.

Example 3

Figure 18A:
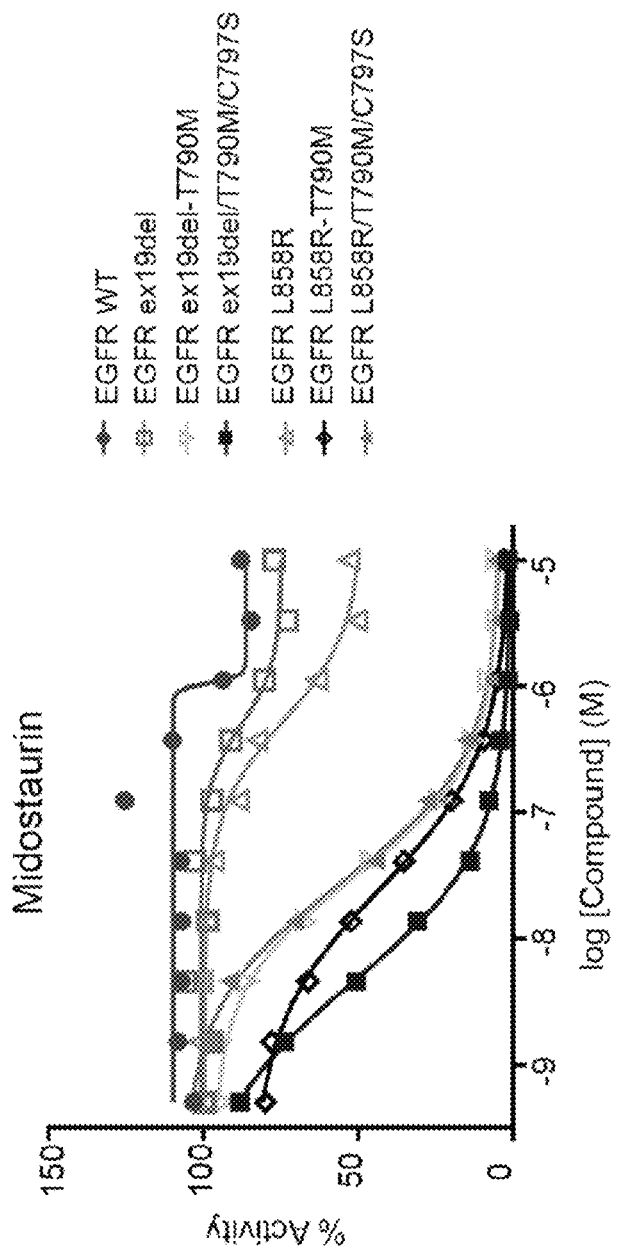
FIG. 18a-b Effect of Midostaurin on EGFR kinase activity and signalling. (a) Midostaurin inhibits the kinase activity of EGFR double and triple mutants. (b) Midostaurin inhibits EGFR activation and downstream signaling in PC9 EGFR ex19del/T790M/C797S cells.
Figure 18B:
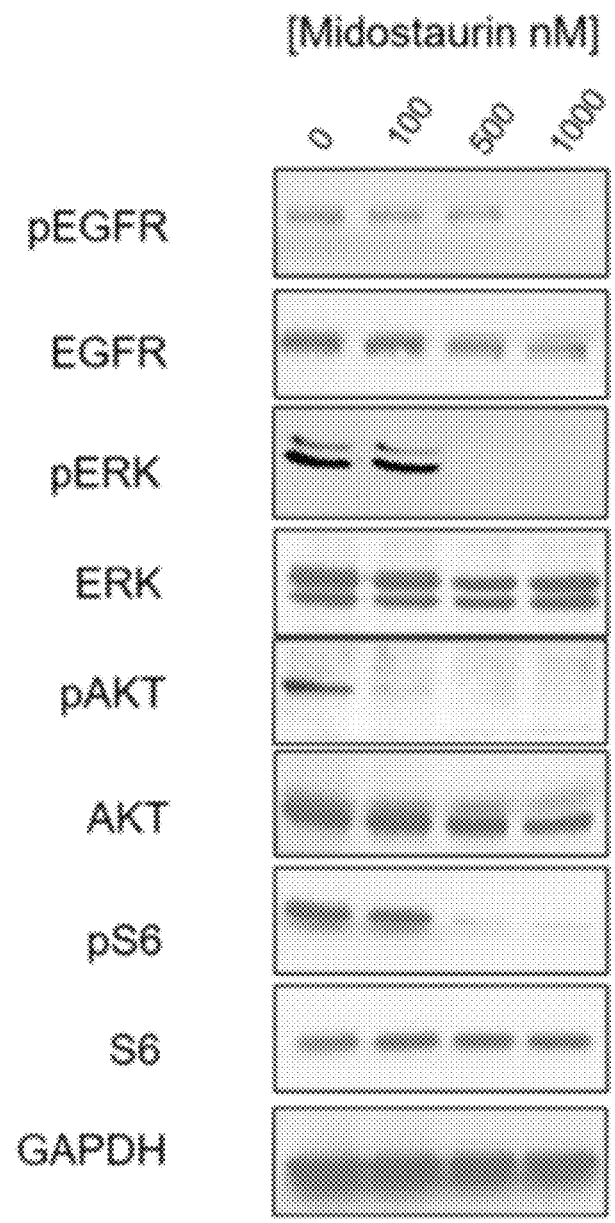
Figure 19A:
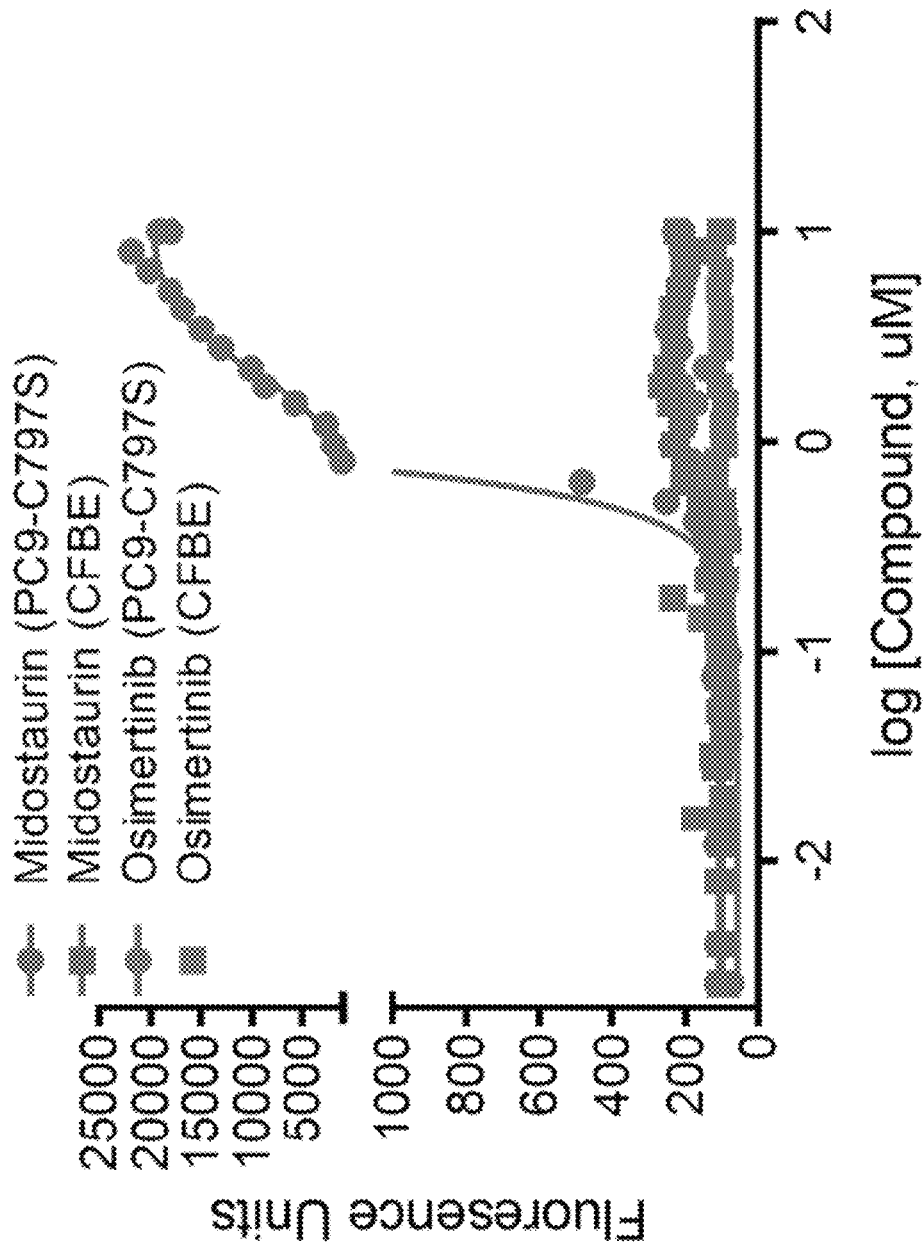
FIG. 19a-b Effect of Midostaurin on PC9 cells expressing EGFR C979S triple mutants. (a) Midostaurin, but not Osimertinib, activates caspase 3 and 7 activity in PC9 EGFR ex19del/T790M/C797S cells but not CBFE cells. (b) Midostaurin, but not Osimertinib, reduces the viability of PC9 EGFR ex19del/T790M/C797S organoids.
Figure 19B:
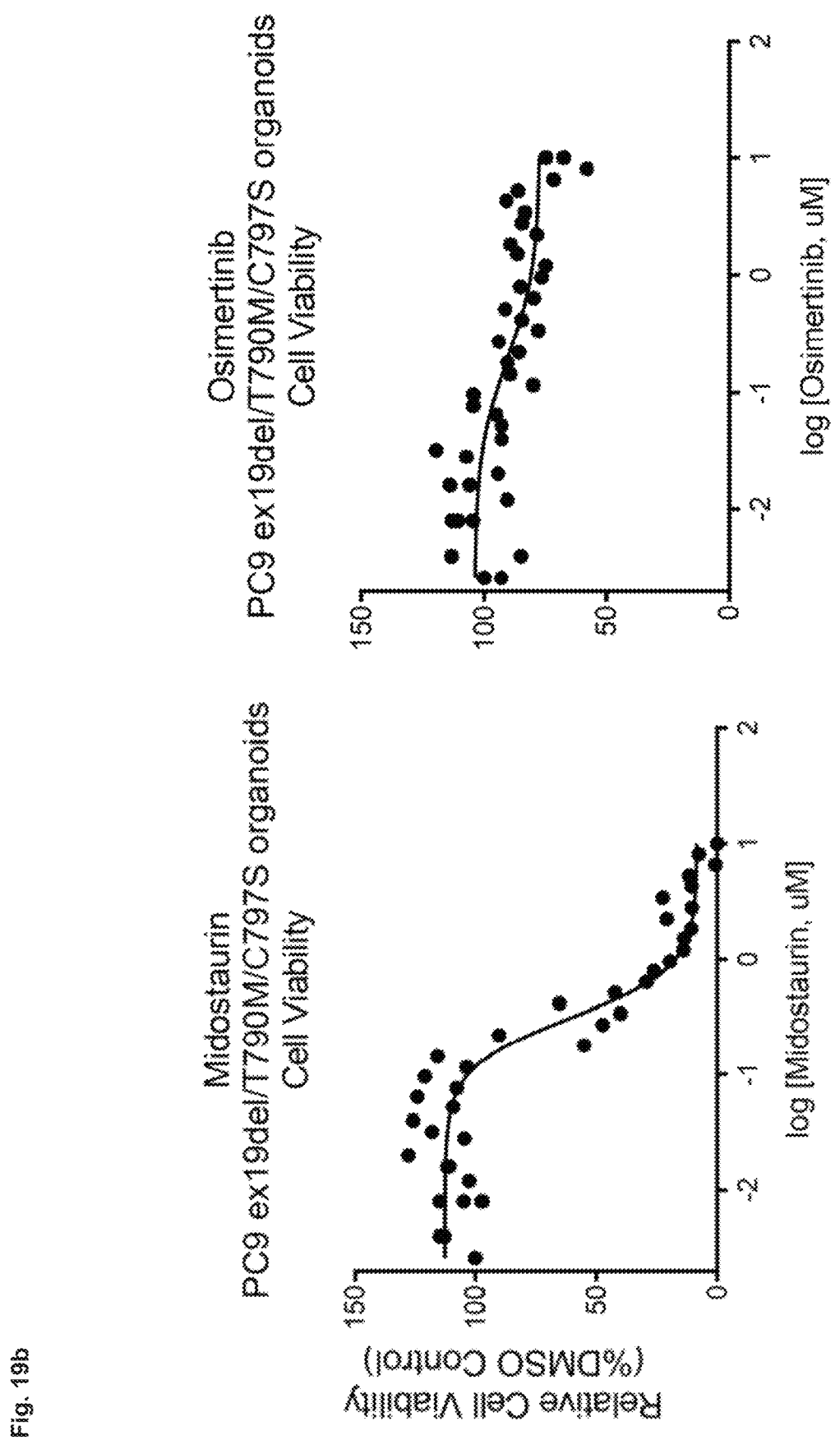

Further examination of the effects of midostaurin on mutant EGFR activity was carried out. In vitro kinase assays demonstrated that that midostauin inhibits the kinase activity of EGFR double and triple mutants (FIG. 18a). Examination of the effects of midostaurin on mutant EGFR activation and downstream signaling was carried out in PC9 cells expressing EGFR-ex19del-T790M-C797S (FIGS. 18b and 19). Midostaurin had an inhibitory effect on the phosphorylation and/or expression of EGFR and downstream signaling molecules (FIG. 18b). Midostaurin caused a dose-dependent activation of caspase 3 and 7 activity that was not observed either in CFBE cells or in response to osimertinib (FIG. 19a). Midostaurin also caused a dose-dependent reduction in viability of PC9 organoids expressing EGFR-ex19del-T790M-C797S that was not observed for osimertinib (FIG. 19b).

Figure 20A:
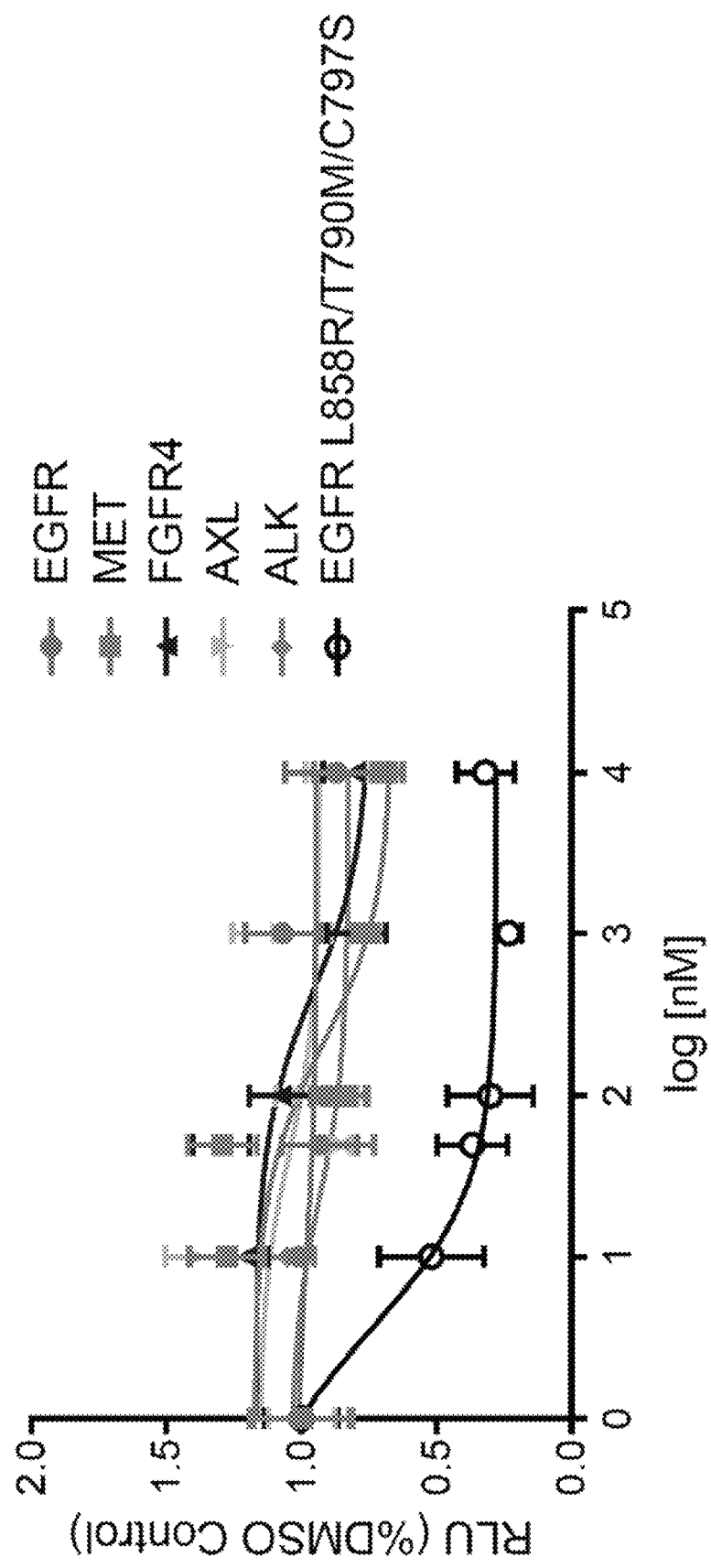
FIG. 20a-c Effect of 5213777 on MaMTH-DS signal, EGFR kinase activity and downstream signalling. (a) 521377 inhibits the interaction between Shc1 and EGFR L858R/T790M/C797S but not EGFR WT, MET, FGFR4, AXL or ALK. (b) 521377, but not Osimertinib, inhibits the interaction between EGFR L858R/T790M/C797S and Shc1, CrkII and Hsp90. (c) 521377 does not inhibit the kinase activity of EGFR L858R/T790M/C797S or EGFR ex19del/T790M/C797S in in vitro kinase assays.
Figure 20B:
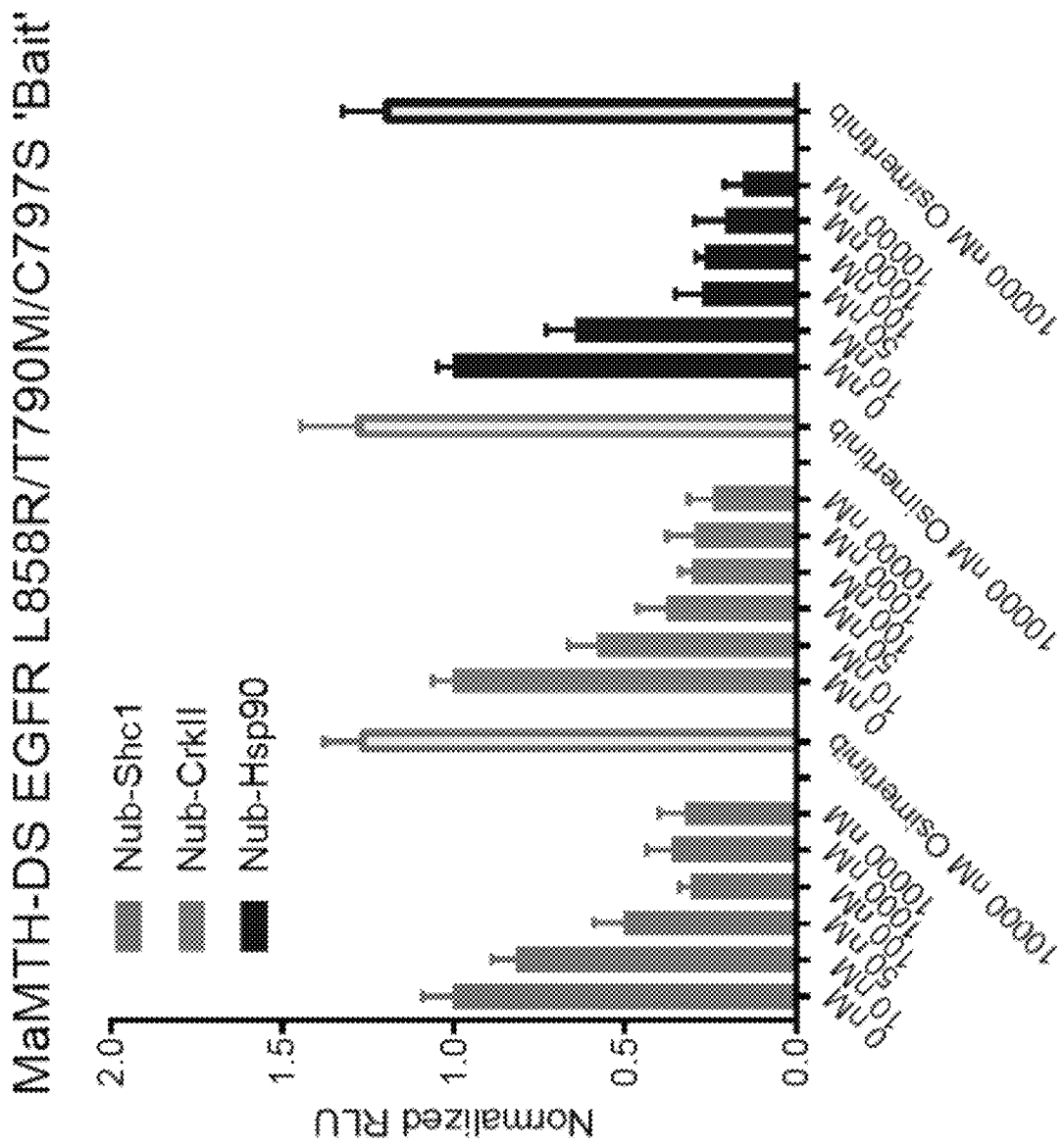
Figure 20C:
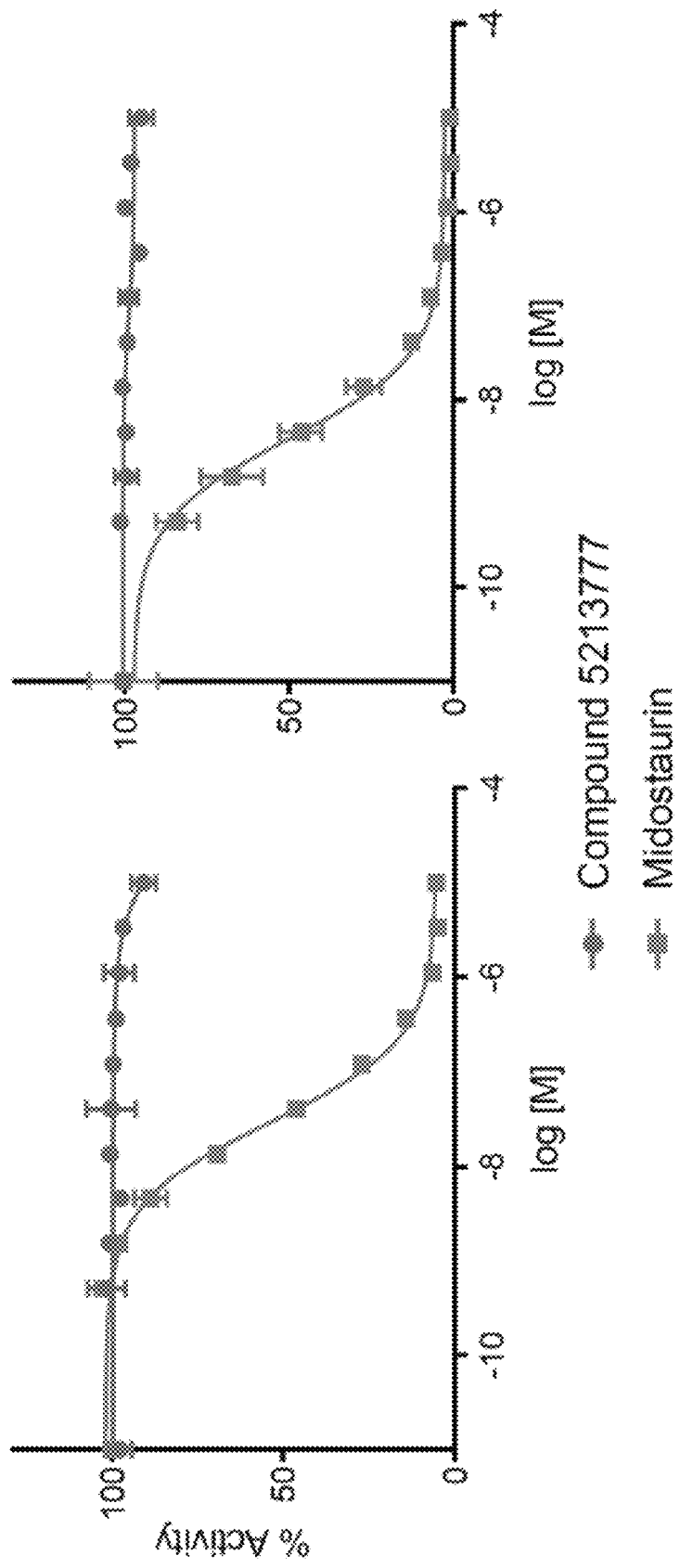
Figure 21A:
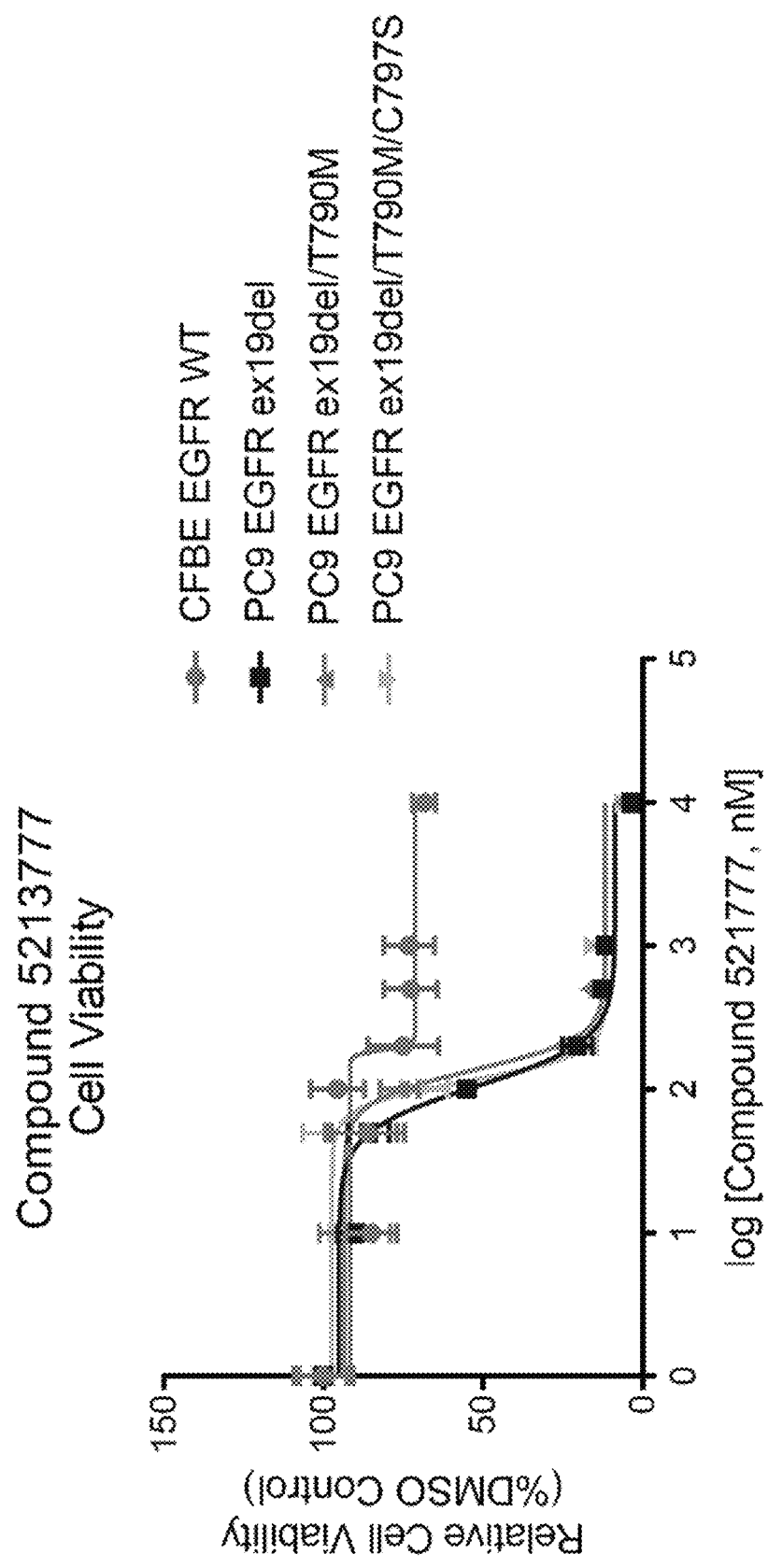
Figure 21B:
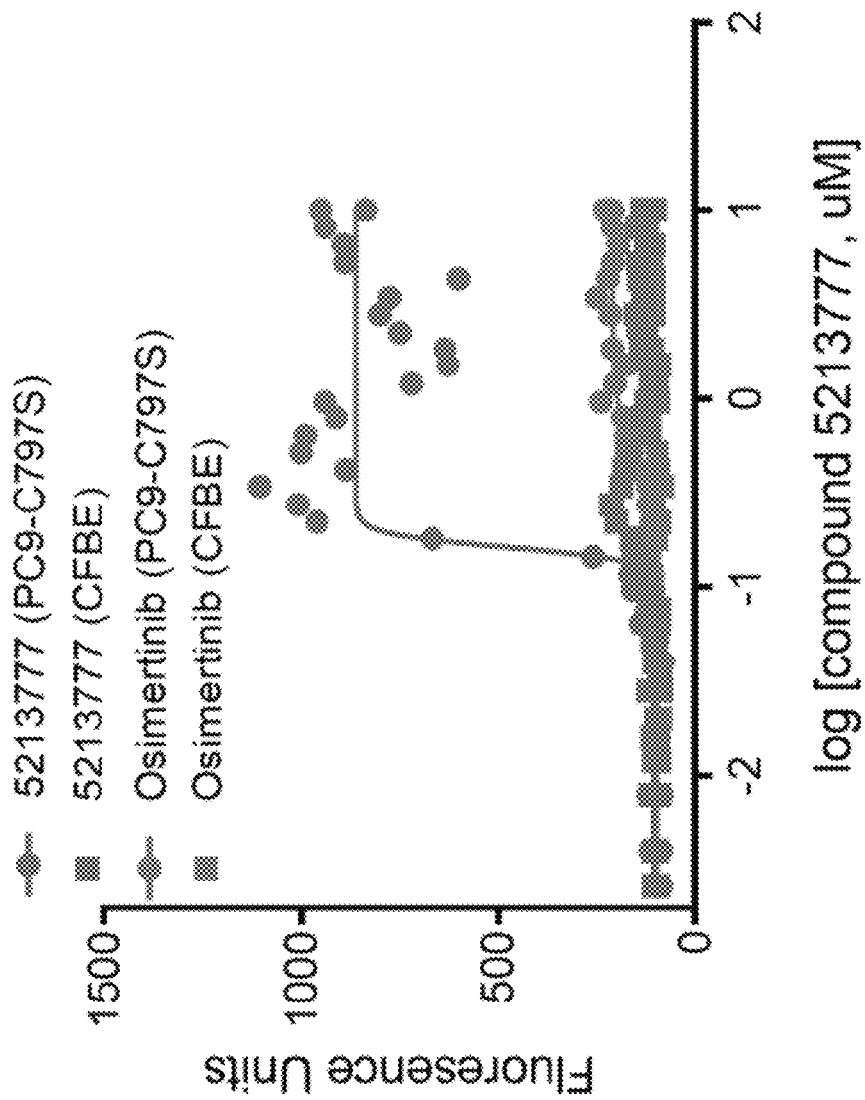
Figure 21D:
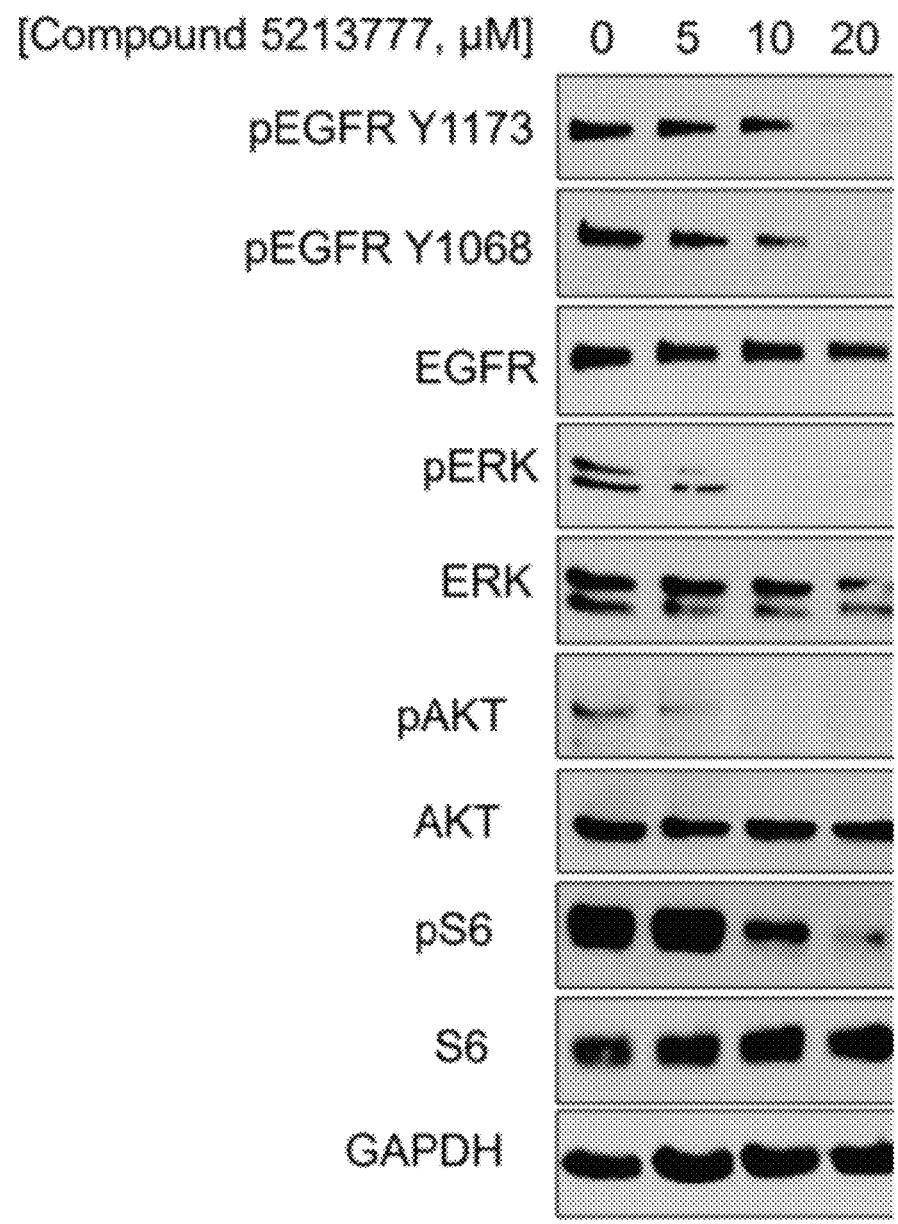

Further examination of the effects of 3-(1,3-benzoxazol-2-yl)-7-(diethylamino)-2H-chromen-2-one was carried out. The ability of 3-(1,3-benzoxazol-2-yl)-7-(diethylamino)-2H-chromen-2-one to inhibit complex formation was tested using MaMTH (FIGS. 20a and b). 3-(1,3-benzoxazol-2-yl)-7-(diethylamino)-2H-chromen-2-one blocked complex formation between Shc1 and EGFR L858R/T790M/C797S but not wild-type EGFR or the other tested RTKs (FIG. 20a). 3-(1,3-benzoxazol-2-yl)-7-(diethylamino)-2H-chromen-2-one, but not osimertinib, blocked complex formation between EGFR L858R/T790M/C797S and Shc1, CrkII, and Hsp90 in a dose-dependent manner (FIG. 20b). In vitro kinase assays demonstrated that that 3-(1,3-benzoxazol-2-yl)-7-(diethylamino)-2H-chromen-2-one does not inhibit the kinase activity of EGFR triple mutants (FIG. 20c). Examination of the effects of 3-(1,3-benzoxazol-2-yl)-7-(diethylamino)-2H-chromen-2-one on mutant EGFR activation and downstream signaling was carried out in PC9 cells expressing EGFR-ex19del-T790M-C797S (FIGS. 20d and 21). 3-(1,3-benzoxazol-2-yl)-7-(diethylamino)-2H-chromen-2-one had an inhibitory effect on the phosphorylation and/or expression of EGFR and downstream signaling molecules (FIG. 20d). 3-(1,3-benzoxazol-2-yl)-7-(diethylamino)-2H-chromen-2-one caused a dose-dependent decrease in viability in PC9 cells expressing EGFR-ex19del, EGFR-ex19del-T790M, or EGFR-ex19del-T790M-C797S mutants that was not observed either in CFBE cells expressing wild-type EGFR (FIG. 21a). 3-(1,3-benzoxazol-2-yl)-7-(diethylamino)-2H-chromen-2-one caused a dose-dependent activation of caspase 3 and 7 activity in PC9 cells expressing EGFR-ex19del-T790M-C797S mutants that was not observed either in CFBE cells or in response to osimertinib (FIG. 21b). 3-(1,3-benzoxazol-2-yl)-7-(diethylamino)-2H-chromen-2-one also caused a dose-dependent reduction in viability of PC9 organoids expressing EGFR-ex19del-T790M-C797S that was not observed for osimertinib (FIG. 19b).

Briefly, PC9 EGFR ex19del/T790M/C797S organoids were developed by the Princess Margaret Living Biobank Organoid Center. Briefly, cells were adapted to grow in a Matrigel culture and were seeded into 384 well plates for the cell viability assay. Organoids were allowed to grow for 72 hours with the compound, and cell viability was measured using CellTitre glow cell viability reagent.

Example 4

The success of midostaurin in the above examples prompted a search for other molecules with similar activity. Gilteritinib is another FLT3 inhibitor that has been proposed for use in Acute Myeloid Leukemia patients harboring a FLT3 mutation. Gilteritinib was therefore tested for the ability to inhibit EGFR mutants.

Figure 22A:
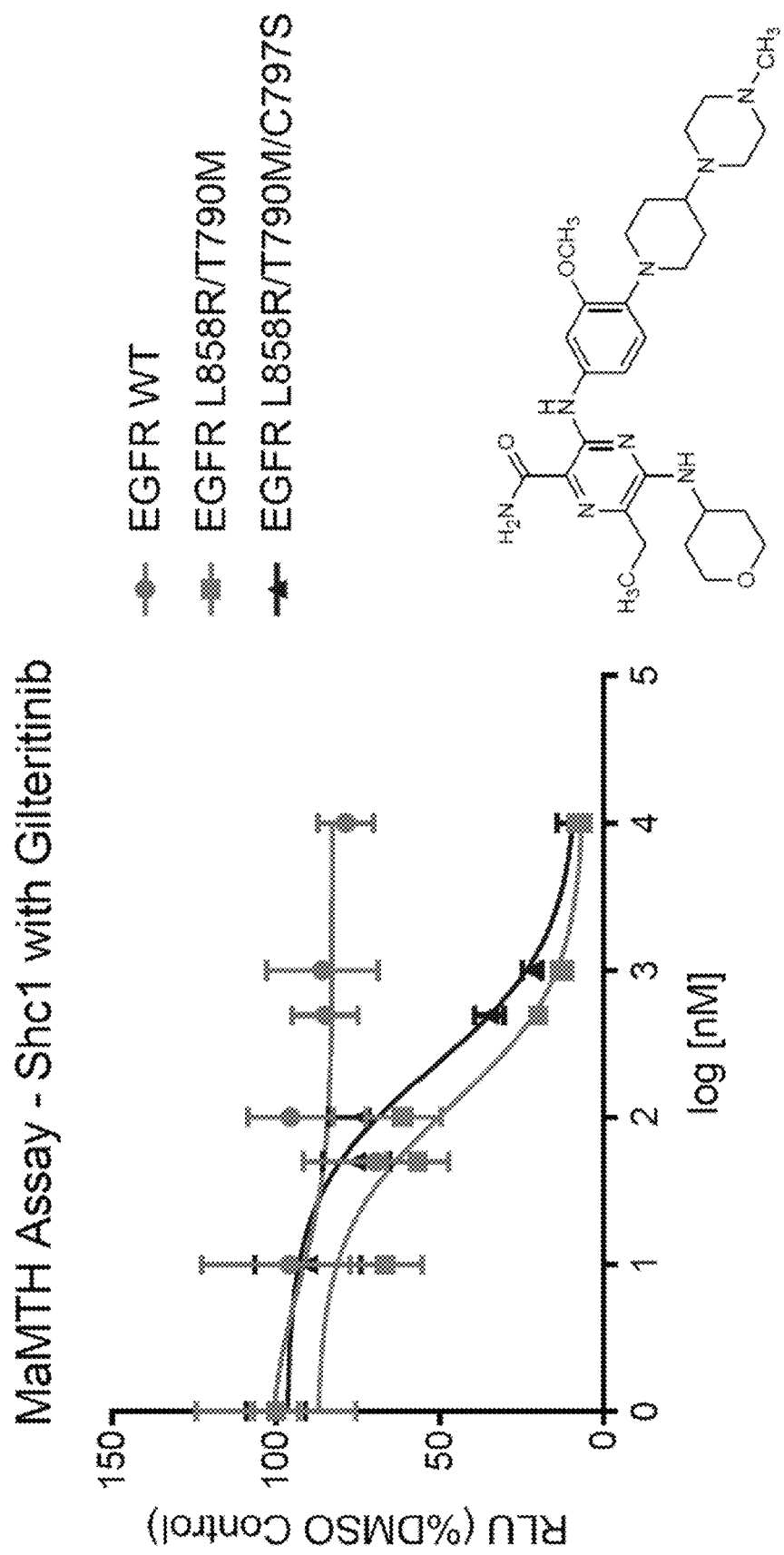
FIG. 22a-c Effect of Gilteritinib on MaMTH-DS signal, EGFR kinase activity and downstream signalling. (a) Gilteritinib preferentially inhibits the interaction between Shc1 and EGFR L858R/T790M or EGFR L858R/T790M/C797S but not EGFR WT. (b) Gilteritinib inhibits the kinase activity of EGFR L858R/T790M/C797S, EGFR ex19del/T790M and EGFR ex19del/T790M/C797S in in vitro kinase assays. (c) Gilteritinib inhibits EGFR activation and downstream signaling in PC9 EGFR ex19del/T790M/C797S cells.
Figure 22B:
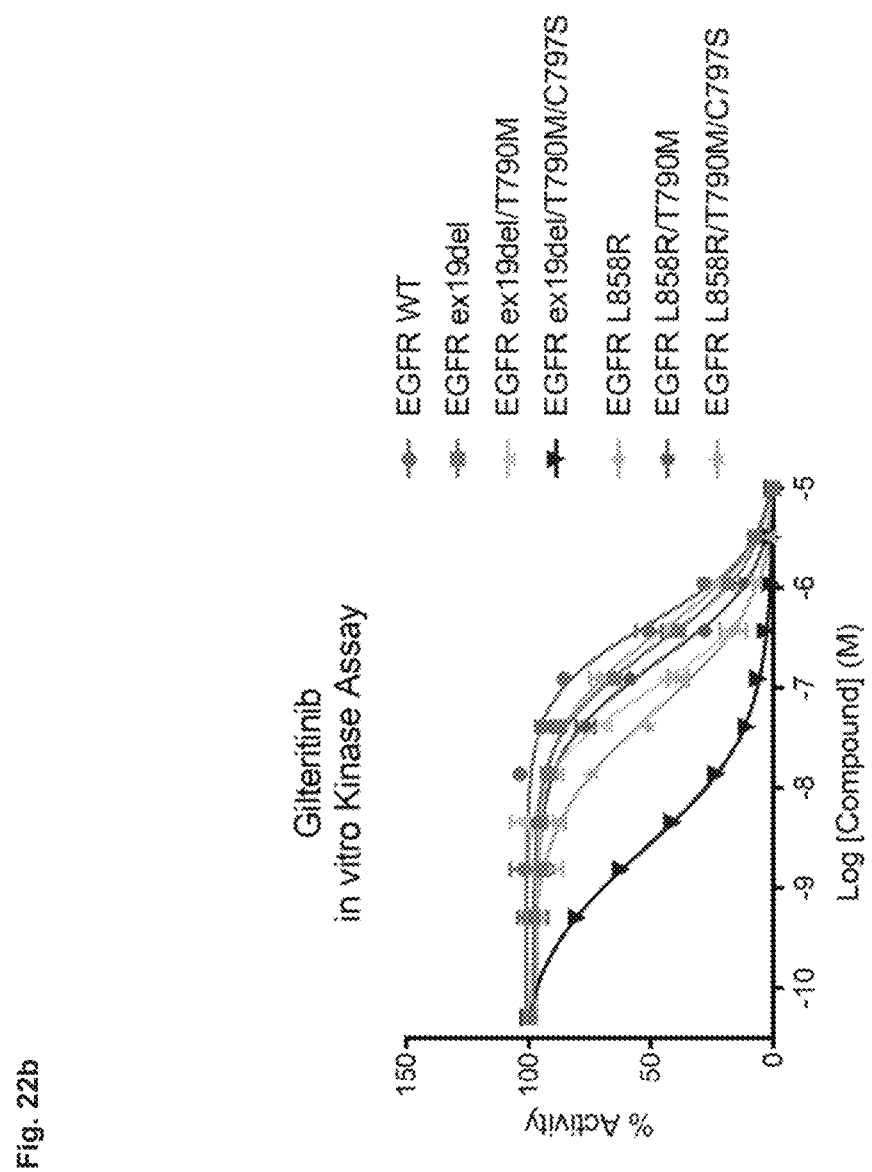
Figure 22C:
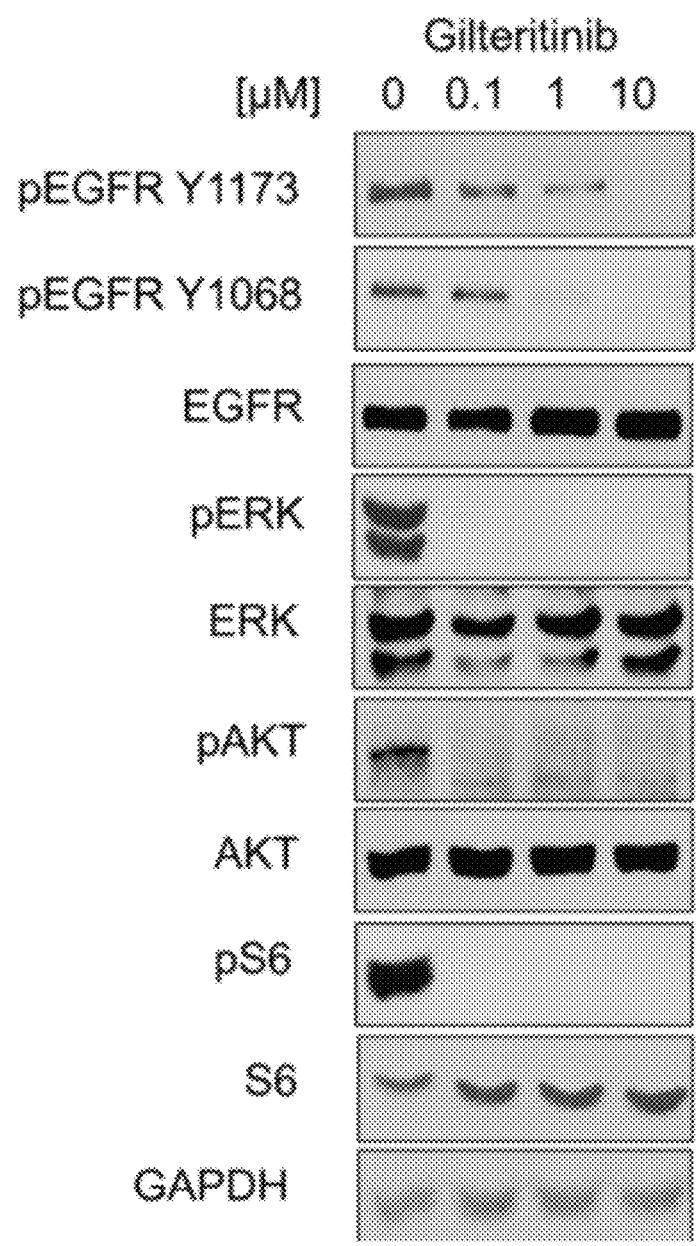

The ability of gilteritinib to inhibit EGFR complex formation was tested using MaMTH (FIG. 22a). Gilteritinib inhibited complex formation between Shc1 and EGFR mutants L858R/T790M and L858R/T790M/C797S, but not wild-type EGFR, in a dose-dependent manner. In vitro kinase assays demonstrated that that gilteritinib preferentially inhibits the kinase activity of EGFR ex19del-T790M, ex19del-T790M-C797S, and L858R/T790M/C797S, with the most robust inhibition demonstrated for ex19del-T790M-C797S (FIG. 22b). Examination of the effects of gilteritinib on mutant EGFR activation and downstream signaling was carried out in PC9 cells expressing EGFR-ex19del-T790M-C797S (FIGS. 22c and 23). Gilteritinb had an inhibitory effect on the phosphorylation and/or expression of EGFR and downstream signaling molecules (FIG. 22c). Gilteritinib caused a dose-dependent reduction in viability of PC9 organoids expressing EGFR-ex19del-T790M-C797S that was not observed for osimertinib (FIG. 23). The potency gilteritinib against cell viability was significantly enhanced in the presence of the therapeutic anti-EGFR therapeutic antibody Panitumumab EGFR-ex19del-T790M-C797S triple mutants, similar to the behavior of midostaurin (FIG. 23b).

Briefly, PC9 EGFR ex19del/T790M/C797S cells were seeded into 96 well plates and treated with 10 ug/ml Panitumumab in combination with different doses of Gilteritinib or Midostaurin. Cells were allowed to grow for 72 hours before measuring cell viability using CellTitre blue reagent.

Example 5

Analog and Combination Treatment

Figure 24:
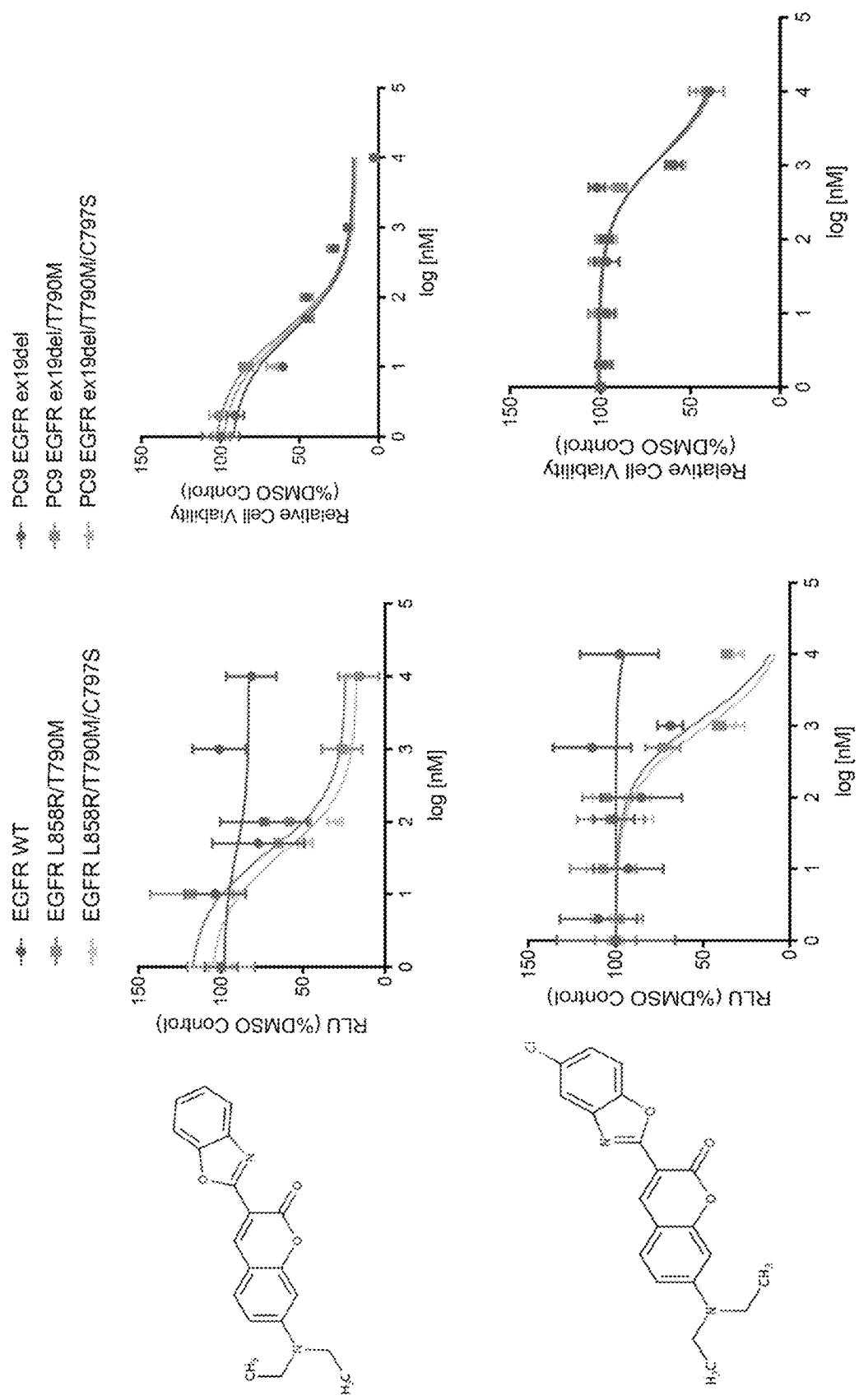
FIG. 24 is a series of graphs and tables demonstrating effect of exemplary compounds of the disclosure.
Figure 24:
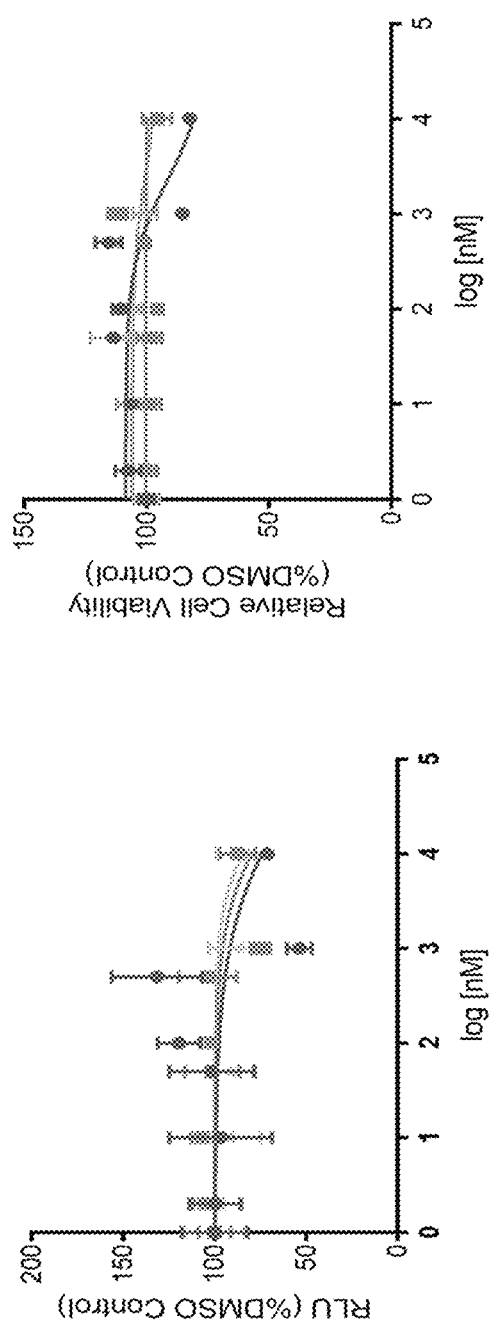

FIG. 24 shows the dose response analysis from MaMTH-DS screens of EGFR L858R/T790M/C797S in the presence of Shc1, and the PC9 cell viability results for 5213777 and a chlorine substituted analog. Also shown is a benzoxazolyl-chromen-2-one compound which did not show does response or toxicity for comparison.

Figure 25B:
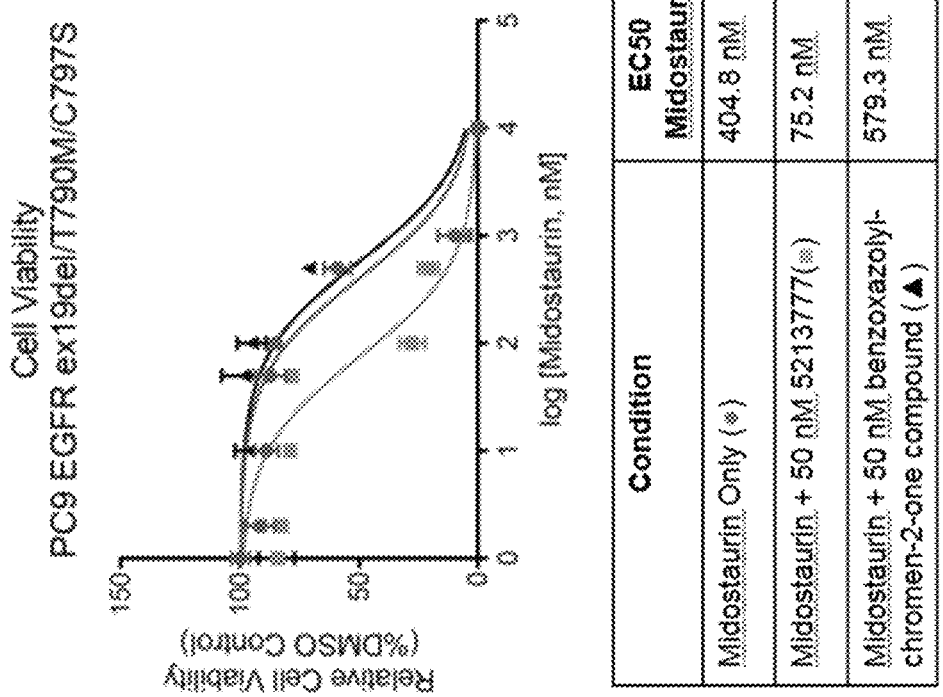
FIG. 25 a-b is a series of graphs and tables demonstrating effect of exemplary mixtures of the disclosure.
Figure 25A:
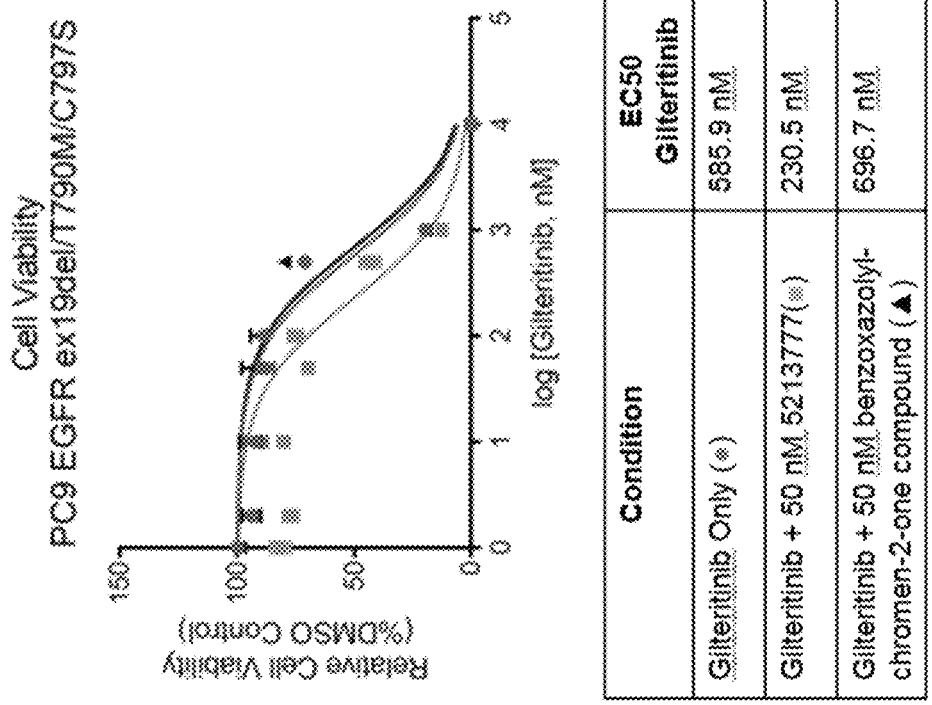

As shown in FIG. 25, Gilteritinib (a) or Midostaurin (b) in combination with 50 nM of compound 5213777 has an increased effect at reducing the cell viability of PC9 EGFR ex19del/T790M/C797S cells after 72 hours compared to Gilteritinib or Midostaurin alone. No combination effect was observed with the benzoxazolyl-chromen-2-one compound which did not show toxicity when added on its own to cells overexpressing EGFR ex19del/T790M/C797S.

Example 6

Biopsies from patients with lung cancer are tested for the presence of the EGFR/L858R/T790M double or EGFR/L858R/T790M/C797S triple mutations. Patients that test positive, are then will be administered with a therapeutically effective amount of gilteritinib in combination with a therapeutically effective amount of one or more of the compounds of formula I, II, or III of the disclosure and/or an EGFR therapeutic antibody.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

1. Petschnigg, J. et al. The mammalian-membrane two-hybrid assay (MaMTH) for probing membrane-protein interactions in human cells. Nat. Methods 11, 585-92 (2014).
2. Yao, Z. et al. A Global Analysis of the Receptor Tyrosine Kinase-Protein Phosphatase Interactome. Mol. Cell 65, 347-360 (2017).
3. Petschnigg, J. et al. Systematic Identification of Oncogenic EGFR Interaction Partners. J. Mol. Biol. 429, 280-294 (2017).
4. Goździk-Spychalska, J. et al. C-MET inhibitors in the treatment of lung cancer. Curr. Treat. Options Oncol. 15, 670-82 (2014).
5. da Cunha Santos, G., Shepherd, F. A. & Tsao, M. S. EGFR Mutations and Lung Cancer. Annu. Rev. Pathol. Mech. Dis. 6, 49-69 (2011).
6. Yu, H. A. et al. Analysis of Tumor Specimens at the Time of Acquired Resistance to EGFR-TKI Therapy in 155 Patients with EGFR-Mutant Lung Cancers. Clin. Cancer Res. 19, 2240-2247 (2013).
7. Thress, K. S. et al. Acquired EGFR C797S mutation mediates resistance to AZD9291 in non-small cell lung cancer harboring EGFR T790M. Nat. Med. 21, 560-2 (2015).
8. Jones, S. & Rappoport, J. Z. Interdependent epidermal growth factor receptor signalling and trafficking. Int. J. Biochem. Cell Biol. 51, 23-28 (2014).
9. Lin, S. Y. et al. Nuclear localization of EGF receptor and its potential new role as a transcription factor. Nat. Cell Biol. 3, 802-8 (2001).
10. Robbins, A. K. & Horlick, R. A. Macrophage scavenger receptor confers an adherent phenotype to cells in culture. Biotechniques 25, 240-4 (1998).
11. Box, G. E. P. and Cox, D. R. An analysis of transformations. R. Stat. Soc 26, 211-252 (1964).
12. Zhang, J.-H., Chung & Oldenburg. A Simple Statistical Parameter for Use in Evaluation and Validation of High Throughput Screening Assays. J. Biomol. Screen. 4, 67-73 (1999).
13. Brideau, C., Gunter, B., Pikounis, B. & Liaw, A. Improved Statistical Methods for Hit Selection in High-Throughput Screening. J. Biomol. Screen. 8, 634-647 (2003).
14. Zabludoff, S. D. et al. AZD7762, a novel checkpoint kinase inhibitor, drives checkpoint abrogation and potentiates DNA-targeted therapies. Mol. Cancer Ther. 7, 2955-2966 (2008).
15. Sausville, E. et al. Phase I dose-escalation study of AZD7762, a checkpoint kinase inhibitor, in combination with gemcitabine in US patients with advanced solid tumors. Cancer Chemother. Pharmacol. 73, 539-549 (2014).
16. Levis, M. Midostaurin approved for FLT3-mutated AML. Blood 129, 3403-3406 (2017).
17. Lee, H.-J. et al. Noncovalent wild-type-sparing inhibitors of EGFR T790M. Cancer Discov. 3, 168-81 (2013).
18. Uchibori, K. et al. Brigatinib combined with anti-EGFR antibody overcomes osimertinib resistance in EGFR-mutated non-small-cell lung cancer. Nat. Commun. 8, 14768 (2017).
19. Gibson, D. G. et al. Enzymatic assembly of DNA molecules up to several hundred kilobases. Nat. Methods 6, 343-345 (2009).

20. Yang, X. et al. A public genome-scale lentiviral expression library of human ORFs. *Nat. Methods* 8, 659-61 (2011).
21. R-Core-Team. R: A language and environment for statistical computing. (2017). at <www.R-project.org>
22. Boutros, M., Ligia, P., Bras, L. & Huber, W. Analysis of cell-based RNAi screens. *Genome Biol.* 7, R66 (2006).
23. Lee, H J et al. EGFR T790M-Selective Indolocarbazole Compounds. *Cancer Discov* 3, 168-181(2013)
24. Costa D B and Kobayashi Transl Lung Cancer Res 4: 809-815 (2015)
25. Kim, S-N. et al. 7-Diethylamino-3(2'benzoxazolyl)-coumarin is a novel microtubule inhibitor with antimitotic activity in multidrug resistant cells. *Biochem. Pharmacol.* 77, 1773-1779.

We claim:

1. A method of inhibiting activity of a mutant epidermal growth factor receptor (EGFR) in a cell comprising contacting the cell with a compound selected from 3-(1,3-benzoxazol-2-yl)-7-(diethylamino)-2H-chromen-2-one and a structurally related analog thereof, the structurally related analog thereof selected from benzoxazolyl and/or chromenone containing compounds, substituted versions thereof or a salt or solvate of any of the foregoing optionally a halogen substituted benzoxazolyl analog thereof or a chlorine substituted analog thereof as well as mixtures thereof; gilteritinib or a salt or solvate thereof and 3-(carbamoylamino)-5-(3-fluorophenyl)-N-[(3S)-piperdin-3-yl]thiophene-2-carboxamide; or any mixtures thereof, wherein the mutant EGFR is a mutant EGFR comprising a mutation selected from an ex19Del, L858R, ex19Del-T790M, L858R-T790M or a C797 mutation.

2. The method of claim 1, wherein the mutant EGFR is a mutant EGFR having a C797 mutation, optionally a C797S mutation, optionally ex19Del-T790M-C797S or L858R-T790M-C797S.

3. The method of claim 1, wherein the cell is a lung cancer cell, optionally non-small cell lung cancer cell.

4. The method of claim 1, wherein the cell is in vivo.

5. The method of claim 4, wherein the cell in vivo is in a subject afflicted with a lung cancer having a mutant EGFR, and the contacting the cell comprises
   a) administering to the subject in need thereof a therapeutically effective amount of a compound selected from 3-(1,3-benzoxazol-2-yl)-7-(diethylamino)-2H-chromen-2-one, and a structurally related analog thereof; the structurally related analog thereof selected from benzoxazolyl and/or chromenone containing compounds, substituted versions thereof or a salt or solvate of any of the foregoing, optionally a halogen substituted benzoxazolyl analog thereof or a chlorine substituted analog as well as mixtures thereof, gilteritinib or a salt or solvate thereof; and 3-(carbamoylamino)-5-(3-fluorophenyl)-N-[(3S)-piperidin-3-yl]thiophene-2-carboxamide; or mixtures and/or combinations comprising the compound or any mixture thereof; or
   b) administering to a subject afflicted with an EGFR C797 mutant lung cancer a therapeutically effective amount of midostaurin or a salt or solvate thereof.

6. The method of claim 5 wherein the compound is gilteritinib or 3-(carbamoylamino)-5-(3-fluorophenyl)-N-[(3S)-piperidin-3-yl]thiophene-2-carboxamide.

7. The method of claim 5 wherein the lung cancer comprises EGFR mutations ex19Del-T790M or L858R-T790M and the compound is selected from 3-(1,3-benzoxazol-2-yl)-7-(diethylamino)-2H-chromen-2-one and a structurally related analog thereof, the structurally related analog thereof selected from benzoxazolyl and/or chromenone containing compounds, substituted versions thereof or a salt or solvate of any of the foregoing, optionally a halogen substituted benzoxazolyl analog thereof or a chlorine substituted analog; gilteritinib or a salt or solvate thereof; and 3-(carbamoylamino)-5-(3-fluorophenyl)-N-[(3S)-piperidin-3-yl]thiophene-2-carboxamide.

8. The method of claim 5 wherein the lung cancer is resistant to tyrosine kinase inhibitors that are effective for lung cancers having EGFR double mutants L858R-T790M or ex19Del-T790M, optionally the lung cancer is resistant to osimertinib.

9. The method of claim 5 wherein the lung cancer is a drug-resistant lung cancer associated with C797 mutation, optionally C797S mutation.

10. The method of claim 9 wherein the drug resistant lung cancer comprises EGFR mutations ex19Del-T790M-C797S or L858R-T790M-C797S.

11. The method of claim 5 wherein the lung cancer is a NSCLC.

12. The method of claim 5, wherein the subject is administered a mixture of the compounds or a combination comprising the compound or mixture and an additional component, optionally wherein the compound or mixture and the additional component of the combination are administered contemporaneously or sequentially.

13. The method of claim 12, wherein the additional component is an anti-EGFR therapeutic antibody.

14. The method of claim 13 wherein the anti-EGFR therapeutic antibody is cetuximab or an antigen-binding fragment thereof.

15. The method of claim 13 wherein the anti-EGFR therapeutic antibody is panitumumab or an antigen-binding fragment thereof.

16. The method of claim 5, wherein the method further comprises obtaining a blood sample, plasma sample or tissue sample from the patient, testing the sample for EGFR mutation status and treating the subject if the subject has a mutant EGFR.

17. The method of claim 1, wherein the chlorine substituted analog is 3-(5-chloro-1,3-benzoxazol-2-yl)-7-(diethylamino)-2H-chromen-2-one.

18. The method of claim 1, wherein the chromenone containing compound is selected from the following chromen-2-one derivatives: 7-Methoxy-3-(2-methyl-thiazol-4-yl)-chro-men-2-one; 7-Ethoxy-3-(2-methyl-thiazol-4-yl)-chro-men-2-one; 3-(2-[4-(Chromen-2-one-3-yl)tiazol-2-yl]thia-zol-4-yl)-chromen-2-one; 7-Methoxy-3-(2-methyl-thiazol-4-yl)-chro-men-2-one; 7-Hydroxy-3-(2-phenyl-thiazol-4-yl)-chro-men-2-one; 6-Methoxy-3-[4-(4-methoxy-phenyl)-thia-zol-2-yl]-chromen-2-one; 7-Hydroxy-3-[4-(4-methoxy-phenyl)-thia-zol-2-yl]-chromen-2-one; 7-Diethylamino-3-[2-(4-dimethylamino-phenyl)-thiazol-4-yl]-chromen-2-one; 3-[4-(4-Chloro-phenyl)-thiazol-2-yl]-6-hex-yl-7-hydroxy-chromen-2-one; 6-Hexyl-7-hydroxy-3-[4-(4-phenoxy-phe-nyl)-thiazol-2-yl]-chromen-2-one; 7-Hydroxy-3-[4-(4-phenoxy-phenyl)-thia-zol-2-yl]-chromen-2-one; 6-Hexyl-7-hydroxy-3-[4-(4-methoxy-phe-nyl)-thiazol-2-yl]-chromen-2-one; 7-Diethylamino-3-(4-methyl-thiazol-2-yl)-chro-men-2-one; 3-[4-(4-Bromo-phenyl)-thiazol-2-yl]-6-hex-yl-7-hydroxy-chromen-2-one; 6-Hexyl-7-hydroxy-3-(2-phenyl-thia-zol-4-yl)-chromen-2-one, 6-Hexyl-7-hydroxy-3-(4-phenyl-thiazol-2-yl)-chromen-2-one; 7-Hydroxy-3-(4-phenyl-thiazol-2-yl)-chro-men-2-one; 6-Hexyl-7-hydroxy-3-(4-methyl-thiazol-2-yl)-chromen-2-one; 7-Hydroxy-3-(5-methyl-4- phenyl-thiazol-2-yl)-chromen-2-one; 3-[4-(4-Chloro-4-phenyl)-5-methyl-thiazol-2-yl]-7-hydroxy-chromen-2-one; 7-Hydroxy-3-(5-methyl-4-p-tolyl-thiazol-2-yl)-chromen-2-one; 6-Bromo-3-[4-(4-ethoxy-phenyl)-thia-zol-2-yl]-chromen-2-one; 3-[4-(4-Ethyl-phenyl)-5-methyl-thiazol-2-yl]-7-hydroxy-chromen-2-one; 3-[4-(4-Chloro-phenyl)-thiazol-2-yl]-6-meth-oxy-chromen-2-one; 3-[2-(3,4-Dimethoxy-phenyl)-thiazol-4-yl]-chro men-2-one; 3-[4-(4-Bromo-phenyl)-5-ethyl-thiazol-2-yl]-7-hydroxy-chromen-2-one; 3-(4,5-Dihydro-naphtho[1,2-d]thiazol-2-yl)-7-hydroxy-chromen-2-one; 7-Diethylamino-3-(4-phenyl-thiazol-2-yl)-chro-men-2-one; 3-[4-(3,4-Dichloro-phenyl)-5-methyl-thiazol-2-yl]-7-hydroxy-chromen-2-one; 3-[4-(4-Chloro-phenyl)-5-ethyl-thia-zol-2-yl]-7-hydroxy-chromen-2-one; 3-(5-Ethyl-4-p-tolyl-thiazol-2-yl)-7-hy-droxy-chromen-2-one; 7-Diethylamino-3-(2-phenyl-thiazol-4-yl)-chro-men-2-one; 3-[4-(2,5-Dimethyl-phenyl)-5-ethyl-thiazol-2-yl]-7-hydroxy-chromen-2-one; 3-[2-(4-Hydroxy-phenyl)-thiazol-4-yl]-chro-men-2-one; 3-(5-Ethyl-4-phenyl-thiazol-2-yl)-7-hy-droxy-chromen-2-one; 3-[2-(2,4-Dimethyl-phenyl)-thiazol-4-yl]-7-hy-droxy-chromen-2-one; 3-[4-(3-Bromo-phenyl)-thiazol-2-yl]-8-meth-oxy-chromen-2-one; 7-Hydroxy-3-[4-(3-methoxy-phenyl)-thiazol-2-yl]-chromen-2-one; 3-Benzothiazol-2-yl-7-hydroxy-chro-men-2-one; 3-(5-Chloro-1H-benzoimidazol-2-yl)-8-meth-oxy-chromen-2-one; 3-[5-(3-Fluoro-phenyl)-[1,3,4]oxa-diazol-2-yl]-8-methoxy-chromen-2-one; 3-Benzo[d]imidazo[2,1-b]thiazol-2-yl-chro-men-2-one; 3-(7-Methoxy-benzo[d]imidazo[2,1-b]thia-zol-2-yl)-chromen-2-one: 6-Chloro-3-(7-fluoro-benzo[d]imi-dazo[2,1-b]thiazol-2-yl)-chromen-2-one; 3-Benzo[d]imidazo[2,1-b]thiazol-2-yl-6-hex-yl-7-hydroxy-chromen-2-one; 6,8-Dichloro-3-(5-p-tolylamino-[1,3,4]thia-diazol-2-yl)-chromen-2-one; 3-[5-(3-Chloro-phenyl)-[1,3,4]oxa-diazol-2-yl]-6-hexyl-7-hydroxy-chro-men-2-one; 6-Hexyl-7-hydroxy-3-[5-(3-methoxy-phe-nyl)-[1,3,4]oxadiazol-2-yl]-chro-men-2-one; 6-Hexyl-7-hydroxy-3-(7-methyl-imidazo[1,2-a]pyridin-2-yl)-chromen-2-one; 6-Methoxy-3-[2-(4-methoxy-phenyl-amino)-thiazol-5-yl]-chromen-2-one; and 6-Hexyl-7-hydroxy-3-[5-(3,4,5-trimeth-oxy-phenyl)-[1,3,4]oxadiazol-2-yl]-chro-men-2-one.

19. The method of claim 5, wherein the chlorine substituted analog is 3-(5-chloro-1,3-benzoxazol-2-yl)-7-(diethylamino)-2H-chromen-2-one.

20. The method of claim 5, wherein the chromenone containing compound is selected from the following chromen-2-one derivatives: 7-Methoxy-3-(2-methyl-thiazol-4-yl)-chro-men-2-one; 7-Ethoxy-3-(2-methyl-thiazol-4-yl)-chro-men-2-one; 3-(2-[4-(Chromen-2-one-3-yl)tiazol-2-yl]thia-zol-4-yl)-chromen-2-one; 7-Methoxy-3-(2-methyl-thiazol-4-yl)-chro-men-2-one: 7-Hydroxy-3-(2-phenyl-thiazol-4-yl)-chro-men-2-one; 6-Methoxy-3-[4-(4-methoxy-phenyl)-thia-zol-2-yl]-chromen-2-one; 7-Hydroxy-3-[4-(4-methoxy-phenyl)-thia-zol-2-yl]-chromen-2-one; 7-Diethylamino-3-[2-(4-dimethylamino-phenyl)-thiazol-4-yl]-chromen-2-one; 3-[4-(4-Chloro-phenyl)-thiazol-2-yl]-6-hex-yl-7-hydroxy-chromen-2-one; 6-Hexyl-7-hydroxy-3-[4-(4-phenoxy-phe-nyl)-thiazol-2-yl]-chromen-2-one: 7-Hydroxy-3-[4-(4-phenoxy-phenyl)-thia-zol-2-yl]-chromen-2-one; 6-Hexyl-7-hydroxy-3-[4-(4-methoxy-phe-nyl)-thiazol-2-yl]-chromen-2-one; 7-Diethylamino-3-(4-methyl-thiazol-2-yl)-chro-men-2-one; 3-[4-(4-Bromo-phenyl)-thiazol-2-yl]-6-hex-yl-7-hydroxy-chromen-2-one; 6-Hexyl-7-hydroxy-3-(2-phenyl-thia-zol-4-yl)-chromen-2-one, 6-Hexyl-7-hydroxy-3-(4-phenyl-thi-azol-2-yl)-chromen-2-one; 7-Hydroxy-3-(4-phenyl-thiazol-2-yl)-chro-men-2-one; 6-Hexyl-7-hydroxy-3-(4-methyl-thiazol-2-yl)-chromen-2-one; 7-Hydroxy-3-(5-methyl-4-phenyl-thiazol-2-yl)-chromen-2-one; 3-[4-(4-Chloro-4-phenyl)-5-methyl-thiazol-2-yl]-7-hydroxy-chromen-2-one; 7-Hydroxy-3-(5-methyl-4-p-tolyl-thiazol-2-yl)-chromen-2-one: 6-Bromo-3-[4-(4-ethoxy-phenyl)-thia-zol-2-yl]-chromen-2-one; 3-[4-(4-Ethyl-phenyl)-5-methyl-thiazol-2-yl]-7-hydroxy-chromen-2-one: 3-[4-(4-Chloro-phenyl)-thiazol-2-yl]-6-meth-oxy-chromen-2-one; 3-[2-(3,4-Dimethoxy-phenyl)-thiazol-4-yl]-chro-men-2-one; 3-[4-(4-Bromo-phenyl)-5-ethyl-thiazol-2-yl]-7-hydroxy-chromen-2-one; 3-(4,5-Dihydro-naphtho[1,2-d]thiazol-2-yl)-7-hydroxy-chromen-2-one; 7-Diethylamino-3-(4-phenyl-thiazol-2-yl)-chro-men-2-one; 3-[4-(3,4-Dichloro-phenyl)-5-methyl-thiazol-2-yl]-7-hydroxy-chromen-2-one: 3-[4-(4-Chloro-phenyl)-5-ethyl-thia-zol-2-yl]-7-hydroxy-chromen-2-one; 3-(5-Ethyl-4-p-tolyl-thiazol-2-yl)-7-hy-droxy-chromen-2-one; 7-Diethylamino-3-(2-phenyl-thiazol-4-yl)-chro-men-2-one; 3-[4-(2,5-Dimethyl-phenyl)-5-ethyl-thiazol-2-yl]-7-hydroxy-chromen-2-one; 3-[2-(4-Hydroxy-phenyl)-thiazol-4-yl]-chro-men-2-one; 3-(5-Ethyl-4-phenyl-thiazol-2-yl)-7-hy-droxy-chromen-2-one: 3-[2-(2,4-Dimethyl-phenyl)-thiazol-4-yl]-7-hy-droxy-chromen-2-one; 3-[4-(3-Bromo-phenyl)-thiazol-2-yl]-8-meth-oxy-chromen-2-one; 7-Hydroxy-3-[4-(3-methoxy-phenyl)-thiazol-2-yl]-chromen-2-one; 3-Benzothiazol-2-yl-7-hydroxy-chro-men-2-one; 3-(5-Chloro-1H-benzoimidazol-2-yl)-8-meth-oxy-chromen-2-one; 3-[5-(3-Fluoro-phenyl)-[1,3,4]oxa-diazol-2-yl]-8-methoxy-chromen-2-one; 3-Benzo[d]imidazo[2,1-b]thiazol-2-yl-chro-men-2-one; 3-(7-Methoxy-benzo[d]imidazo[2,1-b]thia-zol-2-yl)-chromen-2-one; 6-Chloro-3-(7-fluoro-benzo[d]imi-dazo[2,1-b]thiazol-2-yl)-chromen-2-one; 3-Benzo[d]imidazo[2,1-b]thiazol-2-yl-6-hex-yl-7-hydroxy-chromen-2-one; 6,8-Dichloro-3-(5-p-tolylamino-[1,3,4]thia-diazol-2-yl)-chromen-2-one; 3-[5-(3-Chloro-phenyl)-[1,3,4]oxa-diazol-2-yl]-6-hexyl-7-hydroxy-chro-men-2-one; 6-Hexyl-7-hydroxy-3-[5-(3-methoxy-phe-nyl)-[1,3,4]oxadiazol-2-yl]-chro-men-2-one; 6-Hexyl-7-hydroxy-3-(7-methyl-imidazo[1,2-a]pyridin-2-yl)-chromen-2-one; 6-Methoxy-3-[2-(4-methoxy-phenyl-amino)-thiazol-5-yl]-chromen-2-one; and 6-Hexyl-7-hydroxy-3-[5-(3,4,5-trimeth-oxy-phenyl)-[1,3,4]oxadiazol-2-yl]-chro-men-2-one.

* * * * *